United States Patent
Ku et al.

(10) Patent No.: US 9,783,784 B2
(45) Date of Patent: Oct. 10, 2017

(54) METHODS FOR ESTABLISHING AND IMPROVING THE SURVIVAL OF A POPULATION OF PANCREATIC PROGENITOR OR STEM CELLS

(71) Applicant: CITY OF HOPE, Duarte, CA (US)

(72) Inventors: Hsun Ku, Arcadia, CA (US); David Tirrell, Pasadena, CA (US)

(73) Assignees: CITY OF HOPE, Duarte, CA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 13/831,382

(22) Filed: Mar. 14, 2013

(65) Prior Publication Data

US 2014/0193373 A1    Jul. 10, 2014

Related U.S. Application Data

(60) Provisional application No. 61/749,206, filed on Jan. 4, 2013.

(51) Int. Cl.
| | |
|---|---|
| *C12N 5/00* | (2006.01) |
| *C12N 5/02* | (2006.01) |
| *C12N 5/071* | (2010.01) |
| *A61K 35/39* | (2015.01) |
| *C12Q 1/68* | (2006.01) |
| *G01N 33/569* | (2006.01) |

(52) U.S. Cl.
CPC ............ *C12N 5/0678* (2013.01); *A61K 35/39* (2013.01); *C12Q 1/6881* (2013.01); *G01N 33/56966* (2013.01); *C12N 2501/16* (2013.01); *C12N 2501/335* (2013.01); *C12N 2501/415* (2013.01); *C12N 2501/58* (2013.01); *C12N 2533/52* (2013.01); *C12Q 2600/158* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 2002/0192816 A1* | 12/2002 | Roberts et al. ................ | 435/366 |
| 2004/0115805 A1* | 6/2004 | Tsang .................... | C12N 5/0678 435/366 |
| 2005/0064587 A1* | 3/2005 | Rosenberg et al. ............ | 435/366 |
| 2005/0196427 A1* | 9/2005 | Tirrell et al. ................. | 424/427 |
| 2006/0246582 A1* | 11/2006 | Navran, Jr. .................... | 435/366 |

OTHER PUBLICATIONS

XJ8ZC8E1014, BLAST, Jul. 30, 2014.*
XJD1KY4A014, BLAST, Jul. 30, 2014.*
NP_000492.2 (2014).*
Li et al., J. Cell Sci., 123:2792-2802 (2010).*
Lin et al., PNAS, 108(16):6380-6385 (2011).*
Dor et al., Cell, 132:183-184 (2008).*
Yamada et al., FEBS Lett., 530:48-52 (2002).*
Lin et al., Biomacro., 10:2460-2467 (2009).*
Lutolf et al., Nature Biotechnol., 23(1):47-55 (2005).*
Straley et al., Soft Matter, 5:114-124 (2009).*
Hashimoto et al., Biomater., 25:1407-1414 (2005).*
Alberti K, R. E. Davey, K. Onishi, S. George, K. Salchert, F. P. Seib, M. Bornhauser, T. Pompe, A. Nagy, C. Werner, P. W. Zandstra, Nat Methods 2008, 5, 645.
Bonner-Weir S, et al. (2004) The pancreatic ductal epithelium serves as a potential pool of progenitor cells. Pediatr Diabetes 5 Suppl 2:16-22.
Bonner-Weir S, Taneja M, Weir GC, Tatarkiewicz K, Song KH, Sharma A, O'Neil JJ. In vitro cultivation of human islets from expanded ductal tissue. Proc Natl Acad Sci U S A 2000;97:7999-8004.
Bonner-Weir, Endocrinology 2000, 141, 1926.
Bouwens L. Cytokeratins and cell differentiation in the pancreas. J Pathol 1998;184:234-9.
Chen C, Chai J, Singh L, Kuo CY, Jin L, Feng T, Marzano S, Galeni S, Zhang N, Iacovino M, Qin L, Hara M, Stein R, Bromberg JS, Kyba M, Ku HT. Characterization of an in vitro differentiation assay for pancreatic-like cell development from murine embryonic stem cells: detailed gene expression analysis. Assay Drug Dev Technol 2011;9:403-19.
Copley M.R., Beer, P.A.. and Eaves, C.J. (2012). Hematopoietic stem cell heterogeneity takes center stage. Cell Stem Cell 10, 690-697.
Criscimanna A, et al. (2011) Duct cells contribute to regeneration of endocrine and acinar cells following pancreatic damage in adult mice. Gastroenterology 141(4):1451-1462, 1462 e1451-1456.
D'Amour, K. A., Agulnick, A. D., Eliazer, S., Kelly, O.G., Kroon, E., and Baetge, E.E. (2005). Efficient differentiation of human embryonic stem cells to definitive endoderm. Nature biotechnology 23. 1534-1541.
D'Amour, K.A., Bang, A.G., Eliazer, S., Kelly, O.G., Agulnick, A.D., Smart, N.G., Moorman, M.A., Kroon, E., Carpenter, M.K., and Baetge, E.E. (2006). Production of pancreatic hormone-expressing endocrine cells from human embryonic stem cells. Nature biotechnology, 1392-1401.
de Lau W, et al. (2011) Lgr5 homologues associate with Wnt receptors and mediate R-spondin signalling. Nature 476 (7360):293-297.
Dessimoz J, Bonnard C, Huelsken J, & Grapin-Botton A (2005) Pancreas-specific deletion of beta-catenin reveals Wnt-dependent and Wnt-independent functions during development. Curr Biol 15 (18):1677-1683.

(Continued)

*Primary Examiner* — Thomas J Visone
(74) *Attorney, Agent, or Firm* — Perkins Coie LLP; Lara J. Dueppen; Yang Tang

(57) ABSTRACT

In some embodiments, methods for improving the survival of pancreatic β-cell progenitors in culture are provided. Such methods may include contacting a population of pancreatic progenitor cells with an amino acid (aa) sequence comprising IKVAV (SEQ ID NO:1). In other embodiments, methods for (i) verifying the establishment of a population of pancreatic progenitor or stem cells and (ii) methods for generating or establishing a population of pancreatic endocrine progenitor cells in vitro are provided.

11 Claims, 38 Drawing Sheets

(56) References Cited

OTHER PUBLICATIONS

Dor, Y., Brown, J., Martinez, O.I., and Melton, D.A. (2004). Adult pancreatic beta-cells are formed by self-duplication rather than stem-cell differentiation. Nature 429 (6987): 41-46.
Fanjul M, Gmyr V, Sengenes C, Ratovo G, Dufresne M, Lefebvre B, Kerr-Conte J, Hollande E. Evidence for epithelial-mesenchymal transition in adult human pancreatic exocrine cells. J Histochem Cytochem 2010;58:807-23.
Furuta M, Yano H, Zhou A, Rouille Y, Hoist JJ, Carroll R, Ravazzola M, Orci L, Furuta H, Steiner DF. Defective prohormone processing and altered pancreatic islet morphology in mice lacking active SPC2. Proc Natl Acad Sci U S A 1997;94:6646-51.
Furuyama K, Kawaguchi Y, Akiyama H, Horiguchi M, Kodama S, Kuhara T, Hosokawa S, Elbahrawy A, Soeda T, Koizurni M, Masui T, Kawaguchi M, Takaori K, Doi R, Nishi E, Kakinoki R, Deng JM, Behringer RR, Nakamura T, Uemoto S. Continuous cell supply from a Sox9-expressing progenitor zone in adult liver, exocrine pancreas and intestine. Nat Genet 2011;43:34-41.
Gao R, Ustinov J, Korsgren O, Otonkoski T. In vitro neogenesis of human islets reflects the plasticity of differentiated human pancreatic cells. Diabetologia 2005;48:2296-2304.
Gao R, Ustinov J, Pulkkinen MA, Lundin K, Korsgren O, Otonkoski T. Characterization of endocrine progenitor cells and critical factors for their differentiation in human adult pancreatic cell culture. Diabetes 2003;52:2007-2015.
Githens S. The pancreatic duct cell: proliferative capabilities, specific characteristics, metaplasia, isolation, and culture, J Pediatr Gastroenterol Nutr 1988;7:486-506.
Gong S, Zheng C, Doughty ML, Losos K, Didkovsky N, Schambra UB, Nowak NJ, Joyner A, Leblanc G, Hatten ME, Heintz N. A gene expression atlas of the central nervous system based on bacterial artificial chromosomes. Nature 2003;425:917-25.
Gu G, Brown JR, Melton DA. Direct lineage tracing reveals the ontogeny of pancreatic cell fates during mouse embryogenesis. Mech Dev 2003;120:35-43.
Gu G, Dubauskaite J, & Melton DA (2002) Direct evidence for the pancreatic lineage: NGN3+ cells are islet progenitors and are distinct from duct progenitors. Development 129(10):2447-2457.
Hao E, Tyrberg B, Itkin-Ansari P, Lakey JR, Geron I, Monosov EZ, Barcova M, Mercola M, Levine F. Beta-cell differentiation from nonendocrine epithelial cells of the adult human pancreas. Nature medicine 2006;12:310-316.
Heilshorn, K. A. DiZio, E. R. Welsh, D. A. Tirrell, Biomaterials 2003, 24, 4245.
Heiser PW, Lau J, Taketo MM, Herrera PL, & Hebrok M (2006) Stabilization of beta-catenin impacts pancreas growth. Development 133(10):2023-2032.
Heller RS, et al. (2002) Expression patterns of Wnts, Frizzleds, sFRPs, and misexpression in transgenic mice suggesting a role for Wnts in pancreas and foregut pattern formation. Dev Dyn 225(3):260-270.
Herbach, M. Bergmayr, B. Goke, E. Wolf, R. Wanke, PLoS One 2011, 6, e22814.
Hori Y, Fukumoto M, Kuroda Y. Enrichment of putative pancreatic progenitor cells from mice by sorting for prominin1 (CD133) and platelet-derived growth factor receptor beta. Stem Cells 2008;26:2912-20.
Immervoll H, Hoem D, Sakariassen PO, Steffensen OJ, Molven A. Expression of the "stem cell marker" CD133 in pancreas and pancreatic ductal adenocarcinomas. BMC Cancer 2008;8:48.
Inada A, Nienaber C, Katsuta H, Fujitani Y, Levine J, Morita R, Sharma A, Bonner-Weir S. Carbonic anhydrase II-positive pancreatic cells are progenitors for both endocrine and exocrine pancreas after birth. Proc Natl Acad Sci U S A 2008;105:19915-9.
Jin et al., Colony-forming cells in the adult mouse pancreas are expandable in Matrigel and form endocrine/acinar colonies in laminin hydrogel. PNAS 2012; 1301889110.
Jonsson J, Carlsson L, Edlund T, & Edlund H (1994) Insulin-promoter-factor 1 is required for pancreas development in mice. Nature 371(6498):606-609.
Jorgensen MC, Ahnfelt-Ronne J, Hald J, Madsen OD, Serup P, Hecksher-Sorensen J. An illustrated review of early pancreas development in the mouse. Endocr Rev 2007;28:685-705.
Khademhosseini A, R. Langer, J. Borenstein, J. P. Vacanti, Proc Natl Acad Sci U S A 2006, 103, 2480.
Kilic G, Wang J, Sosa-Pineda B. Osteopontin is a novel marker of pancreatic ductal tissues and of undifferentiated pancreatic precursors in mice. Dev Dyn 2006;235:1659-67.
Kim KA, et al. (2005) Mitogenic influence of human R-spondin1 on the intestinal epithelium. Science 309(5738):1256-1259.
Kobayashi H, Spilde TL, Li Z, Marosky JK, Bhatia AM, Hembree MJ, Prasadan K, Preuett BL, Gittes GK. Lectin as a marker for staining and purification of embryonic pancreatic epithelium. Biochem Biophys Res Commun 2002;293:691-7.
Kopinke D, Murtaugh LC. Exocrine-to-endocrine differentiation is detectable only prior to birth in the uninjured mouse pancreas. BMC Dev Biol 2010;10:38.
Kopp JL, Dubois CL, Schaffer AE, Hao E, Shih HP, Seymour PA, Ma J, Sander M. Sox9+ ductal cells are multipotent progenitors throughout development but do not produce new endocrine cells in the normal or injured adult pancreas. Development 2011a;138:653-65.
Kopp JL, et al. Progenitor cell domains in the developing and adult pancreas. Cell Cycle 2011b; 10(12):1921-1927.
Kragl, E. Lammert, Adv Exp Med Biol 2010, 654, 217.
Kroon, E., Martinson, L.A., Kadoya, K., Bang, A.G., Kelly, O.G., Eliazer, S., Young, H., Richardson, M., Smart, N.G., Cunningham, J., el al. (2008). Pancreatic endoderm derived from human embryonic stem cells generates glucose-responsive insulin-secreting cells in vivo. Nature biotechnology. 2008; 26(4): 443-452.
Ku HT. Minireview: pancreatic progenitor cells—recent studies. Endocrinology 2008;149:4312-4316.
Ku, H.T., Chai, J., Kim, Y.J., White. P., Purohit-Ghelani, S., Kaestner, K.H., and Bromberg, J.S. (2007). Insulin-expressing colonies developed from murine embryonic stem cell-derived progenitors. Diabetes 56, 921-929.
Lardon J, Corbeil D, Huttner WB, Ling Z, Bouwens L. Stem cell marker prominin-1/AC133 is expressed in duct cells of the adult human pancreas. Pancreas 2008;36:e1-6.
Li WC, Rukstalis JM, Nishimura W, Tchipashvili V, Habener JF, Sharma A, Bonner-Weir S. Activation of pancreatic-duct-derived progenitor cells during pancreas regeneration in adult rats. J Cell Sci 2010;123:2792-802.
Lu W, et al.(2008) R-spondin1 synergizes with Wnt3A in inducing osteoblast differentiation and osteoprotegerin expression. FEBS Lett 582(5):643-650.
Malide D, Seidah NG, Chretien M, Bendayan M. Electron microscopic immunocytochemical evidence for the involvement of the converts PC1 and PC2 in the processing of proinsulin in pancreatic beta-cells. J Histochem Cytochem 1995;43:11-9.
May R, Sureban SM, Lightfoot SA, Hoskins AB, Brackett DJ, Postier RG, Ramanujam R, Rao CV, Wyche JH, Anant S, Houchen CW. Identification of a novel putative pancreatic stem/progenitor cell marker DCAMKL-1 in normal mouse pancreas. Am J Physiol Gastrointest Liver Physiol 2010;299:G303-10.
Metcalf D (2007) Concise review: hematopoietic stem cells and tissue stem cells: current concepts and unanswered questions. Stem Cells 25(10):2390-2395.
Nam JS, Turcotte TJ, Smith PF, Choi S, & Yoon JK (2006) Mouse cristin/Rspondin family proteins are novel ligands for the Frizzled 8 and LRP6 receptors and activate beta-catenin-dependent gene expression. J Biol Chem 281(19):13247-13257.
Nikolova, N. Jabs, I. Konstantinova, A. Domogatskaya, K. Tryggvason, L. Sorokin, R. Fassler, G. Gu, H. P. Gerber, N. Ferrara, D. A. Melton, E. Lammert, Dev Cell 2006, 10, 397.
Nowatzki, D. A. Tirrell, Biomaterials 2004, 25, 1261-1267.
Ootani A, et al. (2009) Sustained in vitro intestinal epithelial culture within a Wnt-dependent stem cell niche. Nat Med 15(6):701-706.

(56) References Cited

OTHER PUBLICATIONS

Oshima Y, Suzuki A, Kawashimo K, Ishikawa M, Ohkohchi N, Taniguchi H. Isolation of mouse pancreatic ductal progenitor cells expressing CD133 and c-Met by flow cytometric cell sorting. Gastroenterology 2007;132:720-32.
Parma P, et al. (2006) R-spondin1 is essential in sex determination, skin differentiation and malignancy. Nat Genet 38(11):1304-1309.
Parnaud, E. Hammar, D. G. Rouiller, M. Armanet, P. A. Halban, D. Bosco, Diabetes 2006, 55, 1413-1420.
Peifer M. & Polakis P. (2000) Wnt signaling in oncogenesis and embryogenesis—a look outside the nucleus. Science 287(5458):1606-1609.
Pinho AV, Rooman I, Reichert M, De Medts N, Bouwens L, Rustgi AK, Real FX. Adult pancreatic acinar cells dedifferentiate to an embryonic progenitor phenotype with concomitant activation of a senescence programme that is present in chronic pancreatitis. Gut 2011;60:958-966.
Pinkse, W. P. Bouwman, R. Jiawan-Lalai, O. T. Terpstra, J. A. Bruijn, E. de Heer, Diabetes 2006, 55, 312-317.
Piper K, Ball SG, Keeling JW, Mansoor S, Wilson DI, Hanley NA. Novel SOX9 expression during human pancreas development correlates to abnormalities in Campomelic dysplasia. Mech Dev 2002;116:223-6.
Piper K, Brickwood S, Turnpenny LW, Cameron IT, Ball SG, Wilson DI, Hanley NA. Beta cell differentiation during early human pancreas development. The Journal of endocrinology 2004;181:11-23.
Rajagopal, W. J. Anderson, S. Kume, O. I. Martinez, D. A. Melton, Science 2003, 299, 363.
Rovira M, Scott SG, Liss AS, Jensen J, Thayer SP, Leach SD. Isolation and characterization of centroacinar/terminal ductal progenitor cells in adult mouse pancreas. Proc Natl Acad Sci U S A 2010;107:75-80.
Rulifson IC, et al. (2007) Wnt signaling regulates pancreatic beta cell proliferation. Proc Natl Acad Sci U S A 104(15):6247-6252.
Sato T, et al. (2009) Single Lgr5 stem cells build crypt-villus structures in vitro without a mesenchymal niche. Nature 459(7244):262-265.
Schreiber FS, Deramaudt TB, Brunner TB, Boretti MI, Gooch KJ, Stoffers DA, Bernhard EJ, Rustgi AK. Successful growth and characterization of mouse pancreatic ductal cells: functional properties of the Ki-RAS(G12V) oncogene. Gastroenterology 2004;127:250-60.
Seaberg RM, Smukler SR, Kieffer TJ, Enikolopov G, Asghar Z, Wheeler MB, Korbutt G, van der Kooy D. Clonal identification of multipotent precursors from adult mouse pancreas that generate neural and pancreatic lineages. Nature biotechnology 2004;22:1115-1124.
Seymour PA, Freude KK, Dubois CL, Shih HP, Patel NA, Sander M. A osagedependent requirement for Sox9 in pancreatic endocrine cell formation. Dev Biol 2008;323:19-30.
Seymour PA, Freude KK, Tran MN, Mayes EE, Jensen J, Kist R, Scherer G, Sander M. SOX9 is required for maintenance of the pancreatic progenitor cell pool. Proceedings of the National Academy of Sciences of the United States of America 2007;104:1865-1870.
Sharma A, Zangen DH, Reitz P, Taneja M, Lissauer ME, Miller CP, Weir GC, Habener JF, Bonner-Weir S. The homeodomain protein IDX-1 increases after an early burst of proliferation during pancreatic regeneration. Diabetes 1999;48:507-513.
Shin S, Walton G, Aoki R, Brondell K, Schug J, Fox A, Smirnova O, Dorrell C, Erker L, Chu AS, Wells RG, Grompe M, Greenbaum LE, Kaestner KH. Foxl1-Cre-marked adult hepatic progenitors have clonogenic and bilineage differentiation potential. Genes Dev 2011;25;1185-92.
Smukler SR, Arntfield ME, Razavi R, Bikopoulos G, Karpowicz P, Seaberg R, Dai F, Lee S, Ahrens R, Fraser PE, Wheeler MB, van der Kooy D. The adult mouse and human pancreas contain rare multipotent stem cells that express insulin. Cell Stem Cell 2011;8:281-93.
Solar M, Cardalda C, Houbracken I, Martin M, Maestro MA, De Medts N, Xu X, Grau V, Heimberg H, Bouwens L, Ferrer J. Pancreatic exocrine duct cells give rise to insulin-producing beta cells during embryogenesis but not after birth. Dev Cell 2009;17:849-60.
Suarez-Pinzon WL, Lakey JR, Brand SJ, Rabinovitch A. Combination therapy with epidermal growth factor and gastrin induces neogenesis of human islet {beta}-cells from pancreatic duct cells and an increase in functional {beta}-cell mass. J Clin Endocrinol Metab 2005;90:3401-9.
Sugiyama T, Rodriguez RT, McLean GW, Kim SK. Conserved markers of fetal pancreatic epithelium permit prospective isolation of islet progenitor cells by FACS. Proceedings of the National Academy of Sciences of the United States of America 2007;104:175-180.
Suzuki A, Nakauchi H, Taniguchi H. Prospective isolation of multipotent pancreatic progenitors using flow-cytometric cell sorting. Diabetes 2004;53:2143-2152.
Teta M, Rankin Mm, Long SY, Stein GM, & Kushner JA (2007) Growth and regeneration of adult beta cells does not involve specialized progenitors. Developmental cell 12(5):817-826.
Thorel F, et al. (2010) Conversion of adult pancreatic alpha-cells to beta-cells after extreme beta-cell loss. Nature 464(7292):1149-1154.
Walker NI, Winterford CM, Kerr JF. Ultrastructure of the rat pancreas after experimental duct ligation. II. Duct and stromal cell proliferation, differentiation, and deletion. Pancreas 1992;7:420-34.
Wang H, Brun T, Kataoka K, Sharma AJ, Wollheim CB. MAFA controls genes implicated in insulin biosynthesis and secretion. Diabetologia 2007;50:348-58.
Watanabe M, Muramatsu T, Shirane H, Ugai K. Discrete Distribution of binding sites for Dolichos biflorus agglutinin (DBA) and for peanut agglutinin (PNA) in mouse organ tissues. J Histochem Cytochem 1981;29:779-80.
Weber, K. N. Heyde, K. Haskins, K. S. Anseth, Biomaterials 2007, 28, 3004-3011.
Weber, L.M., and Anseth, K.S. (2008). Hydrogel encapsulation environments functionalized with extracellular matrix imeractions increase islet insulin secretion. Matrix biology: Journal of the International Society for Matrix Biology 27, 667-673.
Weber, L.M., Lopez, C. G., and Anseth, K.S. (2009). Effects of PEG hydrogel crosslinking density on protein diffusion and encapsulated islet survival and function. J Biomed Mater Res A 90, 720-729.
Wescott MP, Rovira M, Reichert M, von Burstin J, Means A, Leach SD, Rustgi AK. Pancreatic ductal morphogenesis and the Pdx1 homeodomain transcription factor. Mol Biol Cell 2009;20:4838-44.
Wheeldon, A. Farhadi, A. G. Bick, E. Jabbari, A. Khademhosseini, Nanotechnology 2011, 22, 212001.
Winkler, M., Trieu, N., Feng, T., Jin, L., Walker, S., Singh, L., and Ku, H.T. (2011). A quantitative assay for insulin-expressing colony-forming progenitors. J Vis Exp, e3148.
Wong VS, Yeung A, Schultz W, & Brubaker PL (2010) R-spondin-1 is a novel beta-cell growth factor and insulin secretagogue. J Biol Chem 285(28):21292-21302.
Xu X, D'Hoker J, Stange G, Bonne S, De Leu N, Xiao X, Van de Casteele M, Mellitzer G, Ling Z, Pipeleers D, Bouwens L, Scharfrnann R, Gradwohl G, Heimberg H. Beta cells can be generated from endogenous progenitors in injured adult mouse pancreas. Cell 2008;132:197-207.
Yatoh S, Dodge R, Akashi T, Omer A, Sharma A, Weir GC, Bonner-Weir S. Differentiation of affinity-purified human pancreatic duct cells to beta-cells. Diabetes 2007;56:1802-1809.
Zhao J, et al. (2007a) R-spondin1, a novel intestinotrophic mitogen, ameliorates experimental colitis in mice. Gastroenterology 132(4):1331-1343.
Zhou Q, et al. (2007b) A multipotent progenitor domain guides pancreatic organogenesis. Developmental cell 13(1):103-114.

* cited by examiner (A)

(B)

(A)

(B)

bars=100

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Ile Lys Val Ala Val
1               5

```
<210> SEQ ID NO 2
<211> LENGTH: 26
<212> TYPE: PRT
<213> ORGANISM: Artificial Sequence
<220> FEATURE:
<223> OTHER INFORMATION: Synthetic peptide

<400> SEQUENCE: 2

Leu Asp Ala Ser Cys Ser Arg Ala Arg Lys Gln Ala Ala Ser Ile Lys
1               5                   10                  15

Val Ala Val Ser Ala Asp Arg Ala Ser Ala
            20                  25

<210> SEQ ID NO 3
<211> LENGTH: 100
<212> TYPE: PRT
<213> ORGANISM: Artificial Sequence
<220> FEATURE:
<223> OTHER INFORMATION: Synthetic peptide

<400> SEQUENCE: 3

Val Pro Gly Ile Gly Val Pro Gly Ile Gly Val Pro Gly Lys Gly Val
1               5                   10                  15

Pro Gly Ile Gly Val Pro Gly Ile Gly Val Pro Gly Ile Gly Val Pro
            20                  25                  30

Gly Ile Gly Val Pro Gly Lys Gly Val Pro Gly Ile Gly Val Pro Gly
        35                  40                  45

Ile Gly Val Pro Gly Ile Gly Val Pro Gly Ile Gly Val Pro Gly Lys
    50                  55                  60

Gly Val Pro Gly Ile Gly Val Pro Gly Ile Gly Val Pro Gly Ile Gly
65                  70                  75                  80

Val Pro Gly Ile Gly Val Pro Gly Lys Gly Val Pro Gly Ile Gly Val
                85                  90                  95

Pro Gly Ile Gly
            100

<210> SEQ ID NO 4
<211> LENGTH: 28
<212> TYPE: PRT
<213> ORGANISM: Artificial Sequence
<220> FEATURE:
<223> OTHER INFORMATION: Synthetic aECM protein
<220> FEATURE:
<221> NAME/KEY: NON_CONS
<222> LOCATION: (20)..(21)
<223> OTHER INFORMATION: "X-Y" present between residues 20 and 21
      wherein X is substituted with a laminin component and Y is
      substituted with a portion or fragment of an ECM protein
<220> FEATURE:
<221> NAME/KEY: NON_CONS
<222> LOCATION: (22)..(23)
<223> OTHER INFORMATION: "X-Y", present between residues 22 and 23,
      wherein X is substituted with a laminin component and Y is
      substituted with a portion or fragment of an ECM protein
<220> FEATURE:
<221> NAME/KEY: NON_CONS
<222> LOCATION: (24)..(25)
<223> OTHER INFORMATION: "X-Y", present between residues 24 and 25,
      wherein X is substituted with a laminin component and Y is
      substituted with a portion or fragment of an ECM protein

<400> SEQUENCE: 4

Met Ala Ser Met Thr Gly Gly Gln Gln Met Gly His His His His
1               5                   10                  15

His Met Lys Leu Val Pro Val Pro Val Pro Leu Glu
            20                  25
```

```
<210> SEQ ID NO 5
<211> LENGTH: 328
<212> TYPE: PRT
<213> ORGANISM: Artificial Sequence
<220> FEATURE:
<223> OTHER INFORMATION: Synthetic aECM protein
<220> FEATURE:
<221> NAME/KEY: NON_CONS
<222> LOCATION: (20)..(21)
<223> OTHER INFORMATION: "X", present between residues 21 and 21, is
      substituted with a laminin component
<220> FEATURE:
<221> NAME/KEY: NON_CONS
<222> LOCATION: (122)..(123)
<223> OTHER INFORMATION: "X", present between residues 122 and 123, is
      substituted with a laminin component
<220> FEATURE:
<221> NAME/KEY: NON_CONS
<222> LOCATION: (224)..(225)
<223> OTHER INFORMATION: "X", present between residues 224 and 225, is
      substituted with a laminin component

<400> SEQUENCE: 5

Met Ala Ser Met Thr Gly Gly Gln Gln Met Gly His His His His
1               5                   10                  15

His Met Lys Leu Val Pro Gly Ile Gly Val Pro Gly Ile Gly Val Pro
            20                  25                  30

Gly Lys Gly Val Pro Gly Ile Gly Val Pro Gly Ile Gly Val Pro Gly
        35                  40                  45

Ile Gly Val Pro Gly Ile Gly Val Pro Gly Lys Gly Val Pro Gly Ile
    50                  55                  60

Gly Val Pro Gly Ile Gly Val Pro Gly Ile Gly Val Pro Gly Ile Gly
65                  70                  75                  80

Val Pro Gly Lys Gly Val Pro Gly Ile Gly Val Pro Gly Ile Gly Val
                85                  90                  95

Pro Gly Ile Gly Val Pro Gly Ile Gly Val Pro Gly Lys Gly Val Pro
            100                 105                 110

Gly Ile Gly Val Pro Gly Ile Gly Val Pro Val Pro Gly Ile Gly Val
        115                 120                 125

Pro Gly Ile Gly Val Pro Gly Lys Gly Val Pro Gly Ile Gly Val Pro
    130                 135                 140

Gly Ile Gly Val Pro Gly Ile Gly Val Pro Gly Ile Gly Val Pro Gly
145                 150                 155                 160

Lys Gly Val Pro Gly Ile Gly Val Pro Gly Ile Gly Val Pro Gly Ile
                165                 170                 175

Gly Val Pro Gly Ile Gly Val Pro Gly Lys Gly Val Pro Gly Ile Gly
            180                 185                 190

Val Pro Gly Ile Gly Val Pro Gly Ile Gly Val Pro Gly Ile Gly Val
            195                 200                 205

Pro Gly Lys Gly Val Pro Gly Ile Gly Val Pro Gly Ile Gly Val Pro
        210                 215                 220

Val Pro Gly Ile Gly Val Pro Gly Ile Gly Val Pro Gly Lys Gly Val
225                 230                 235                 240

Pro Gly Ile Gly Val Pro Gly Ile Gly Val Pro Gly Ile Gly Val Pro
                245                 250                 255

Gly Ile Gly Val Pro Gly Lys Gly Val Pro Gly Ile Gly Val Pro Gly
            260                 265                 270

Ile Gly Val Pro Gly Ile Gly Val Pro Gly Ile Gly Val Pro Gly Lys
        275                 280                 285
```

```
Gly Val Pro Gly Ile Gly Val Pro Gly Ile Gly Val Pro Gly Ile Gly
            290                 295                 300

Val Pro Gly Ile Gly Val Pro Gly Lys Gly Val Pro Gly Ile Gly Val
305                 310                 315                 320

Pro Gly Ile Gly Val Pro Leu Glu
                325

<210> SEQ ID NO 6
<211> LENGTH: 26
<212> TYPE: PRT
<213> ORGANISM: Artificial Sequence
<220> FEATURE:
<223> OTHER INFORMATION: Synthetic peptide

<400> SEQUENCE: 6

Leu Asp Ala Ser Met Ser Val Gln Ala Val Asp Arg Ser Ala Asn Lys
1               5                   10                  15

Ala Arg Ile Val Ser Lys Ala Ala Ser Ala
            20                  25

<210> SEQ ID NO 7
<211> LENGTH: 22
<212> TYPE: PRT
<213> ORGANISM: Artificial Sequence
<220> FEATURE:
<223> OTHER INFORMATION: Synthetic fibronectin-derived RGD peptide

<400> SEQUENCE: 7

Val Pro Leu Asp Tyr Ala Val Thr Gly Arg Gly Asp Ser Pro Ala Ser
1               5                   10                  15

Ser Lys Ile Pro Ile Ala
            20
```

METHODS FOR ESTABLISHING AND IMPROVING THE SURVIVAL OF A POPULATION OF PANCREATIC PROGENITOR OR STEM CELLS

CROSS REFERENCE TO RELATED APPLICATIONS

This application claims the benefit of U.S. Provisional Patent Application No. 61/749,206, filed Jan. 4, 2013 and which is incorporated herein by reference in its entirety.

STATEMENT OF GOVERNMENT INTEREST

This invention was made with government support under RO1 DK081587 and U01 DK089533 each awarded by NIH. The Government has certain rights in the invention.

BACKGROUND

Type 1 diabetes (T1D) occurs when insulin-secreting beta cells (β-cells) in endocrine islets are destroyed due to autoimmunity. Cell replacement therapy using cadaveric islets is a viable treatment option for end-stage T1D patients. However, a severe shortage of cadaveric organs has focused attention on the need for ways to generate beta-like cells from other sources.

Although embryonic ductal cells have been shown to be multipotent and capable of giving rise to duct, acinar and endocrine lineages in mouse models (Solar et al. 2009; Kopinke & Murtaugh 2010; Kopp et al. 2011a) it has generally remained controversial as to whether adult pancreatic ducts include progenitor cells or stem cell-like cells that can give rise to non-ductal pancreatic cells such as endocrine or acinar cells in vivo (Solar et al. 2009; Kopinke & Murtaugh 2010; Kopp et al. 2011a; Inada et al. 2008; Xu et al. 2008).

Regardless, it would be desired to create methods that would give the ability to readily identify, expand and differentiate pancreatic ductal stem or progenitor cells into beta-like cells in vitro to alleviate the organ shortage problem.

SUMMARY

In some embodiments, methods for improving the survival of pancreatic β-cell progenitors in culture are provided. Such methods may include a step of contacting a population of pancreatic progenitor cells with an amino acid sequence comprising IKVAV (SEQ ID NO:1).

In other embodiments, methods for identifying or verifying the establishment of a population of pancreatic progenitor or stem cells are provided. Such methods may include steps of isolating a population of cells from a pancreatic tissue sample that express CD133 and Sox9 (CD133$^+$/Sox9$^+$ cells); culturing at least one of the isolated CD133$^+$/Sox9$^+$ cells with an effective amount of R-Spondin 1 to establish at least one single-cell derived colony; and verifying that the single-cell derived colony comprises a population of pancreatic progenitor or stem cells by detecting expression of one or more pancreatic progenitor cell markers in one or more colony cells. According to some aspects, the one or more pancreatic progenitor cell markers include Pdx1, Ngn3, Nkx6.1, Pax4, MafB, c-Met, DCAMKL1, DCAMKL2, or a combination thereof.

In other embodiments, methods for generating or establishing a population of pancreatic endocrine progenitor cells in vitro are provided. Such methods may include steps of isolating a population of cells from a pancreatic tissue sample that express CD133 and Sox9 (CD133$^+$/Sox9$^+$ cells); culturing at least one of the isolated CD133$^+$/Sox9$^+$ cells with an effective amount of R-Spondin 1 to establish at least one single-cell derived dense colony; dissociating at least one single-cell derived dense colony to form a single-cell suspension; and culturing the single-cell suspension with an amino acid sequence comprising IKVAV (SEQ ID NO:1) in the absence of R-Spondin 1 to establish the population of pancreatic endocrine progenitor cells. In some aspects the methods may also include a step of dissociating and replating the single-cell derived dense colonies with an effective amount of R-Spondin 1 for one or more generations prior to forming a single-cell suspension.

The amino acid sequence comprising IKVAV (SEQ ID NO:1) that is used in the methods described herein may part of an artificial extracellular matrix (aECM) protein according to some embodiments. In some embodiments, the aECM protein may include an amino acid sequence that includes SEQ ID NO:2. In other embodiments, the aECM protein may also include an elastin-based sequence, for example, SEQ ID NO:3.

DETAILED DESCRIPTION

Figure 1:
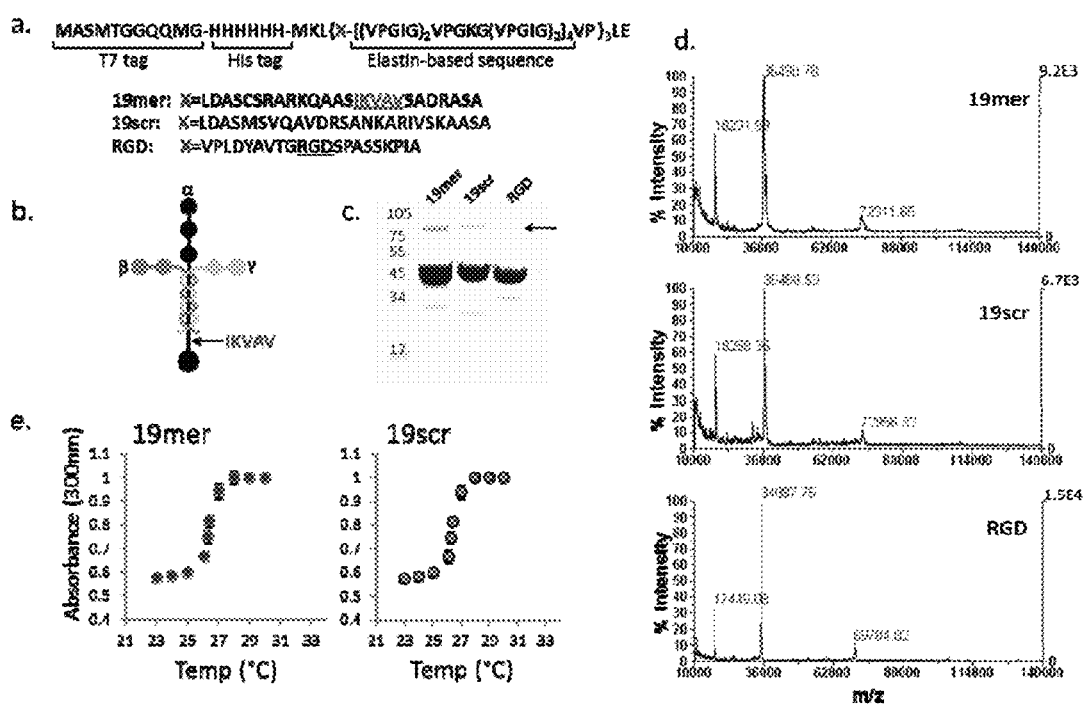
FIG. 1 illustrates artificial extracellular matrix (aECM) proteins according to some embodiments. a) Amino acid sequences of the aECM proteins generated according to some embodiments. (SEQ ID NOS: 5, 2, 6 and 7, respectively) b) Schematic representation of laminin protein comprised of three chains (αδγ), showing the location of the IKVAV (SEQ ID NO:1) sequence. c) Polyacrylamide gel stained with Colloidal Blue demonstrates the purity of aECM proteins. Arrow indicates protein dimers. d) MALDI-TOF mass spectra of aECM proteins. Signal at approximately 18 kDa is assigned to the doubly charged protein and the peak at approximately 73 kDa is assigned to the protein dimer. e) Absorbance at 300 nm was measured as a function of temperature to determine the transition temperature of the aECM proteins.

Methods for improving the survival of pancreatic progenitor or stem cells and methods for establishing or verifying the establishment of a population of pancreatic progenitor or stem cells are provided herein. The pancreatic progenitor or stem cells may be used for in vitro experiments related to diabetes or other pancreatic-related conditions or diseases; or may be expanded and differentiated to generate quantities of pancreatic endocrine cells (e.g., α-cells, β-cells, or acinar cells) in vitro that may be administered to a subject to treat a pancreatic-related condition or disease such as diabetes. Such treatments may be effective when a population of cells are used in a cell replacement therapy regimen to replace pancreatic endocrine cells that have been damaged, destroyed or are otherwise missing or malfunctioning.

Methods of Supporting and Improving Survival of Pancreatic β-Cell Progenitors

In some embodiments, a method of supporting and improving survival and/or differentiation of pancreatic β-cell progenitors in culture is provided. According to the embodiments described herein, the pancreatic progenitor cells—including pancreatic β-cell progenitors—are derived from an adult pancreas. As described in detail herein, adult pancreatic ductal cells include a population of multipotent or oligopotent progenitor or adult stem-cell like cells that can be isolated and cultured in vitro under certain cell culture conditions to induce differentiation of the cells into one or more populations of terminally differentiated progenitor cells or specific types of mature pancreatic cells including, but not limited to, acinar cells, endocrine cells or ductal cells.

In some embodiments, these cell culture conditions include a culture substrate that supports the development, growth and differentiation of the progenitor cells isolated from a pancreatic tissue sample. The culture substrate may include one or more suitable attachment components such as extracellular matrix (ECM) proteins or functional portions or fragments thereof. In some embodiments, the culture substrate includes an artificial ECM (aECM) protein that includes one or more functional portions or fragments of at least one ECM protein.

Fragments or portions of ECM proteins that maintain important functions of the ECM have been used as culture substrates in studies of cellular behavior and as scaffolds for use in regenerative medicine (Alberti et al. 2008; Khademhosseini et al. 2006; Wheeldon et al. 2011). For example, it has been shown that matrix-derived peptide sequences can be used to enhance survival of and insulin release from fully differentiated pancreatic β-cells encapsulated in poly(ethylene glycol) (PEG) hydrogels (Weber et al. 2007; Weber & Anseth 2008).

The effects of ECM proteins may vary based on the type of cell being cultured. As such, the one or more functional portions or fragments may be a portion or fragment of any ECM protein suitable for enhancing survival of pancreatic progenitor populations including, but not limited to, laminin, collagen, fibronectin, elastin, proteoglycans (e.g., heparin sulfate proteoglycans), and hyaluronic acid. A variety of extracellular matrix proteins, including laminin, collagen type IV, fibronectin, heparin sulfate proteoglycans and nidogen/entactin, are present in the microenvironments of pancreatic cells (Kragl & Lammed 2010). In the endocrine pancreas, insulin-expressing β-cells use VEGF-A to recruit endothelial cells, which form capillaries with a vascular basement membrane adjacent to the β-cells (Nikolova et al. 2006). Among the vascular basement membrane proteins, laminins were found to induce insulin gene expression and increase β-cell proliferation both in a MIN6 insulinoma cell line and in VEGF-A$^{-/-}$ islets (Nikolova et al. 2006). This effect was dependent on $β_1$-integrin receptor binding as determined by a blocking antibody assay (Nikolova et al. 2006). Both the survival and glucose-stimulated insulin secretion of isolated adult rat islets may be enhanced by culturing the cells on laminin (Pinske et al. 2006; Parnaud et al. 2006).

Therefore, according to the embodiments described herein, the methods for supporting and improving survival and/or differentiation of pancreatic β-cell progenitors in culture include a step of contacting a population of pancreatic progenitor cells with an aECM that includes a laminin component. As described in the Examples below, laminin enhances survival and differentiation of β-cell progenitors in culture. In some embodiments, the aECM laminin component includes an amino acid sequence comprising IKVAV (SEQ ID NO:1). In other embodiments, the aECM laminin component includes an amino acid sequence comprising X=LDASCSRARKQAASIKVAVSADRASA (SEQ ID NO:2).

In some embodiments, the aECM also includes an additional ECM protein component. Thus, in some embodiments, the aECM includes a portion or fragment of any suitable ECM protein including, but not limited to, laminin, collagen, fibronectin, elastin, proteoglycans (e.g., heparin sulfate proteoglycans), and hyaluronic acid. Although any suitable component may be used, elastin is preferred in some embodiments because it is soluble at 4° C. and insoluble at 37° C., whereas the majority of other proteins contain the opposite characteristics. Thus, including the elastin sequence should facilitate the purification of protein by thermal cycling, resulting in an inexpensive way for recombinant protein purification. In one embodiment, the aECM includes an elastin component which includes the following elastin-based sequence: [(VPGIG)$_2$VPGKG(VPGIG)$_2$]$_4$ (SEQ ID NO: 3).

The aECM protein may also include a T7 tag and a His tag. Thus, in some embodiments, the aECM protein includes the following amino acid sequence: MASMTGGQQMG-HHHHHH-MKL{X-Y-VP}$_3$LE (SEQ ID NO:4), wherein X is substituted with a laminin component and Y is substituted with a portion or fragment of an ECM protein. In certain embodiments, Y may by substituted with [(VPGIG)$_2$ VPG-KG(VPGIG)$_2$]$_4$ (SEQ ID NO: 3) such that the aECM protein includes the following amino acid sequence: MASMTG-GQQMG-HHHHHH-MKL{X-[(VPGIG)$_2$VPGKG(VP-GIG)$_2$]$_4$VP}$_3$LE (SEQ ID NO:5).

In some embodiments, X may be a laminin component that includes an amino acid sequence comprising IKVAV (SEQ ID NO:1), such as X=LDASCSRARKQAASIKVAVSADRASA (SEQ ID NO:2). Alternatively, the "X" component may also be substituted with an amino acid sequence that does not include a laminin component for use as a control to investigate the specificity of a cell response to the laminin component. For example, X may include a scrambled version of the IKVAV sequence (SEQ ID NO:1) (19scr), such as X=LDASMSVQAVDRSANKARIVSKAASA (SEQ ID NO:6), or may include a second protein that contains a fibronectin-derived RGD peptide sequence (RGD) such as X=VPLDYAVTGRGDSPASSKIPIA (SEQ ID NO:7) to control for effects of differential cell adhesion.

Methods of Establishing a Population of Pancreatic Progenitor Cells

In some embodiments, methods for establishing a population of pancreatic progenitor cells are provided. The population of pancreatic progenitor cells may include any pancreatic cell type or may have the potential for becoming any type of pancreatic cell including, but not limited to, a heterogeneous population of multipotent progenitor cells, a population of non-ductal progenitor cells, a population of acinar progenitor cells, a heterogeneous population of pancreatic endocrine progenitor cells (e.g., β-cells, α-cells, delta cells, gamma (or "PP") cells, and epsilon cells), or a population of pancreatic β-cell progenitors.

In some embodiments, the methods for establishing a population of pancreatic progenitor cells described herein include a step of isolating a population of cells from a pancreatic tissue sample that express CD133 and Sox9 (i.e., CD133$^+$/Sox9$^+$ cells).

Sox9, an HMG-box transcription factor, plays an important role in the embryonic formation of several tissues and organs, including the pancreas (Seymour et al. 2007). In mice, Sox9 is co expressed with Pdx1, a homeodomain-containing transcription factor (Gu et al. 2003), in multipotent progenitors of the early pancreatic epithelium (Seymour et al. 2007). After birth, expression of Sox9 becomes restricted to the ductal and centroacinar cells (Seymour et al. 2007; Furuyama et al. 2011). In humans, Sox9 is robustly expressed in embryonic pancreatic epithelium in patterns similar to those seen in mice (Piper et al. 2002). Whether adult human ducts express Sox9 was previously unknown.

CD133, also known as AC133 and prominin-1, was initially identified in hematopoietic stem and progenitor cells. It has since been used extensively as a marker for various stem cells from adult normal and cancerous tissues. Although CD133 is not expressed in most post-natal epithelia, it is expressed in pancreatic ducts (Lardon et al. 2008). CD133$^+$ cells isolated from embryonic or neonatal pancreas display progenitor cell activities in vitro (Hori et al. 2008; Oshima et al. 2007). However, the efficient differentiation of adult pancreatic CD133$^+$ cells into endocrine cells in vitro has not been possible, likely due to less-than-ideal culture conditions (Oshima et al. 2007). Although CD133 is expressed on cell surface of adult human pancreatic ductal trees (Lardon et al. 2008; Immervoll et al. 2008), some ductal cells express CD133 in the cytoplasm. This has led to the speculation by some researchers that CD133$^+$ duct cells may not be stem cells.

The population of pancreatic progenitor cells may be isolated by any suitable method including, but not limited to, FACS or any other method known to one skilled in the art that allows for the cells to be identified by expression of CD133 and Sox9. In some embodiments, pancreatic progenitor cells may be isolated using other cell surface markers, such as CD71, or any other markers that are capable of recognizing ductal cells. The population of cells may be derived from an adult pancreas of any subject, including those from humans, non-human primates, rodents (e.g., mouse, rat, rabbit guinea pigs, hamsters), bovine, porcine, canine, feline or any other animal. In some embodiments, the population of cells is derived from an adult human pancreas. In other embodiments, the population of cells is derived from an adult mouse pancreas. In further embodiments, the mouse pancreas may be derived from a wild type mouse or from a genetically modified mouse such as a Sox9-EGFP (Tg(Sox9-EGFP)209Gsat/Mmcd) mouse. In this case, the CD133$^+$/Sox9$^+$ cells may also be identified as CD133$^+$/Sox9-EGFP$^+$.

In some embodiments, the methods for establishing a population of pancreatic progenitor cells described herein include a step of culturing at least one of the isolated CD133$^+$/Sox9$^+$ cells with an effective amount of R-Spondin 1 to establish at least one single cell derived colony that comprises the population of pancreatic progenitor cells (also referred to as "colony cells" or "colony progenitor cells").

Roof plate-specific spondin 1 (R-Spondin 1) is part of the Wingless-int (Wnt) signaling pathway, and acts as a Wnt/beta-catenin signaling ligand. Wnt proteins are a family of secreted, lipid-modified proteins that are important to organ development (Peifer & Polakis 2000). They act by binding primarily to a family of G protein coupled cell surface receptors called Frizzled, as well as to co-receptors in the form of lipoprotein receptor-related proteins (Lrp). This ligand-receptor interaction triggers intracellular signaling events that activate the Dishevelled family of proteins. These Dishevelled proteins in turn disrupt a destruction complex—GSK-3beta, Anxin, and APC—that targets beta-catenin, a major effector of Wnt signaling. Upon activation of Dishevelled proteins, beta-catenin accumulates in the cytoplasm and is subsequently translocated into the nucleus, where it serves as a co-factor for Lef and/or TCF transcription factors and activates the transcription of downstream targets. Some of the most well-studied targets of beta-catenin include c-Myc, cyclin D1 and cyclin D2, which affect cell cycle progression.

R-Spondin 1 binds with high affinity to Lrp6 (Nam et al. 2006); this binding can be blocked by the Lrp6 inhibitor Dkk1 (Kim et al. 2005). R-Spondin 1 regulates sex determination (Parma et al. 2006), intestinal epithelium proliferation (Kim et al. 2005), and skin and osteoblast differentiation (Parma et al. 2006; Lu et al. 2008).

Pancreatic development is controlled by the sequential activation of certain transcription factors. Commitment of the un-specialized foregut region to the pancreatic lineage is promoted by the homeodomain-containing transcription factor, Pdx-1 (Jonsson et al. 1994) around embryonic day 8.5 (E8.5). The early Pdx-1-expressing cells are capable of giving rise to adult duct, acinar and endocrine cell lineages (Gu et al. 2002). In particular, their cell-fate choices are mediated by the subsequent expression of either neurogenin (Ngn) 3, a helixloop-helix transcription factor that drives the transition to endocrine cells, or of the pancreas-specific transcription factor (Ptf) 1a, which results in the development of acinar cells (Zhou et al. 2007).

Wnt signaling also exerts stage-specific effects during pancreatic development. Although over-expression of Wnt1 (Heller et al. 2002) or the constitutive activation of beta-catenin (Heiser et al. 2006) in early (E9) Pdx-1-expressing foregut cells results in agenesis of the pancreas, Wnt signaling enhances the growth and differentiation of more-developed (around E11.5) Pdx-1-expressing progenitor cells (Dessimoz et al. 2005). Further, Wnt signaling enhances the proliferation and maintains the function of mature endocrine β-cells in the adult pancreas (Fulifson et al. 2007; Wong et al. 2010). Together, these studies demonstrate that pancreatic cells are responsive to Wnt signaling at many stages of development.

In the studies described below, it was determined that R-Spondin 1 affects the function of adult murine ductal pancreatic stem cells in vitro. Adult murine pancreatic ducts were purified by sorting for CD133+Sox9-EGFP+ cells and three-dimensional clonogenic culture assays were used to detect colony-forming ductal stem cells. Self-renewal of these cells was measured through serial replating of colonies, and differentiation was assessed by the expression of lineage markers in single handpicked colonies. It was found that single adult murine ductal cells expressed Wnt receptors and Wnt downstream targets. Exogenous R-Spondin 1 enhanced, whereas Dkk1 (a Wnt antagonist) inhibited, the self-renewal of ductal stem cells. R-Spondin 1 also stimulated ductal stem cells to differentiate into duct cells as well as committed progenitors with restricted potential for endocrine and acinar lineages—the bi-potential progenitors. Finally, duct-derived progenitors may further differentiate and mature into glucose-responsive insulin-secreting β-cells in the absence of exogenous R-Spondin 1. Thus, R-Spondin 1 regulates the self-renewal and differentiation of pancreatic stem cells from adult mice in vitro. These results demonstrate the ability of single adult ductal pancreatic stem cells to repeatedly self-renew and to differentiate into functional β-cells in vitro.

In some embodiments described in detail below, the population of pancreatic progenitor cells may be cultured to induce differentiation of the progenitor cells. In vitro differentiation of adult pancreatic ductal cells to beta-like cells has been demonstrated under specific culture conditions (Bonner-Weir et al. 2000; Gao et al. 2003; Gao et al. 2005; Suarez-Pinzon et al. 2005). However, these studies generally started with a semi-purified population of cells, and the observed outcomes may have been a result of the effect of contaminating cell types. A conclusive demonstration of a progenitor and progeny relationship requires single-cell analysis (Ku 2008), such as that used by several groups to demonstrate that adult pancreatic cells from the centroacinar cell compartment, or cells that express c-Met or insulin, are capable of acinar and endocrine differentiation in two-dimensional attachment or "pancreatosphere" cultures (Suzuki et al. 2004; Seaberg et al. 2004; Smukler et al. 2011; Rovira et al. 2010). However, these studies have not specifically addressed whether single adult ductal cells possess stem cell activities in vitro.

Thus, as described in the Examples below, an in vitro, three-dimensional (3-D) assay was developed to demonstrate that single ductal pancreatic stem cells can self-renew and differentiate into multiple lineages in the absence of a mesenchymal niche. Culture components in this assay include, but are not limited to, methylcellulose, a biologically inert material that provides viscosity to the media, Matrigel or other suitable culture substrate, enriched for extracellular matrix proteins, and growth factors. This culture system simplifies studies of pancreatic stem cells, which may be an invaluable resource in regenerative medicine and the treatment of diabetes. A fraction of sorted single ductal cells built cystic structures containing cells that resembled duct, endocrine, and acinar cells. Electron microscopy and immunostaining analyses demonstrated that the differentiated duct-like cells displayed the correct polarity; RT-PCR analysis of individual colonies indicated that more than 70% expressed markers for duct, endocrine, and acinar lineages. Most colony-initiating cells are therefore multipotent. Single cells from approximately 80% of primary colonies formed secondary colonies, demonstrating self-renewal activities; R-Spondin 1 increased the self-renewal capacity of serially passaged clonal cells. Partial duct ligation in mice increased the ratio of non-colony-forming to colony-forming duct cells, demonstrating a dynamic response of ductal progenitors to injury.

In contrast to 2-D or suspension pancreatosphere assays (Suzuki et al. 2004; Seaberg et al. 2004; Smukler et al. 2011; Rovira et al. 2010), the 3-D colony assay allows for an even distribution and presentation of extracellular matrix components and growth factors to single cells in semi-solid media. It also permits the plating of large numbers (up to 25,000 per well) of sorted cells in 24-well plate and makes it easy to monitor the formation of individual colonies. Finally, the 3-D assay allows self-renewal, proliferation and differentiation to occur in the same culture plate. As a result, the 3-D assay is an efficient way to detect stem and progenitor cell activities from various populations of pancreatic cells.

The population of pancreatic progenitor cells that make up the single-cell derived colonies may be further cultured to induce differentiation, enrich, or establish a population of a particular type of progenitor cells. In some embodiments, the methods described herein may include steps for establishing a population of pancreatic endocrine progenitor cells. Such a method may include dissociating one or more single-cell derived colonies established as described above, to form a single cell suspension. The single cell suspension may then be replated and cultured—in the absence of R-Spondin 1—with a culture substrate that supports and/or enhances survival and differentiation of β-cell progenitors in culture. In some embodiments, the culture substrate may include one or more extracellular matrix proteins, a mixture of ECM proteins (e.g., matrigel) or fragments thereof, or one or more aECM. In some embodiments, the culture substrate is an aECM that includes a laminin component, such as those described above. For example, according to some embodiments, the aECM laminin component may include an amino acid sequence comprising IKVAV (SEQ ID NO:1). In other embodiments, the aECM laminin component may include an amino acid sequence comprising X=LDASCSRARKQAASIKVAVSADRASA (SEQ ID NO:2).

In certain embodiments, methods of identifying or verifying the establishment of a population of pancreatic progenitor cells is provided. After establishing one or more single cell derived colonies that comprise a population of pancreatic progenitor cells as discussed herein, the colony cells may be analyzed to detect the expression of one or more nucleic acid or protein markers that are indicative of pancreatic progenitor cells. Expression of the markers may be accomplished by any suitable method known in the art, including, but not limited to, PCR methods, RT-PCR methods, microarray methods, proteomics or immunoassays (e.g., immunohistochemistry, immunocytochemistry, western blot, ELISA), sequencing methods, and mass spectrometry.

The one or more nucleic acid or protein markers that may be used to verify that a particular population of pancreatic progenitor cells may include, but are not limited to amylase, c-Met, c-peptide, CAII, CK7, CK19, CPA1, DCAMKL1, DCAMKL2, ghrelin, glucagon (GCG), glucokinase, Glut-2, HNF6, HNF1, insulin 1, insulin 2, integrin β1, MafB, mucin, Ngn3, Nkx6.1, Pax4, Pdx1, PPY, PCSK1, PCSK2, and somatostatin (SST). In some embodiments, the one or more nucleic acid or protein markers may be used to verify the establishment of a population of early pancreatic endocrine progenitor cells. In such embodiments, the nucleic acid or protein markers include, but are not limited to, Pdx1, Ngn3, Nkx6.1, Pax4 and NeuroD1. In other embodiments, the one or more nucleic acid or protein markers may be used to verify the establishment of a population of committed pancreatic endocrine or acinar progenitor cells ("Endo/Acinar"). In such embodiments, the nucleic acid or protein markers include, but are not limited to, insulin 1, insulin 2, glucagon, somatostatin, PPY, ghrelin, SST, c-peptide, and elastase 1.

In some embodiments, a population of pancreatic endocrine cells generated and established as discussed above may be enriched for a particular subset of endocrine cells. For example, the population may be enriched for β-cells. In such methods, the subset of endocrine cells may be isolated by any suitable method using an intracellular or membrane-associated marker that is indicative of β-cells including, but not limited to, glucokinase, PCSK1, PCSK2, diacylglycerol kinase beta (DGKB) and glycoprotein M6A (GPM6A). Any suitable method may be used to isolate and enrich cells including, but not limited to, FACS, affinity chromatography or any other methods known to one skilled in the art.

Cell Culture System: Reagents and Kits

In some embodiments, a cell culture system for use with the methods described herein is provided. Such a culture system may include one or more components, which are added to a culture vessel. The one or more components of the culture system include, among other things, a nutritive cell media component, one or more media supplement components, one or more culture substrate (or attachment substrate) components, and a population of pancreatic progenitor cells to be maintained, grown, differentiated, enriched, or otherwise cultured within the culture vessel.

Nutritive media components that may be used in the cell culture system in accordance with some embodiments may include, but are not limited to, DMEM; RPMI-1640; MCDB 131; MCDB 153; MDEM; IMDM; MEM; M199; McCoy's 5A; Williams' Media E; Leibovitz's L-15 Medium; Grace's Insect Medium; IPL-41 Insect Medium; TC-100 Insect Medium; cell-specific serum-free media (SFM) such as those designed to support the culture of, for example, keratinocytes, endothelial cells, hepatocytes, melanocytes, pancreatic cells; F10 Nutrient Mixture; F12 Nutrient Mixture; and any other suitable commercially available nutritive media, such as those available through Gibco/Life Technologies, Inc.; and Sigma. The nutritive media component may also include one or more additional components, such as indicating or selection agents (e.g., dyes, antibiotics, amino acids, enzymes, substrates and the like), filters (e.g., charcoal), salts, polysaccharides, ions, detergents, stabilizers, buffer salts (e.g., sodium bicarbonate).

Media supplement components that may be used in the cell culture system in accordance with some embodiments may include, but are not limited to, animal sera (e.g., fetal bovine, newborn calf and calf sera human sera, monkey sera, or other primate sera,), hormones (including sex steroid, corticosteroids, peptide hormones such as insulin, cytokines, neurotransmitters, lipids and extracts of animal tissues, and organs or glands Other media supplement components that may be used in the cell culture system in accordance with some embodiments may include, but are not limited to, a variety of natural or recombinant proteins (e.g., serum albumins, particularly bovine or human serum albumins; immunoglobulins and fragments or complexes thereof; aprotinin; hemoglobin; haemin or haematin; enzymes such as trypsin, collagenases, pancreatinin or dispase; lipoproteins; fetuin; ferritin; etc.); vitamins; amino acids and variants thereof (including, but not limited to, L-glutamine and cystine), enzyme co-factors; polysaccharides; salts or ions (including trace elements such as salts or ions of molybdenum, vanadium, cobalt, manganese, selenium, and the like); and other supplements and compositions that are useful in cultivating cells in vitro that will be familiar to one of ordinary skill. In some embodiments, the media supplements described above may be obtained through any suitable commercially available source (from Life Technologies, Inc. and Sigma Cell Culture). Alternatively, the media supplements described above may be isolated from their natural sources or produced recombinantly by art-known methods that will be routine to one of ordinary skill (see Freshney, R. I., *Culture of Animal Cells*, New York: Alan R. Liss, Inc., pp. 74-78 (1983), and references cited therein; see also Harlow, E., and Lane, D., *Antibodies: A Laboratory Manual*, Cold Spring Harbor, N.Y.: Cold Spring Harbor Laboratory, pp. 116-120 (1988)).

In some embodiments, the cell culture system includes a media supplement component that includes one or more growth factors that may induce or support pancreatic progenitor cell differentiation and commitment toward mature pancreatic β-cells include, but are not limited to, PI3K inhibitors (e.g., Wortmannin and LY294002); retinoic acid; conophylline; Wnt; hedgehog; R-Spondin-1; vascular endothelial growth factor-A (VEGF); Activin/bone morphogenetic protein (BMP), fibroblast growth factor (FGF), epidermal growth factor (EGF), and hepatocyte growth factor (HGF). In one embodiment, the a media supplement component includes R-Spondin-1.

Culture substrate components that may be used in the cell culture system in accordance with some embodiments may include, but are not limited to, one or more extracellular matrix (ECM) proteins suitable for enhancing survival of pancreatic progenitor populations including, but not limited to, laminin, collagen, fibronectin, elastin, proteoglycans (e.g., heparin sulfate proteoglycans), and hyaluronic acid; an enriched mixture of ECM proteins (e.g., matrigel) or fragments thereof; or one or more artificial ECM (aECM). In some embodiments, the culture substrate is an aECM that includes a laminin component, such as those described above. For example, according to some embodiments, the aECM laminin component may include an amino acid sequence comprising IKVAV (SEQ ID NO:1). In other embodiments, the aECM laminin component may include an amino acid sequence comprising X=LDASCSRARKQAASIKVAVSADRASA (SEQ ID NO:2).

The cell culture system components described above may be in the form of pre-made, ready-to-use aqueous reagents, in a concentrated reagent that may be diluted to working concentrations prior to use, or may be in a powdered form, that may be reconstituted to an aqueous reagent prior to use. Each of the components may be obtained separately, or in a set or one or more reagents.

The one or more cell culture system components or reagents described above may also be part of a kit. Such a kit may include one or more containers such as vials, test tubes, bottles, packages, pouches, drums, and other suitable containers. Each of the containers may contain one or more of the cell culture system components or reagents described above, or combinations thereof. Such cell culture system components or reagents may be hydrated or dehydrated. The reagents in the kit may, in accordance with the embodiments described herein, be sterile. In certain embodiments, the kit provides instructions for usage, such as concentration, dosage or application instructions for use with the methods described herein.

In one embodiment, a first container may contain, for example, a media supplement component such as R-Spondin-1. In another embodiment, a second container may contain, for example, a culture substrate component, such as an aECM laminin component that includes an amino acid sequence comprising IKVAV (SEQ ID NO:1). Additional cell culture system components may be contained in additional containers in kits in accordance with the embodiments described herein. In other embodiments, a kit may also contain, in one or more additional containers, one or more pancreatic progenitor cells (undifferentiated, differentiated or partially differentiated) such as those described herein. Such cells may be lyophilized, dried, frozen or otherwise preserved, in accordance with methods known in the art.

In certain embodiments, a kit may also include one or more reagents that may be used to determine or verify the type of cells present in a cell culture or identify differentiated cells in the culture system. Such reagents may include one or more antibodies or other agents that, in combination with a reporter, can be used to identify one or more nucleic acid or protein markers of pancreatic cell differentiation. The one or more nucleic acid or protein markers that may be used to verify that a particular population of pancreatic progenitor cells may include, but are not limited to, amylase, c-Met, c-peptide, CAII, CK7, CK19, CPA1, DCAMKL1, DCAMKL2, ghrelin, glucagon (GCG), glucokinase, Glut-2, HNF6, HNF1, insulin 1, insulin 2, integrin β1, MafB, mucin, Ngn3, Nkx6.1, Pax4, Pdx1, PPY, PCSK1, PCSK2, and somatostatin (SST). In some embodiments, the one or more nucleic acid or protein markers may be used to verify the establishment of a population of early pancreatic endocrine progenitor cells. In such embodiments, the nucleic acid or protein markers include, but are not limited to, Pdx1, Ngn3, Nkx6.1, Pax4 and NeuroD1. In other embodiments, the one or more nucleic acid or protein markers may be used to verify the establishment of a population of committed pancreatic endocrine or acinar progenitor cells ("Endo/Acinar"). In such embodiments, the nucleic acid or protein markers include, but are not limited to, insulin 1, insulin 2, glucagon, somatostatin, PPY, ghrelin, SST, c-peptide, and elastase 1.

Methods for Treating Diabetes

In certain embodiments, a population of pancreatic endocrine progenitor cells generated and established as discussed above may be used in a method for treating diabetes. In some embodiments, the methods of treating diabetes described herein may include a step of administering a therapeutically effective amount of pancreatic endocrine progenitor cells to a subject having Type I diabetes. The pancreatic endocrine progenitor cells that may be used in accordance with the methods described herein may be administered, by any suitable route of administration, alone or as part of a pharmaceutical composition. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the pancreatic endocrine progenitor cells may be directly injected into the subject's pancreas to replace damaged, denuded, inefficient or otherwise defective β-cells. In some aspects, the methods for treating diabetes may be a cell-replacement therapy method or a β-cell or islet transplant procedure.

The term "effective amount" as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of cells or related composition that will yield the most effective results in terms of efficacy of treatment in a given subject or population of cells. This amount will vary depending upon a variety of factors, including but not limited to the characteristics of the cells or compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in a related formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to the administration of cells or compound and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression or reversal of the condition, or some combination thereof. Treatment may also mean a prophylactic or preventative treatment of a condition.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Artificial Extracellular Matrix Protein Containing Laminin-IKVAV Sequence Supports Survival and Differentiation of Murine Postnatal Pancreatic β-Cell Progenitors In Vitro As described below, the response of pancreatic cells to elastin-based aECM proteins that include three copies of the laminin-derived IKVAV sequence (SEQ ID NO:1) (designated 19mer) (FIG. 1A) were investigated. The elastin-based sequences dominate the physical properties of the protein and facilitate its purification by thermal cycling through the lower critical solution temperature (LOST). The 19 amino acid residues that include the IKVAV sequence (SEQ ID NO:1) were obtained from the α-chain of laminin. To investigate the specificity of the cell response to the IKVAV sequence (SEQ ID NO:1), two additional proteins were designed (FIG. 1A). The first includes a scrambled version of the IKVAV sequence (SEQ ID NO:1) (designated 19scr). As a control for effects of differential cell adhesion, a second protein that contains a fibronectin-derived RGD peptide sequence (designated RGD) was designed.

Materials and Methods

Expression of aECM Proteins.

Cloning was performed in *E. coli* strain DH10B (Invitrogen, Carlsbad, Calif.). Bacteria transformation was accomplished with Z-competent *E. coli* transformation kits (Zymo Research, Irvine, Calif.). Restriction enzymes were obtained from New England Biolabs (Ipswich, Mass.). Ligations were performed with T4 DNA ligase (Roche, Indianapolis, Ind.). Plasmids were isolated with QIAprep kits (Qiagen, Valenica, Calif.). Final plasmid sequences were verified by restriction digestion and sequencing (Laragen, Culver City, Calif.).

DNA sequences encoding various aECM proteins were ligated into pET28 (Novagen, Madison, Wis.) and induced under control of a bacteriophage T7 promoter. Expressions were performed in *E. coli* strain BL21 (DE3) pLysS (Novagen). Overnight cultures were used to inoculate Terrific Broth (TB) medium supplemented with 50 μg/ml kanamycin and 100 μg/ml chloramphenicol (Sigma, St. Louis, Mo.). Cells were grown to optical density at 600 nm ($OD_{600}$) of 5 in a 10 L BioFlow 3000 fermenter (New Brunswick Scientific, Edison, N.J.) with oxygen and pH control as previously described [18, 19]. Induction was initiated at $OD_{600}$=5 by addition of 2.5 mM isopropyl-1-β-D-thiogalactopyranoside (IPTG). After 3 h the $OD_{600}$ was 10-15.

Purification of aECM Proteins.

Bacteria cells were pelleted by centrifugation (10,000 g, 15 min, 4° C.) and lysed in TEN buffer (10 mM Tris-HCL, 1 mM EDTA, 0.1 M NaCl, pH 8) supplemented with 50 μg/ml phenylmethylsulfonyl fluoride (Sigma) and 10 μg/ml each of ribonuclease A and deoxyribonuclease 1 (Sigma). Cells were lysed by a freeze-thaw cycle followed by sonication at 4° C. Lysates were centrifuged (35,000 g, 2 h, 4° C.), and the soluble fraction was adjusted to pH 9 in 1 M NaCl. Each thermal cycle consisted of a temperature shift to 37° C., followed by centrifugation (35,000 g, 2 h), resolubilization of the pellet in pH 9 water at 4° C., and centrifugation (35,000 g, 2 h). After three thermal cycles, aECM proteins were dialyzed in water at 4° C. and the product lyophilized. A solution of 0.25 mg/ml of protein was subjected to electrophoresis on a Novex 12% Bis-Tris polyacrylamide gel (Invitrogen), labeled with colloidal blue dye (Invitrogen) and imaged on a Typhoon 9400 molecular imager (GE Healthcare).

MALDI-TOF Mass Spectrometry.

Matrix assisted laser desorption ionization mass spectrometry (MALDI-MS) was performed on a Voyager DE-Pro MALDI TOF-MS (Applied Biosystems, Beverly, Mass.). Protein solutions at 30 mg/ml were added to matrix solution consisting of 10 mg/ml sinapinic acid in 0.07% trifluoroacetic acid and 30% acetonitrile. A matrix to protein ratio of 20:1 was used.

LCST Measurements.

Lower critical solution temperature measurements were performed at a protein concentration of 10 mg/ml in phosphate buffered saline (pH 7.4). Absorbance at 300 nm was measured on a DU7400 diode array UV-visible spectrophotomer (Beckman Coulter, Indianapolis, Ind.).

Pancreas Dissociation.

Pancreata were dissected from 8-day-old C57BL/6 mice, and dissociated with 4 mg/ml collagenase B (Roche, Indianapolis, Ind.) and 1000 U/ml deoxyribonuclease I (Calbiochem, Gibbstown, N.J.) at 37° C. for 20 min. Cells were washed twice with Dulbecco's PBS (Mediatech, Manassas, Va.) containing 0.1% bovine serum albumin (Sigma) and filtered through a 40 μm mesh to yield single cell suspensions.

Mouse Cell Culture.

The cells were cultured as previously described (Winkler et al. 2011, which is hereby incorporated by reference as if fully set forth herein). Briefly, cells were dissociated as described above and resuspended in cold culture medium containing Dmem/f12 (mediatech), 1% 1500 centipoise methylcellulose (Sinetsu Chemical, Tokyo, Japan), 50% conditioned medium from pancreatic-like cells differentiated from embryonic stem cells, 5% fetal bovine serum (Tissue Culture Biologicals, Seal Beach, Calif.), 10 mM nicotinamide (Sigma), 0.1 nM exendin-4 and 10 ng/ml human recombinant activin-δ (R&D Systems, Minneapolis, Minn.). Unless specified otherwise, aECM proteins were added at 100 µg/ml. Matrigel (BD Biosciences, Bedford, Mass.) was added at 5% VN. Cells were placed in 24-well Ultra-Low attachment plates (Corning Incorporated, Corning, N.Y.) at $1\times10^4$ cells/well and incubated at 37° C. with 5% $CO_2$ air. Quadruplicate wells were routinely plated and analyzed.

RNA Isolation, RT-PCR and Quantitative PCR Analysis.

Figure 5:
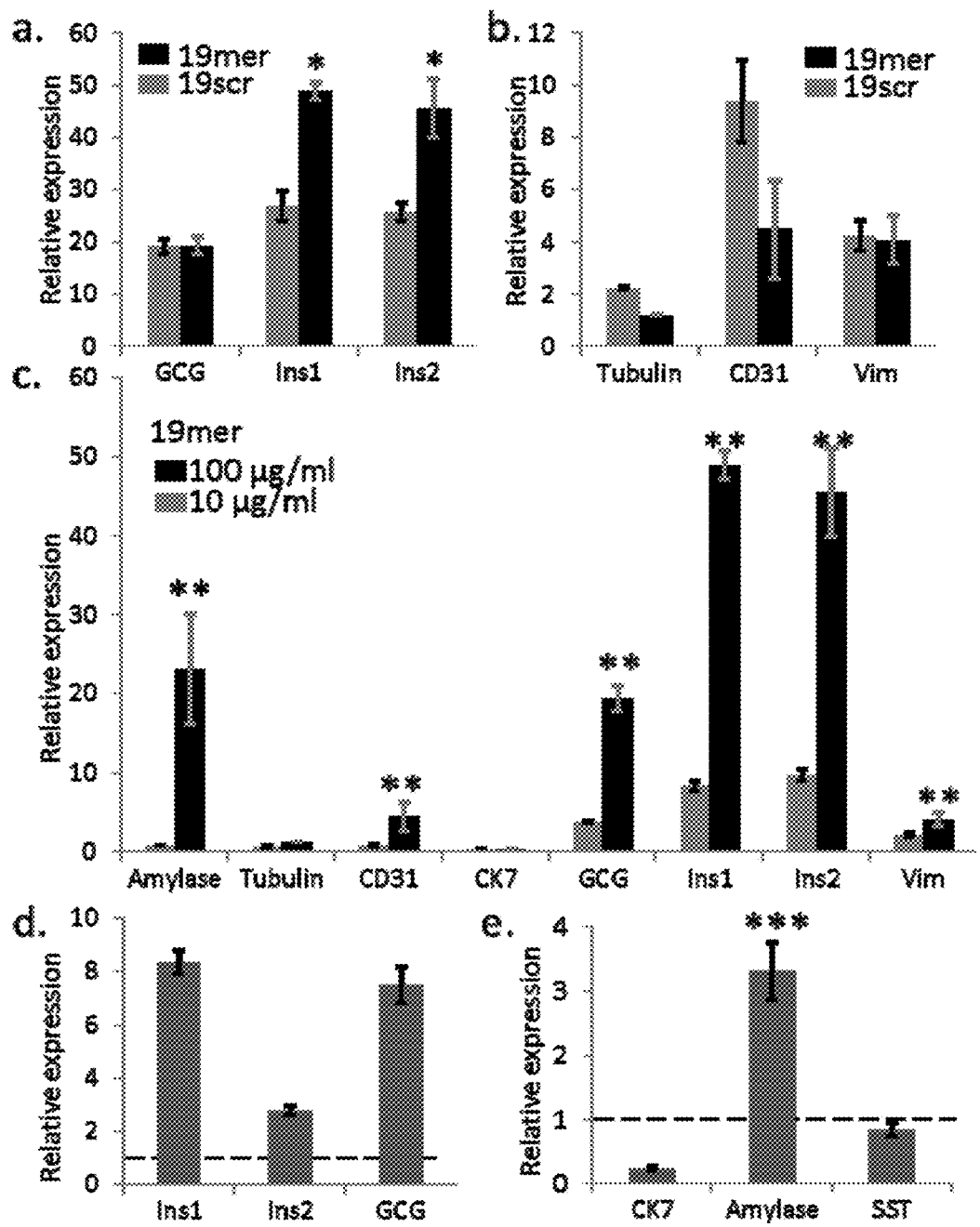
FIG. 5 is a series of graphs illustrating opposing effects of aECM proteins as compared to Matrigel in pancreatic cell culture. An artificial ECM protein with laminin-derived sequences (19mer) preferentially supported the survival of pancreatic endocrine and acinar cells, but not ductal cells. Single cells procured from postnatal pancreas were plated into semi-solid media containing Matrigel, 19mer or 19scr. Seven (a-c) or 25 (d-e) days post-plating, total cells were collected and gene expression analyzed by QRT-PCR. Gene expression levels were normalized to those supported by Matrigel (a-c and e) or to freshly isolated adult pancreatic cells (d). Cells in panels d and e were grown in the presence of 100 µg/ml 19mer. Error bars represent standard deviation. Markers represent endocrine (insulin 1 and 2 [Ins1, Ins2], glucagon [GCG], somatostatin [SST]), acinar (amylase 2a [Amylase]), ductal (CK7), neuronal (β3-tubulin [Tubulin]), endothelial (CD31), and mesenchymal (vimentin [Vim]) cells. This number is different from 19scr at $P<0.05$. This number is different from 10 µg/ml 19mer at $P<0.05$. *This number is different from Matrigel control at $P<0.05$.

Total RNA was extracted by using RNeasy Micro Kits (Qiagen). Reverse transcription was performed using QuantiTect Reverse Transcription Kits (Qiagen). The cDNAs of interest were amplified with Taqman probes (Applied Biosystems) and reaction buffer PerfeCTa FastMix (Quanta Biosciences, Gaithersburg, Md.) on an ABI 7900HT Fast Real-time PCR System (Applied Biosystems). All samples were tested in duplicate and β-actin was used as an internal control to calculate relative ($\Delta C_T$) gene expression among samples in the same PCR run. Values in FIG. 5 were further normalized to that obtained from freshly isolated adult pancreatic cells (panel d) or from Matrigel-treated cells (rest of panels). Abbreviations for gene markers: GCG, glucagon; Ins, insulin; Tubulin, β3-tubulin; Vim, vimentin; Amylase, amylase 2a; CK7, cytokeratin 7; SST, somatostatin; HNF6, hepatocyte nuclear factor 6.

Microfluidic QRT-PCR Analysis on Single Handpicked Colonies.

Individual colonies were handpicked and analyzed using the BioMark™ 48.48 Dynamic Array System (Fluidigm, South San Francisco, Calif.) according to the manufacturer's protocol. Threshold cycle ($C_T$) was determined from fluorescence intensity by the BioMark PCR Analysis software. $\Delta C_T$ was calculated relative to β-actin, similar to the QRT-PCR analysis.

Colony Counts.

Colonies were scored visually on an inverted optical microscope (with a 10× objective lens) as previously described (Winkler et al. 2011, which is hereby incorporated by reference as if fully set forth herein). Due to the 3-dimentional feature of the media, the colonies will appear at different focal points. Thus, an adjustment of the focus for each colony may be required during observation by light microscopy. A grid is attached under the 24-well plate when counting in order to avid registering the same colony twice.

Whole-Mount Immunofluorescent Staining and Confocal Microscopy.

Colonies were handpicked, pooled, placed in round-bottom 96-well plates, and fixed with 4% paraformaldehyde (Pierce, Rockford, Ill.) in PBS for 30 min. After washing twice with PBS, cells were permeabilized with 0.1% Triton-X100 (Pierce) for 10 min and then washed again with PBS. Non-specific binding sites were first blocked by incubation overnight with Protein Block Serum-Free solution (Dako, Carpinteria, Calif.) at 4° C., followed by staining with primary antibody (rabbit anti-human Glucagon or C-peptide serum [Dako]) at 1:75 dilution in blocking solution for 24 h at 4° C. Rabbit IgG was used as an isotype control. After washing, Cy5-conjugated goat anti-rabbit antibody (Jackson Immunology Research Labs, West Grove, Pa.) (1:100) was added and incubated at room temperature for 4 h. After washing, colonies were resuspended in 50 µg/ml DPPI in PBS for 30 min prior to imaging on a glass-bottom petri dish (MatTek, Ashland, Mass.). Confocal imaging was performed on a LSM510 Meta NLO microscope (Zeiss) with 2-photon capability. DAPI was excited at 700 nm for 2-photon excitation.

Statistical Analysis:

Student's t-test was used to determine statistical significance.

Results and Discussion

Figure 2:
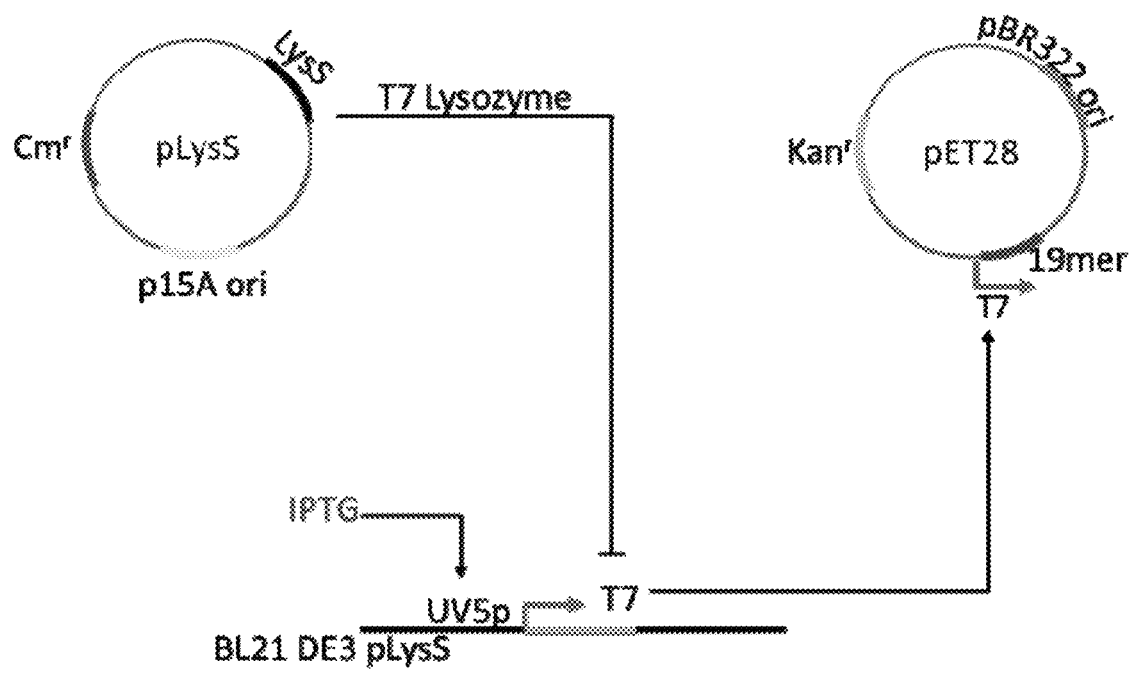
FIG. 2 is a schematic illustrating an inducible expression system used for the production of aECM proteins in bacteria. The genome of the *E-coli* strain, BL21 (DE3) pLysS, contains a gene for bacteriophage T7 polymerase under the control of the UV5p promoter. In the absence of the inducer IPTG, the endogenous T7 polymerase is inhibited by the T7 lysozyme expressed by an episomal plasmid, pLysS, in the bacteria. After addition, IPTG binds to UV5p promoter and activates production of T7 polymerase, which subsequently triggers the expression of aECM gene, such as the 19mer shown, located in a pET28 plasmid.
Figure 3:
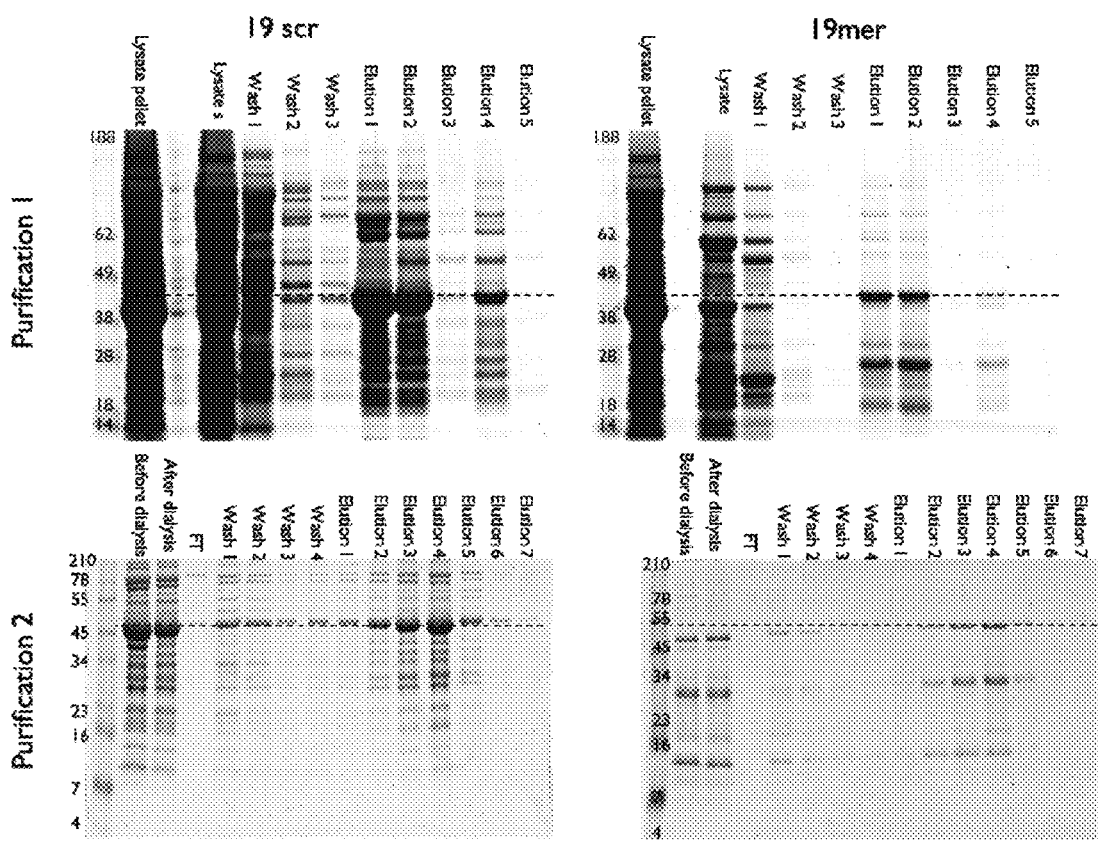
FIG. 3 is a series of gels illustrating efficient purification of aECM proteins using cold-hot temperature cycles. In purification method 1 (upper panels), the nickel-nitrilotriacetic acid (Ni-NTA) resin affinity chromatography was used to enrich 19scr and 19mer proteins, because their N-terminal polyhistidine-tag can bind to the Ni-NTA resin. In purification method 2 (lower panels), temperature cycling based on the lower critical solution temperature (LCST) of the 19scr and 19mer proteins was also effective in purifying these proteins. Dotted lines show the position of the 19scr and 19mer proteins on polyacrylamide gels stained with Coomassie Blue. Since temperature cycling is more cost-effective, aECM proteins are often based on this method.

The aECM proteins were expressed in *E. coli* strain BL21 (DE3) pLysS by using an inducible pET28 expression vector (FIGS. 2 and 3). After three rounds of thermal cycling, each aECM protein was obtained in pure form, as shown by gel electrophoresis (FIG. 1C). The molecular weight of each protein was verified by MALDI-TOF mass spectrometry (FIG. 1D). The LCST was approximately 27° C. in phosphate buffered saline at a protein concentration of 10 mg/ml (FIG. 1E).

Figure 4:
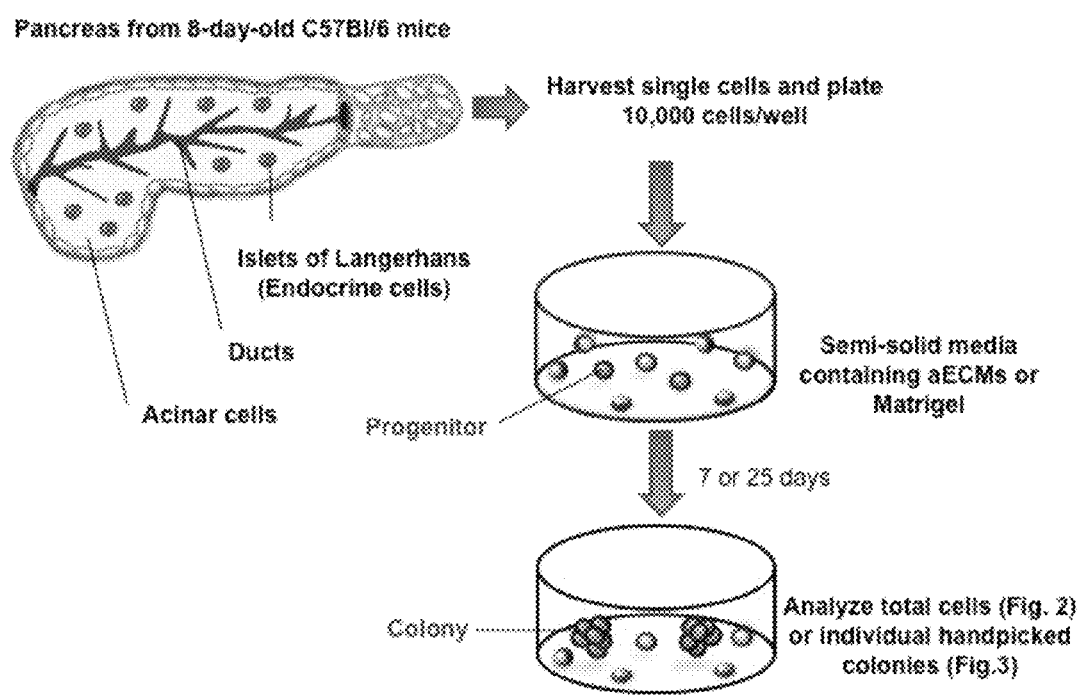
FIG. 4 is a schematic illustrating a mouse cell culture assay according to some embodiments. The assay allows the survival and differentiation of single cells. Progenitor cell activities are detected by their ability to form colonies in semi-solid media, which restrict the movement of single progenitor cells while permitting them to survive, proliferate and/or differentiate in culture. Viscosity of the media is provided by methylcellulose, a biologically inert material. Detailed methodology is described below and in Winkler et al. 2011, which is hereby incorporated by reference as if fully set forth herein.

To test the effects of aECM proteins, the postnatal pancreas was selected for study, which is—a rich source of both progenitor cells (Bonner-Weir 2000; Herbach et al. 2011) and differentiated cells. Dissociated cells were harvested from pancreas and plated in 3-dimensional cultures containing semi-solid media that permit the survival, proliferation and/or differentiation of single cells (FIG. 4) (as described above, procedure is similar to Winkler et al. 2011, which is hereby incorporated by reference as if fully set forth herein). The effects of these materials were compared to those of Matrigel™ which is a commercial source of crude ECM components.

Cells were grown in the presence of either Matrigel (5%), 19mer or 19scr (100 µg/ml each) proteins for 7 days, and expression of various marker genes was analyzed by quantitative (Q) RT-PCR. The level of gene expression was first analyzed relative to an internal control, the housekeeping gene β-actin. Subsequently, gene expression levels from cells supported by aECM proteins were further normalized to those supported by Matrigel. Compared to Matrigel, both the 19mer and 19scr proteins enhanced expression of endocrine (glucagon⁺ alpha cells and insulin⁺β-cells), neuronal (β3-tubulin), endothelial (CD31) and mesenchymal (vimentin) cell markers (FIGS. 5A and 5B). Compared to 19scr, the 19mer protein enhanced the levels of insulins 1 and 2 (FIG. 5A), suggesting a specific effect of the IKVAV sequence (SEQ ID NO:1) to support the survival of single β-cells or the differentiation of their progenitors.

Next, the dose-dependent response of dissociated pancreatic cells to the 19mer protein was investigated. There was a positive correlation between the concentration of 19mer protein and expression of amylase 2a (an acinar cell marker), CD31, glucagon, insulins 1 and 2, and vimentin (FIG. 5C). In contrast, the level of ductal cell marker, CK7, was lower in cells supported by the 19mer protein compared to Matrigel. Taken together, these findings indicate that in short-term cultures and in contrast to Matrigel, the 19mer protein enhances survival or differentiation away from ductal cells, and that the IKVAV sequence (SEQ ID NO:1) specifically increases insulin expression.

Next the long-term effect of the 19mer protein was investigated using 25 day cultures. QRT-PCR analysis showed increased levels of insulins 1 and 2 and glucagon above those characteristic of freshly isolated adult pancreatic cells (FIG. 5D). Consistent with the short-term culture results and compared to Matrigel, the ductal cell marker CK7 was down-regulated. The expression of the endocrine delta cell marker somatostatin (SST) was retained and the acinar marker amylase 2a was minimally up-regulated by the 19mer protein (FIG. 5E). Taken together, these results indicate that, in long-term culture, the 19mer protein preferentially supports the survival of alpha and β-cells, and to lesser extent acinar cells, but in contrast to Matrigel (which preferentially supports the survival and differentiation of ductal cells), the 19mer protein does not support ductal cells.

Figure 6:
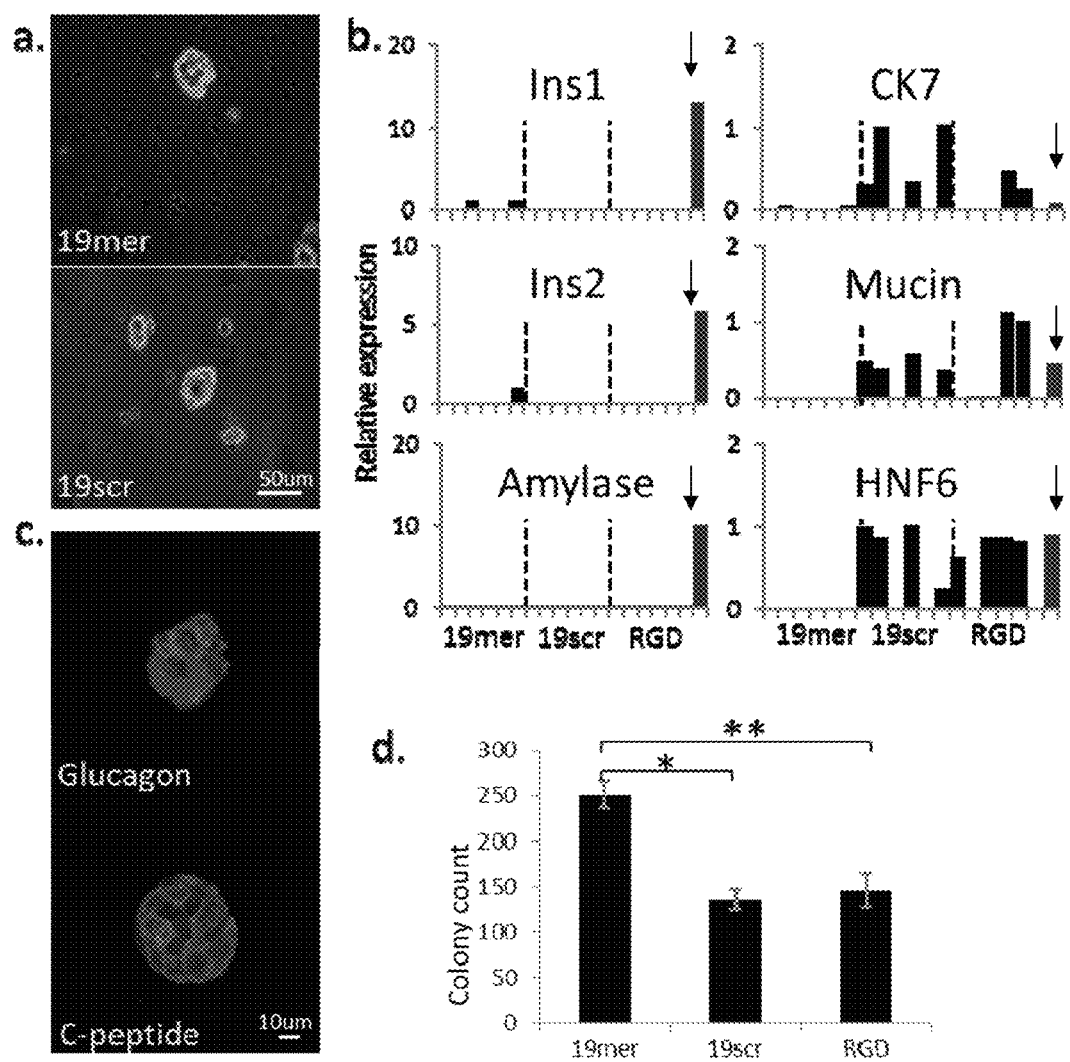
FIG. 6 shows that pancreatic progenitor cells can survive and differentiate when in contact with aECM proteins. Differentiation of beta-cell progenitor cells is best supported by aECM protein with laminin-derived sequences (19mer). a) Photomicrographs of single cell-derived colonies (7-day-old) grown in the presence of designated aECM proteins. b) Microfluidic QRT-PCR analysis of individually handpicked 8-day-old colonies grown on designated aECM proteins. Expression is relative to the internal control β-actin. Bars indicated by an arrow represent the expression levels from positive control postnatal pancreatic cells. Each black bar (without arrow) represents expression level of the indicated gene by 1 colony (n=6 from each group). c) Whole-mount immunofluorescent staining of handpicked 8-day-old colonies grown in the presence of the 19mer. Nuclei are stained with DAPI in blue. d) Survival of pancreatic progenitor cells is enhanced by the 19mer, as indicated by the higher number of single cell-derived colonies. Data represent the mean and standard deviation of the number of 8-day-old colonies in quadruplicate wells.*$P=1.27\times10^{-4}$; **$P=2.31\times10^{-5}$.
Figure 8:
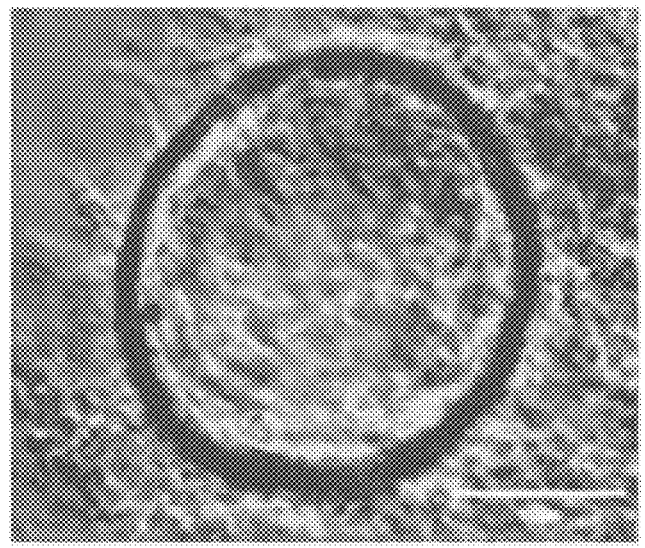
FIG. 8 is a photomicrograph of a 7-day-old cystic colony in culture. Pancreata from 8-day-old mice were dissociated into single suspension and cultured in a semi-solid medium containing Matrigel as previously described by Winkler et al. 2011, which is hereby incorporated by reference as if fully set forth herein. Under a light, phase-contrast microscope, this 3-dimensional cystic structure indicates ductal cell differentiation. Bar=100 µm.

To investigate the effects of aECM proteins specifically on progenitor cells, single cell-derived colonies, whose lineage composition and number would indicate their lineage potential and survival, respectively, were analyzed. Single cells harvested from postnatal pancreas were plated in a clonogenic assay (FIG. 4) in the presence of various aECM proteins. After 7 days in culture, light-reflective colonies with diameters ranging from 20 to 60 μm were observed (FIG. 6A). In the control culture containing Matrigel, cystic colonies (FIG. 8) typical of ductal cell morphology were observed. Such ductal colonies have been characterized in prior studies, and they are formed in cultures initiated with purified adult human (Sonner-Weir et al. 2000; Gao et al. 2003) or mouse (Schreiber et al. 2004; Jin et al. 2012) ductal cells in the presence of Matrigel.

To analyze lineage composition, individual 8-day-old colonies that showed morphologies consistent with those in FIG. 6A were handpicked and subjected to microfluidic QRT-PCR analysis (FIG. 6B). All values were normalized to β-actin and compared to those obtained from freshly isolated postnatal pancreas cells. Among the single colonies supported by the 19mer protein, 2 out of 6 expressed insulin 1 or 2, and none expressed ductal (CK7, mucin1, and HNF6) or acinar (amylase 2a) cell markers. In contrast, 19scr- and RGD-supported colonies did not express insulins 1 or 2, but 4 out of 6 colonies from each group expressed at least one of the three ductal markers. These results demonstrate that the 19mer protein specifically supports differentiation of β-cell progenitors. Alternatively, the 19mer protein may divert lineage commitment to β-cells from a bi-potential progenitor that could otherwise differentiate toward both ductal and β-cell lineages. Expression of glucagon was not detected in any of the 6 colonies supported by the 19mer protein, which may suggest a lower prevalence of alpha- than beta-cell progenitors in postnatal pancreas.

Figure 7:
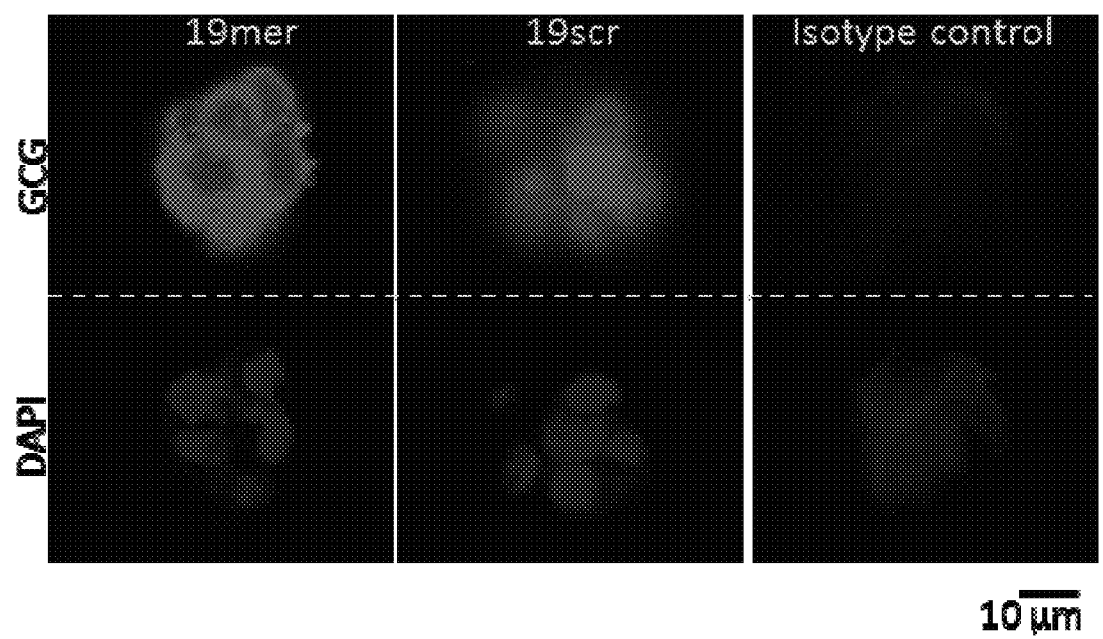
FIG. 7 shows immunofluorescent staining of glucagon in colonies developed from cultures containing 19mer or 19scr proteins. DAPI is indicative of nuclei staining. The isotype control antibody staining shows low background of secondary Cy5-conjugated anti-rabbit antibody.

To examine protein expression and to ensure glucagon-expressing colonies could be observed, whole-mount immunostaining and imaged colonies by confocal fluorescence microscopy were used. C-peptide was used as a surrogate marker for de novo synthesized insulin to distinguish it from exogenous recombinant insulin (Rajagopal et al. 2003), which was present in the culture media. Colonies that positively stained for either glucagon or C-peptide were observed (FIG. 6C). The staining was specific; incubation with isotype control antibody did not yield a positive signal. The staining patterns of glucagon or C-peptide were cytoplasmic, consistent with the expected locations of these proteins as secretory hormones (FIG. 7). Together, these results indicate that the 19mer protein supports differentiation of both alpha and β-cell progenitors. Comparison of colony-forming frequency among cultures containing various aECM proteins revealed that the 19mer protein best supports the overall survival of progenitor cells (FIG. 6D).

In summary, an elastin-based aECM protein bearing a laminin-derived IKVAV sequence (SEQ ID NO:1) was developed, which supports survival and differentiation of β-cell progenitors in culture. The observed effects may be due to better survival or selection for beta versus ductal cell lineages. Appropriately designed aECM proteins may eventually enable expansion and differentiation of stem and progenitor cells to be used in regenerative medicine.

Example 2: Single CD133⁺Sox9⁺ Ductal Pancreatic Stem Cells from Adult Mice Build Multi-Lineage Cystic Structures In Vitro To explore whether adult pancreatic ducts can serve as a source of endocrine cells in vitro, the studies described below were conducted to 1) identify and enrich murine adult pancreatic ductal cells expressing Sox9 and CD133 through the use of fluorescent activated cell sorting (FACS), and 2) test their self-renewal and differentiation potential as single cells using a three-dimensional, mesenchymal-cell-free, colony assay developed in Winkler et al. 2011, which is hereby incorporated by reference as if fully set forth herein. These results show that a small fraction of single murine ductal cells, identified as CD133$^+$Sox9-EGFP$^+$, give rise to colonies of cystic morphology containing mostly ductal-like cells with limited and confined areas of acinar or endocrine differentiation. Serial replating experiments demonstrate the self renewal capacity of individual progenitors from the colonies. Preliminary studies using adult human cadaveric pancreas demonstrated that CD133$^+$CD49f$^{low}$ cells are enriched for ductal cells and are capable of forming individual colonies, although they do so less efficiently than murine cells. Together, these results demonstrate that murine adult ductal cells contain stem cells that can self-renew and differentiate in vitro. These results pave the way for the studies of ex vivo proliferation and differentiation of these stem cells towards the endocrine lineage as described in Example 3 below.

Materials and Methods

Animals.

Sox9-EGFP (Tg(Sox9-EGFP)209Gsat/Mmcd) mice (Gong et al. 2003) were obtained from the Mutant Mouse Regional Resource Centers (MMRRC) and maintained on a CD1 genetic background. C57Bl/6 mice were purchased from Charles River Laboratory, Wilmington, Mass. All mice were maintained under specific pathogen-free conditions, and animal experiments were conducted according to the Institutional Animal Care and Use Committee at the City of Hope and University of California, San Diego.

Human Adult Pancreatic Cells.

The use of adult human semi-dissociated pancreatic tissues, obtained after islets were removed by the Southern California-Islet Cell Resource Center (SC-ICRC), was approved by the Institutional Review Board of the City of Hope. The tissues were stored in UW solution on ice for up to 5 days before further dissociation, staining and sorting. A total of 44 tissues, with a donor age of 43.2±13.6 years, were analyzed.

Preparation of Single Cell Suspensions.

Murine pancreata were dissected, cleared of fat tissue under a dissecting microscope, and rinsed thrice in cold D-PBS containing 0.1% bovine serum albumin (BSA), and 1× penicillin and streptomycin (PBS/BSA). Whole pancreas was chopped using spring scissors for approximately 2 min or till it is finely minced. The triturated tissue was transferred to a 15 ml conical tube, washed once, resuspend in PBS/BSA containing collagenase B (4 mg/mL per pancreas) and DNase I (2000 U/mL per pancreas), and incubated at 37° C. for 20-30 min to yield single cell suspension. To hasten the digestion, tissue was gently disrupted every 5-10 min using a 1-mL Gilson pipettman. The single cell suspension was then washed twice in cold PBS/BSA supplemented with 2000 U/mL DNase I, which is used to prevent reaggregation of dissociated cells. Human pancreatic clusters were washed thrice before dissociation into single cell suspension using collagenase B as described for murine cells.

Quantitative RT-PCR.

Total RNAs extraction and reverse transcription were as described (Chen et al. 2011). The Taqman probes and their catalog numbers used for murine cells were as follows: Amylase 2A, Mm02342487_g1; CD133, Mm00477115_m1; CD45, Mm01293577_m1; Glucagon, Mm 00801712_ml; Insulin 1, Mm01259683_g1; Insulin 2, Mm 00731595_gH; CK7, Mm00466676_m1; Ngn3, Mm00437606_s1; Pdx1, Mm 00435565_m1; Sox9, Mm 00448840_m1. β-actin (Mm 00607939_s1) was used as an internal control for normalization. Probes for human cells are listed below in Table 1. Duplicated samples were used in all analyses.

TABLE 1

List of murine and human Taqman probes used for microfluidic RT-PCR analysis.

| Murine Gene | Assay ID from ABI | Human Gene | Assay ID from ABI |
| --- | --- | --- | --- |
| B-Actin | Mm 00607939_s1 | CK7 | Hs00818825_m1 |
| B2 microglobulin | Mm 00437762_m1 | CA-II | Hs00163869_m1 |
| Cyclophilin G | Mm01328875_m1 | Mucin1 | Hs00159357_m1 |
| CK7 | Mm 00466676_m1 | Integrin 1 | Hs00559595_m1 |
| CA II | Mm 00501572_m1 | PDX1 | Hs00236830_m1 |
| Mucin 1 | Mm00449604_m1 | NgN3 | Hs01875204_s1 |
| Integrin B1 | Mm01253230_m1 | Sox9 | Hs00165814_m1 |
| NgN3 | Mm00437606_s1 | CD133 | Hs01009259_m1 |
| Sox9 | Mm 00448840_m1 | C-met | Hs00179845_m1 |
| CD133 | Mm00477115_m1 | DCAMKL1 | Hs00178027_m1 |
| ALDH1a1 | Mm00657317_m1 | DCAMKL2 | Hs01099791_m1 |
| C-Met | Mm01156972_m1 | PCSK1 | Hs01026107_m1 |
| DCAMKL-1 | Mm00444950_m1 | PCSK2 | Hs01037347_m1 |
| DCAMKL-2 | Mm01223146_m1 | Glut-2 | Hs00165775_m1 |
| Pcsk1 | Mm00479023_m1 | Insulin | Hs00355773_m1 |
| Pcsk2 | Mm00500981_m1 | Glucagon | Hs00174967_m1 |
| Insulin 1 | Mm01259683_g1 | PPY | Hs01078030_m1 |
| Insulin 2 | Mm 00731595_gH | Somatostatin | Hs00356144_m1 |
| Glucagon | Mm 00801712_m1 | Ghrelin | Hs00175082_m1 |
| PPY | Mm 00435889_m1 | CPA1 | Hs01056157_m1 |
| Somatostatin | Mm 00436671_m1 | Amylase 2A | Hs00420710_g1 |
| Ghrelin | Mm 00445450_m1 | HNF1b | Hs01001602_m1 |
| Amylase 2A | Mm02342487_g1 | CK19 | Hs00761767_s1 |
| Elastase 1 | Mm00712898_m1 | Nkx6.1 | Hs00232355_m1 |
| CPA1 | Mm 00465942_m1 | HNF6 | Hs00413554_m1 |
| Pdx1 | Mm 00435565_m1 | | |
| CK19 | Mm00492980_m1 | | |
| Pax4 | Mm 01159036_m1 | | |
| Nkx6.1 | Mm 00454962_m1 | | |
| MafB | Mm00627481_s1 | | |

Flow Cytometry and Cell Sorting.

Murine or human pancreatic single-cell suspensions were first incubated with anti-mouse CD16/32 (10 μg/mL; BioLegend, San Diego, Calif.) or human purified IgG, respectively, for five minutes on ice to diminish nonspecific binding. Biotin—conjugated anti-mouse CD133 (5 μg/mL; eBioscience, San Diego, Calif.) or the control biotin-conjugated rat IgG1 isotype (5 μg/mL; eBioscience) antibodies were added and cell incubated on ice for 20 min. After washing twice, cells were incubated with streptavidin labeled allophycocyanin (2 μg/mL; BioLegend) on ice for 15 min. Cells were washed twice, resuspended in PBS/BSA/DNase I containing DAPI (0.2 μg/ml), filtered through a 20-μm mesh, and kept on ice before flow cytometry analysis or sorting. When human cells were used, FITC-conjugated anti-human CD49f antibody (BioLegend) was added at the same time as biotin-conjugated anti-human CD133 antibody (clone 293C3, Miltenyi Biotec, Auburn, Calif.). Flow cytometry was performed using either an Accuri Cytometer and software (Accuri Cytometers Inc, Ann Arbor, Mich.) or a CyAn™ ADP 9 color (Beckman Coulter, Brea, Calif.) with FlowJo software (TreeStar, Inc, Ashland, Oreg.). Cell sorting was performed on a MoFlow™ MLS (Beckman Coulter). All analyses included an initial gating of forward and side scatters to exclude cell debris, followed by exclusion of dead cells that show high levels of DAPI staining.

Cell Culture and In Vitro Colony Assay.

Cells were cultured in methylcellulose-based colony culture medium as previously described (Ku et al. 2007; Winkler et al. 2011). In short, 1 ml cold culture mixture contained DMEM/F12 media, 0.9% 1,500 centipoise (high-viscosity) methylcellulose (Sinetsu Chemical, Tokyo, Japan), 5% Matrigel, 50% condition media from embryonic stem cell derived-pancreatic like cells, 5% fetal calf serum (FCS), 10 mmol/l nicotinamide (Sigma, St. Louis, Mo.), 10 ng/ml human recombinant activin-βB (R&D Systems, Minneapolis, Minn.), 0.1 nmol/l exendin-4, and 1 ng/ml vascular endothelial growth factor-A (VEGF) (R&D). Cells were plated in 24-well ultralow protein-binding plates and incubated in a humidified 5% CO2 atmosphere. R-Spondin 1 (R&D) was used at 750 ng/mL and added on day 7 postplating.

Microfluidic RT-PCR Analysis.

Microfluidic RT-PCR was performed using the BioMark™ 48.48 Dynamic Array system (Fluidigm, South San Francisco, Calif.). Single handpicked colonies were collected in 10 μl reaction buffer, followed by pre-amplification (14 cycles) according to manufacturer's instructions (Fluidigm). Amplified cDNA was loaded onto a 48.48 Dynamic Array using the NanoFlex IFC controller (Fluidigm). Threshold cycle (Ct), as a measurement of fluorescence intensity, was determined by the BioMark PCR analysis software (Fluidigm) and expressed as a heat map. All reactions were performed along with negative (buffer) and positive (adult pancreatic cell) controls in all experiments. Taqman probes used in this study are listed in Table 2 below. References for cell markers that were not listed in the main text are: CK7, ducts (Bouwens 1998); DCAMKL1 and DCAMKL2, progenitor cells (May et al. 2010); PCSK1 and PCSK2, mature endocrine cells (Malide et al. 1995; Furuta et al. 1997; Piper et al, 2004; Wang et al. 2007).

TABLE 2

List of antibodies used for Histology & Immunohistochemistry.

| Antigen | Source | | Dilution |
| --- | --- | --- | --- |
| Primary Antibodies | | | |
| | Species | | |
| Sox | Rabbit | Chemicon | 1:1000 |
| Pdx1 | Guinea Pig | C. Wright, Vanderbilt | 1:10,000 |
| Integrin beta-1 | Rat | Chemicon | 1:500 |
| Glucagon | Mouse | Sigma | 1:5000 |
| Insulin | Guinea Pig | Dakocytomation | 1:1000 |
| C-peptide | Rabbit | Cell Signaling | 1:500 |
| Amylase | Rabbit | Sigma | 1:500 |
| GFP | Rat | C. Kioussi, Oregon State University | 1:1000 |
| Osteopontin | Goat | R&D Systems | 1:1000 |
| DBA | (Biotinylated) | Vector Laboratories | 1:500 |
| CD133 | Rat | ebiosciences | 1:1000 |

TABLE 2-continued

List of antibodies used for Histology & Immunohistochemistry.

| Antigen | Source | | Dilution |
|---|---|---|---|
| Mucin-1 | Armenian hamster | Lab Vision | 1:200 |
| Cytokeratin 19 | Rabbit | DAKO | 1:1000 |

Secondary Antibodies

| | Conjugation | | |
|---|---|---|---|
| Rabbit/Goat/Mouse/ Guinea Pig/Rat | Alexa-488 | Invitrogen | 1:2000 |
| Rabbit/Goat/Mouse/ Guinea Pig | Cy3 | Jackson ImmunoResearch | 1:2000 |
| Rabbit/Goat/Mouse/ Guinea Pig/ Armenian Hamster | Cy5 | Jackson ImmunoResearch | 1:500 |

Electron Microscopy.

Single colonies were fixed in Karnovsky's fixative at 4° C. overnight. The colonies, placed in round bottom 96-well plate under direct visualization of a microscope to facilitate rinsing without losing them, were washed thrice with Cacod buffer. Colonies were transferred to an Ependorf tube, incubated with 1% osmium tetroxide in 0.1M Cacod buffer for 30 min, washed thrice, dehydrated, embedded in eponate, and processed for transmission electron microscopy.

Single Cell Manipulation.

Freshly sorted cells were plated into DMEM/F12 containing 0.9% methylcellulose and 10% FCS at a density of 2,500 cells/mL in a 35-mm petri dish. Immediately after, individual single cells were identified visually under a light microscope, hand-picked using a fine micro-papillary pipette and transferred 1 cell at time to individual 96-well containing 100 uL semisolid media as described above for colony formation.

Histology & Immunohistochemistry.

Histology, immunohistochemistry and whole mount immunohistochemistry staining were performed as previously described (Jorgensen et al. 2007; Seymour et al. 2008). Briefly, colonies were manually picked and fixed in 4% PFA in 4° C. overnight. For frozen sections, colonies were cryoprotected in 30% sucrose in PBS, then embedded in O.C.T. (Sakura Finetek) and sections cut at 10 μm. For whole-mounted IHC, colonies were incubated with blocking buffer with 5% donkey serum and 0.1% triton in 4° C. overnight. Primary antibodies used were as listed in Table 2 above and were detected with donkey-raised secondary antibodies conjugated to Cy3, Cy5, DyLight488 (Jackson Immunoresearch) or Alexa488 (Invitrogen) at 1:2000 dilution (1:500 for Cy5). ApoTome images were captured on a Zeiss Axio Observer Z1 microscope with Zeiss AxioVision 4.8 and figures prepared with Adobe Photoshop/Illustrator CS3. Projection of z-stacks to 3D images or movies was performed with Axiovision 4.8. References for cell markers are: dolichos biflorus agglutinin, ducts (Watanabe et al. 1981; Kobayashi et al. 2002); Spp1 (osteopontin), ducts (Kilic et al. 2006).

Partial Duct Ligation.

Surgery for partial duct ligation was performed as described (Xu et al. 2008; Kopp et al. 2011a).

Microarray Expression Analysis.

Human whole genome microarray kit (4×44K; Agilent Technologies) was used in this study. Four different biological replicates of human $CD133^+CD49f^{low}$ and presort cells were analyzed. Methods for RNA isolation, amplification, reverse transcription, fluorescent labeling and data acquiring were as described (Shin et al. 2011).

Statistical Analysis.

Student's t-test was used to determine statistical significance.

Results

Figure 9:
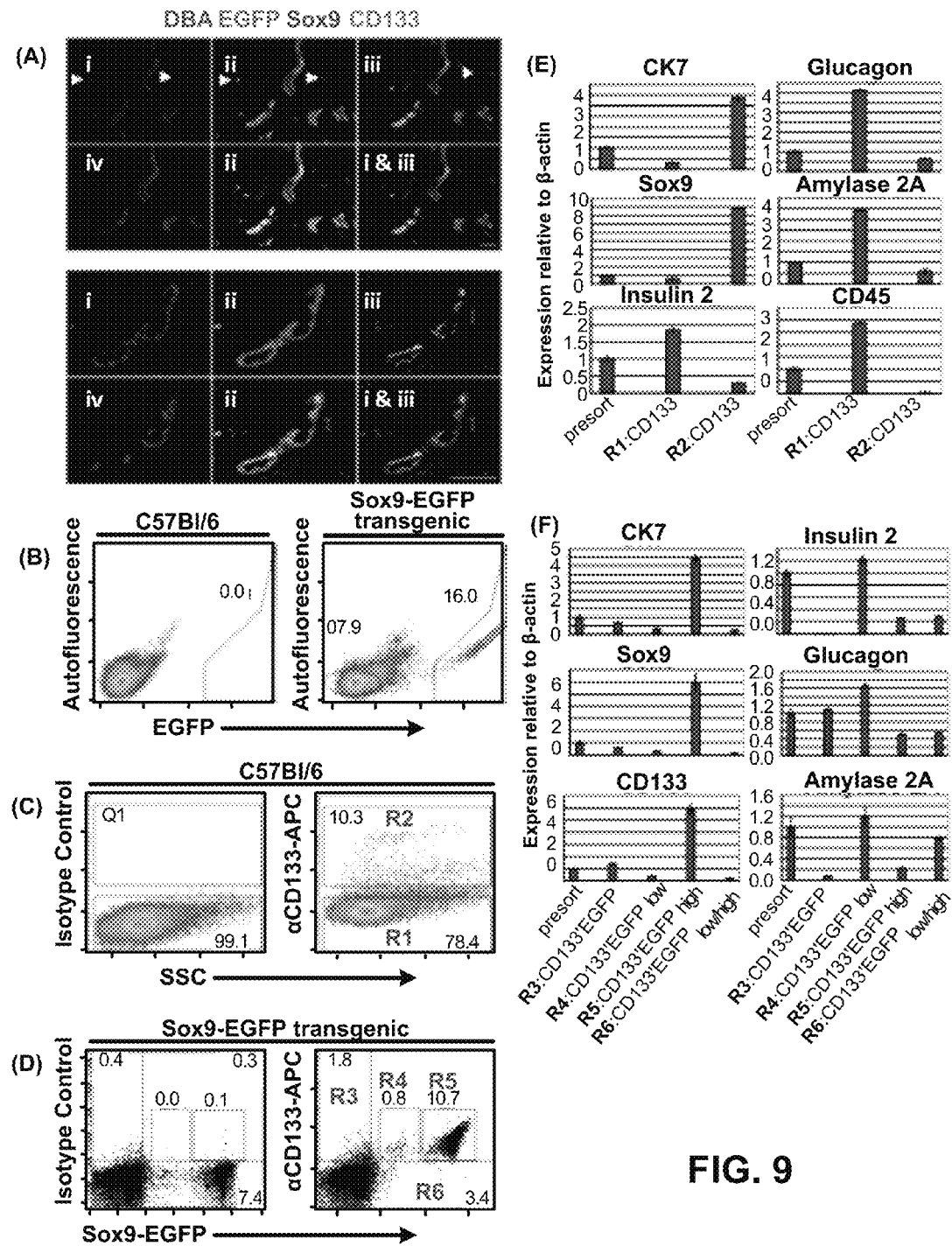
FIG. 9 illustrates the identification and purification of murine adult pancreatic ductal cells. (A) Immunohistochemical staining of DBA (iv), CD133 (iii), Sox9 (i) and EGFP (ii) in 2-month-old Sox9-EGFP transgenic mice showed overlapping expression of these proteins in ducts (i & iii). Arrow heads indicate Sox9$^+$ or CD133$^+$ cells that do not colocalize with ducts. Bars=50 µm. (B-D) Representative flow cytometry analyses of pancreatic EGFP expression in Sox9-EGFP transgenic or B6 wild-type mice (B), CD133 expression in B6 mice (C), or double EGFP and CD133 expression in Sox9-EGFP mice (D). (E-F) Quantitative RT-PCR analyses of designated freshly sorted cells. Data represent three experiments with similar trends.
Figure 10:
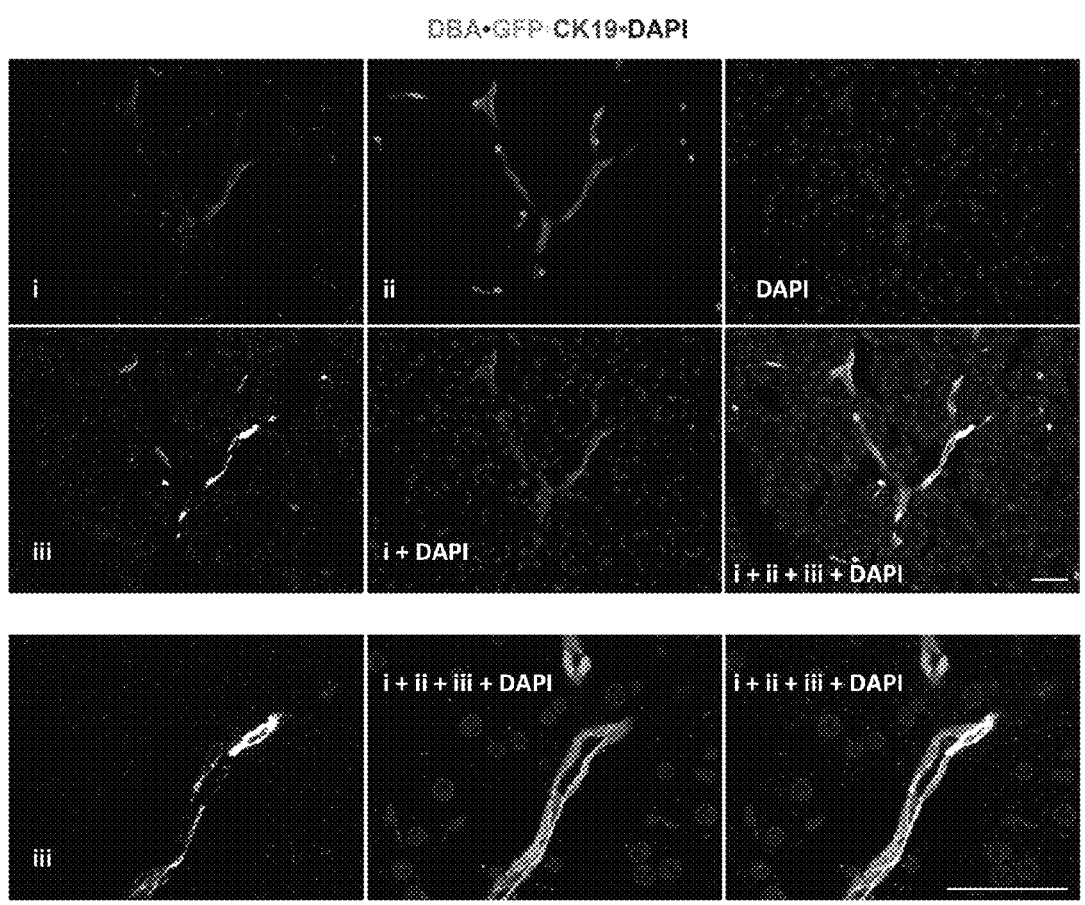
FIG. 10 shows immunohistochemical staining of DBA (iii), CK19 (i), and EGFP (ii) in 2-month-old Sox9-EGFP transgenic mice showed overlapping expression of these proteins in ducts. Bars=50 µm.

Characterization of murine Sox9-EGFP and CD133-expressing cells in adult pancreas. Dolichos biflorus agglutinin (DBA) specifically marks adult pancreatic ductal cells. Immunohistochemical staining was performed to examine the overlap between cells marked by Sox9 or CD133 and DBA in the adult ductal compartment. Because Sox9-EGFP transgenic mice were used in this study to isolate live $Sox9^+$ cells, immunostaining for EGFP was also performed. All $DBA^+$ cells expressed Sox9, CD133 and EGFP (FIG. 9A). $DBA^+$ cells also expressed CK19, a duct-specific marker (FIG. 10). These results confirm that adult ductal cells express Sox9 and CD133 and that the EGFP signal is representative of Sox9 expression. However, not all $Sox9^+$ or $CD133^+$ cells are located in the ductal compartment (FIG. 9A; arrows), suggesting that these cells may be heterogeneous.

To obtain single cells for further studies, whole pancreas was minced and digested with collagenase B and DNase I to yield a single-cell suspension. Fat tissue was cleaned from the pancreas during the dissection to obtain highly viable pancreas cells. After gating with forward scatter and side scatter parameters in flow cytometry analyses, the preparations routinely included of 85 to 98% live cells (as determined by DAPI-staining). $Sox9^-EGFP^+$ or $CD133^+$ cells (from CD1 or C57Bl/6 backgrounds, respectively) in the adult (2 to 4 months old) pancreas represented 8.6±5.7% (3.1 to 15.0%) or 9.7±2.8% (6.5 to 14.7%) of the total population, respectively (FIGS. 9B and 9C), which corresponds to the estimated proportion of ductal cells in the pancreas (Githens 1988). Double-staining revealed that $EGFP^+$ cells can be subdivided into $EGFP^{high}$ and $EGFP^{low}$ cells, and that almost all of the $EGFP^{high}$ cells were also positive for CD133 (CD1 background; FIG. 9D). However, $EGFP^{low}CD133^+$ (0.6%), $EGFP-CD133^+$ (1.6%), and $EGFP^+CD133^-$ (3.4%) cells were also detected (FIG. 9D), again demonstrating heterogeneity among $Sox9^+$ or $CD133^+$ cells (FIG. 9A).

Figure 11:
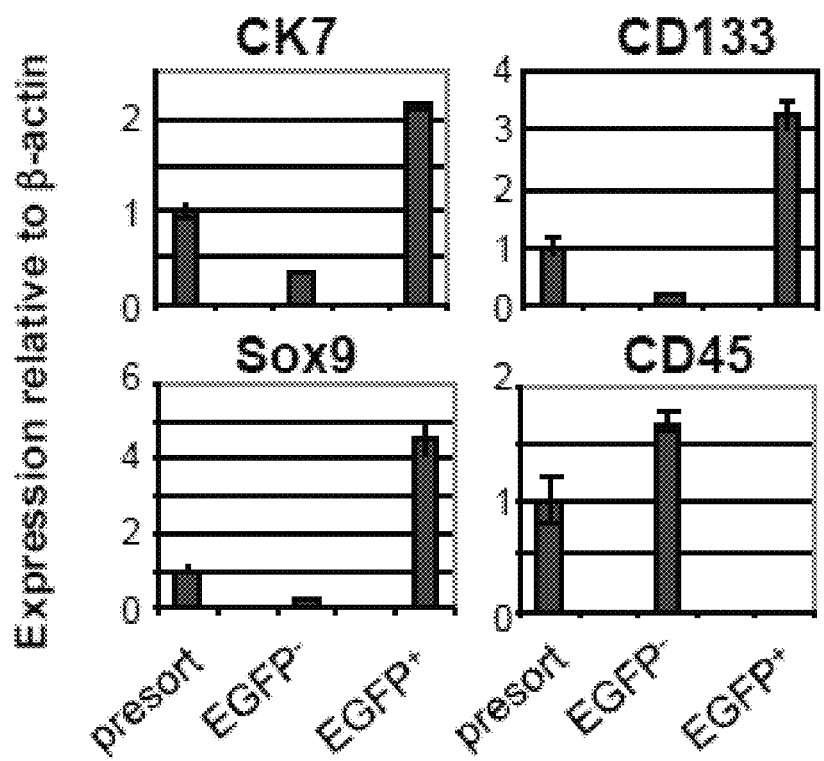
FIG. 11 shows a series of quantitative RT-PCR analyses of indicated markers (CK7, CD133, Sox9 and CD45) in designated freshly sorted Sox9-EGFP cells from murine adult pancreas.
Figure 12:
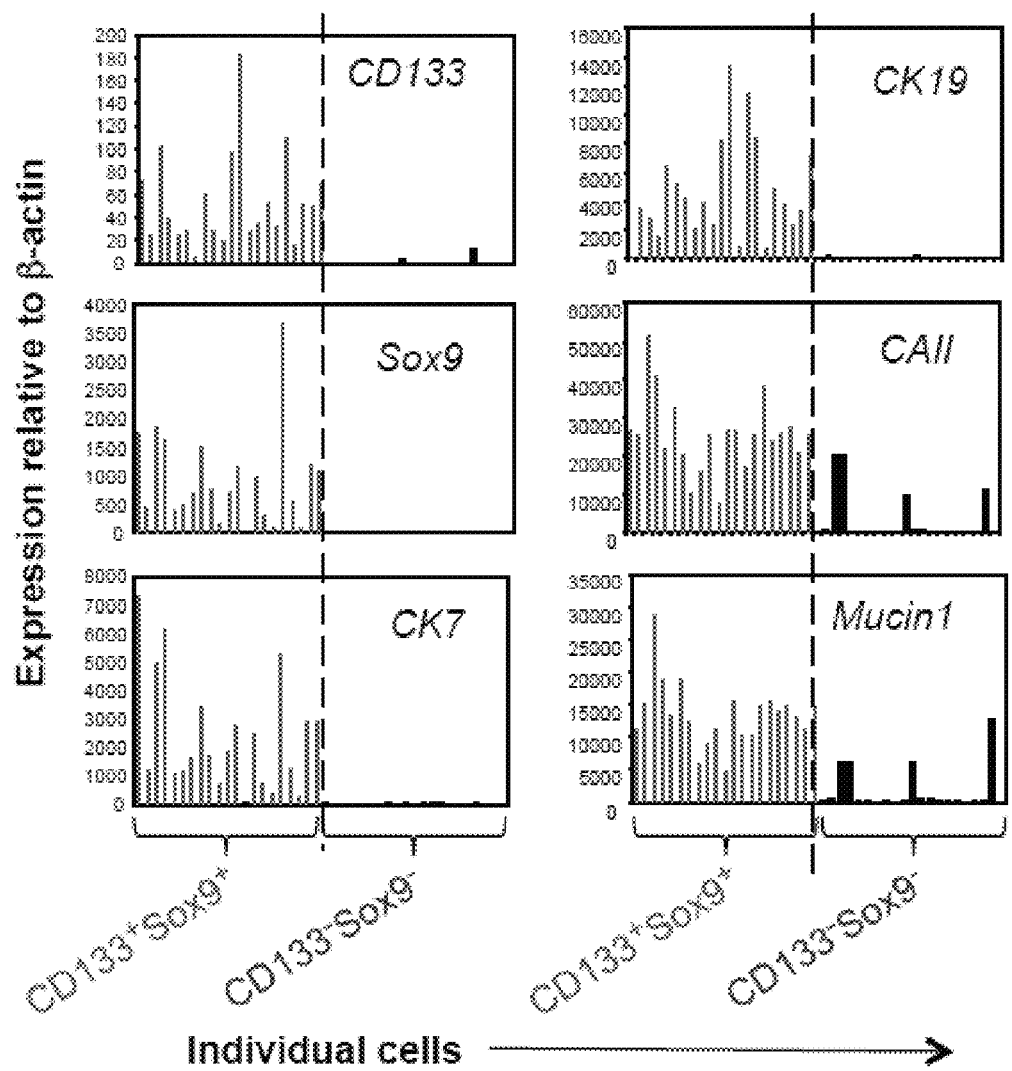
FIG. 12 shows a series of results for single cell gene expression analysis of freshly sorted murine CD133$^+$Sox9-EGFP$^+$ (bars to the left of the dashed line; bars within dashed lin) or CD133$^-$Sox9-EGFP$^-$ (bars to the right of the dashed line) cells. A total of 21 handpicked single cells from each population were subjected to microfluidic RT-PCR analysis. Data represent relative expression of gene-of-interest (as indicated—CD133, CK19, Sox9, CAII, CK7, Mucin 1) as compared to β-actin.

To analyze the gene expression profile of freshly sorted sub-populations of pancreatic cells, total RNA was extracted and analyzed by quantitative RT-PCR using TaqMan probes. $CD133^+$ (FIG. 9E) or $Sox9-EGFP^+$ (FIG. 11) cells expressed higher levels of CK7, a duct-specific marker in the murine and human pancreas, compared to presort cells. In contrast, $CD133^-$ or $Sox9-EGFP^-$ cells were enriched for other lineage-specific markers, such as those for endocrine (insulin 2, glucagon), acinar (amylase 2A), and hematopoietic cells (CD45). Subsequent gene expression analysis of sub-populations revealed that $Sox9-EGFP^{high}CD133^+$ cells were highly enriched for CK7 (FIG. 9F). Microfluidic single-cell RT-PCR analysis of 21 individually hand-picked $Sox9-EGFP^{high}CD133^+$ cells showed that these cells expressed higher levels of ductal markers (CK7, CK19, mucin1, CAII, Sox9 and CD133) than $Sox9-EGFP^-CD133^-$ cells (FIG. 12), further demonstrating that $Sox9-EGFP^{high}CD133^+$ cells represent ductal cells.

Colony-Forming Activities in Murine Pancreatic Sox9 and CD133 Expressing Cells.

An in vitro quantitative assay for colony-forming progenitors derived from murine embryonic stem cells was established and described above. This culture system was adapted from a hematopoietic colony-forming assay, which uses semi-solid media to restrict the movement of single progenitor cells yet permits self-renewal, proliferation and differentiation to occur in vitro in the absence of niche cells. It is possible to quantify the number of progenitor cells in the starting material by counting the number of differentiated colonies that arise.

Figure 13:
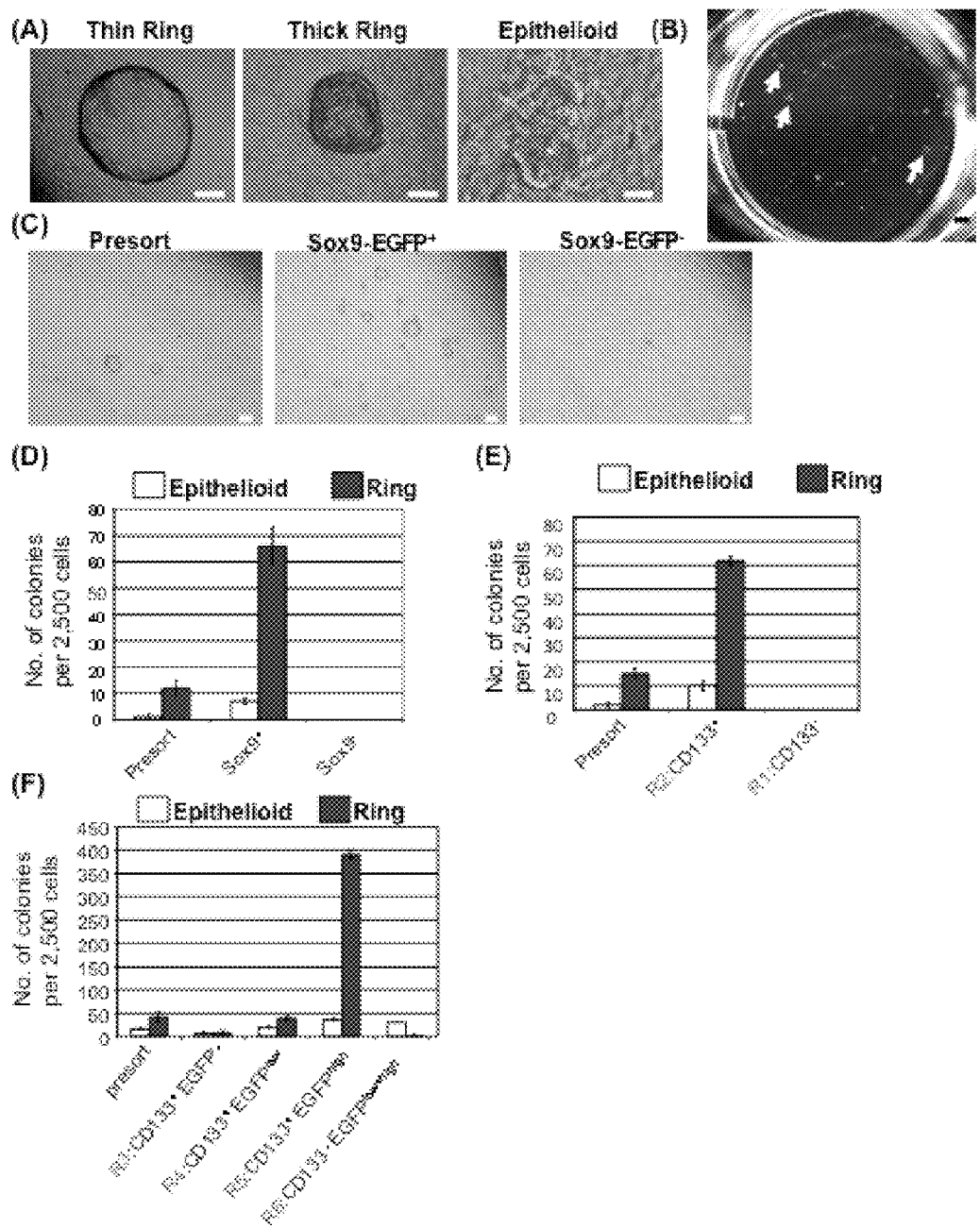
FIG. 13 illustrates colony-forming activities from murine adult pancreatic ductal cells. (A) Photomicrographs taken from a light microscope of designated colony developed 20 days post plating from dissociated pancreatic cells. (B) Ring colonies were in fact cystic when observed under a stereomicroscope. (C) Photomicrographs of Ring colonies showed that colony forming activities were associated with Sox9-EGFP$^+$ but not Sox9-EGFP— cells six days post-culture. (D-F) Quantification of the number of Ring and Epithelioid colonies arising from designated sorted cells (E-F). Data represent three experiments with similar trends.

The assay described above was used to test whether adult murine pancreatic cells can form colonies. Dissociated single-cell suspensions of adult pancreatic cells (pre-sorted cells) were plated into semi-solid media containing Matrigel and growth factors, and colony formation was monitored. Between 20 to 31 days after culture, two major types of colonies with distinctive morphologies were observed, which were termed Ring (subdivided into thin and thick Rings based on the thickness of the ring wall) and Epithelioid (FIG. 13A). Ring colonies appeared circular under the light microscope, but were revealed under the stereomicroscope to be cysts (FIG. 13B). Epithelioid colonies, in contrast, contained cells organized as "buds" protruding into space (FIG. 13A). Structures similar to Ring (Bonner-Weir et al. 2000; Gao et al. 2003; Githens 1998; Schreiber et al. 2004; Wescott et al. 2009) or Epithelioid (Fanjul et al. 2010) colonies have been previously described in cultures of partially purified adult human or rat ducts.

Next, it was determined which sub-populations of cells are found in the Ring or Epithelioid colony-initiating cells. Adult murine pancreatic cells were sorted based on Sox9 and/or CD133 expression, plated into semi-solid media and examined for colony formation. Ring (both thin and thick) and Epithelioid colonies were found exclusively in wells seeded with 2,500 Sox9-EGFP$^+$, but not with Sox9-EGFP$^-$ cells (FIGS. 13C and 13D). Sorting cells based on CD133 expression yielded similar results (FIG. 13E), with Rings representing the major colony type and Epithelioid the minor. The number of these colonies demonstrated an 11.7- and 9.5-fold enrichment of Ring and Epithelioid colony-forming progenitors, respectively, in the CD133$^+$ cells compared to pre-sorted cells (FIG. 13E). Further fractionation revealed that, of all the sorted subpopulations, CD133$^+$ Sox9-EGFP$^{high}$ cells were the most highly enriched for Ring and Epithelioid colony-forming activities (FIG. 13F). However, only 17% of CD133$^+$Sox9-EGFP$^{high}$ cells gave rise to Ring and Epithelioid colonies (FIG. 13F), demonstrating that adult ductal cells vary in their ability to function as progenitor cells.

Figure 14:
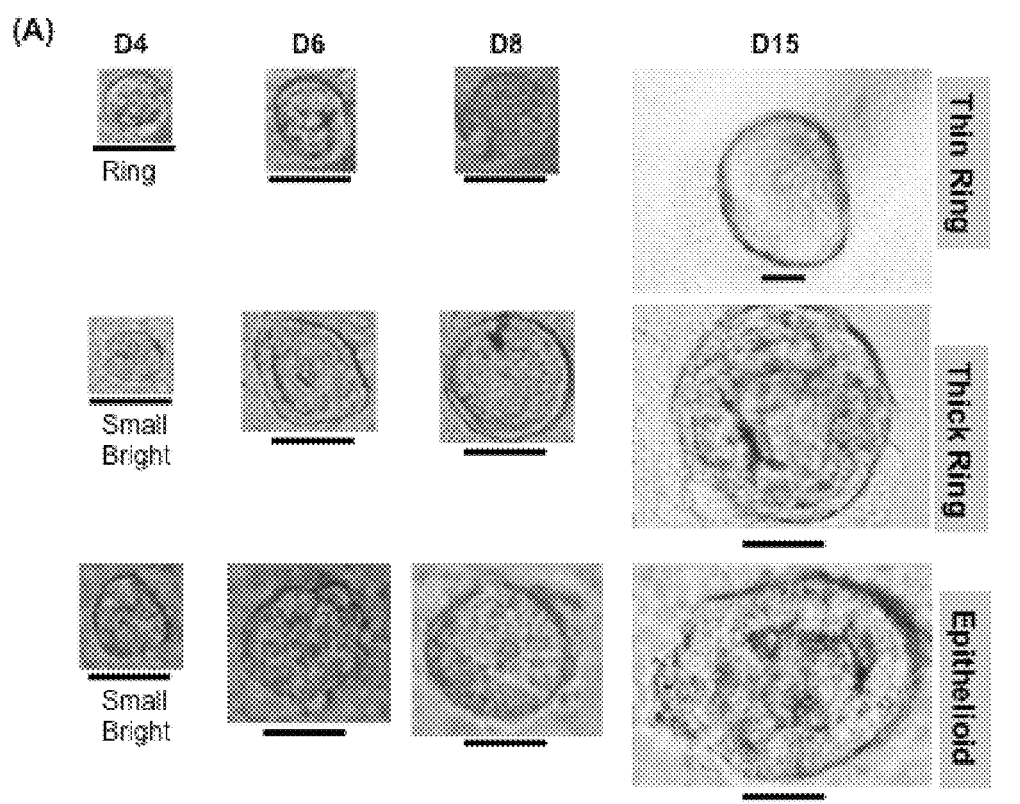
FIG. 14 shows colony development and single cell origin of individual Ring, Small Bright and Epithelioid colonies. (A) Developing colonies of murine cells were mapped with their location and photomicrographs taken on designated days post-plating. (B) Top: Schematic of micro-manipulation of single sorted cell using micro-papillary pipette to inoculate one cell per well for colony formation. Bottom: Photomicrographs of four individual colonies that developed from 48 single micro-manipulated Sox9-EGFP$^{high}$ cells 13 days post-culture are shown. All bars=100 µm. Data represent two experiments showing colonies with similar morphology.
Figure 14:
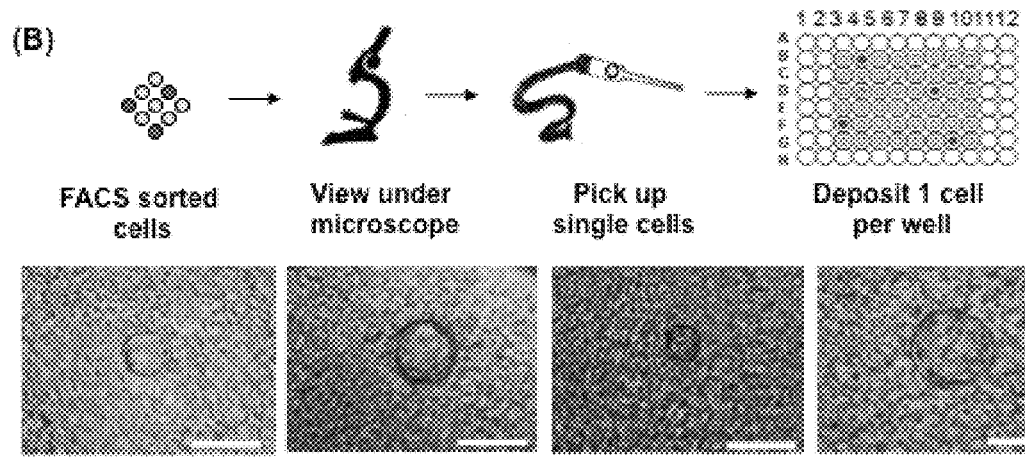

Mapping colony development and single-cell origin for individual murine colonies. To understand how Ring and Epithelioid colonies develop in vitro, sorted mouse CD133$^+$ cells were plated and the development of individual colonies was followed over time. As early as day 2 to 4 (FIG. 14A), colonies consisted of small aggregates of cells that were bright and highly reflective. This type of colony was named "Small Bright". As time progressed, the Small Bright colonies subsequently developed into either Ring or Epithelioid colonies (FIG. 14A).

To test the origin of individual colonies, single cells were picked under a microscope with a fine micro-papillary pipette immediately after sorting and transferred into 96-well plates at one cell per well for culture. Four individual colonies formed from a total of 48 singly seeded Sox9-EGFP$^{high}$ cells (FIG. 14B), demonstrating that one cell is sufficient to initiate the formation of one colony.

Characterization of Individual Murine Colonies.

The types of cells found within each colony is indicative of the lineage potential of the initiating progenitor. To determine the mixture of cells found in each type of colony (Small Bright, Ring, and Epitheliod), single-colony microfluidic RT-PCR analysis was performed (FIG. 15A). A panel of TaqMan probes was used for housekeeping (beta actin, macroglobulin, and cyclophillin G), ductal (CK7, mucin 1, beta 1 integrin, CAII, CD133, Sox9), pancreatic progenitor cell (Pdx1, Ngn3 16, CD133, Sox9, c-Met 11, ALDH 1 14, DCAMKL1, DCAMKL2), endocrine (insulin 1, insulin 2, glucagon, somatostatin, PPY, ghrelin), acinar (amylase 2A, elastase 1, carboxypeptidase A), and endocrine hormone maturation markers (PCSK1 and PCSK2). Adult murine pancreatic CD133$^+$ cells were plated at 1,000 cells per well in 24-well plates to ensure that the resulting colonies were well separated from one another to facilitate colony picking. Individual Small Bright, Ring (either thin or thick), and Epithelioid colonies were hand-picked at various time points (days 10, 20 and 31 after plating) and analyzed.

Figure 16:
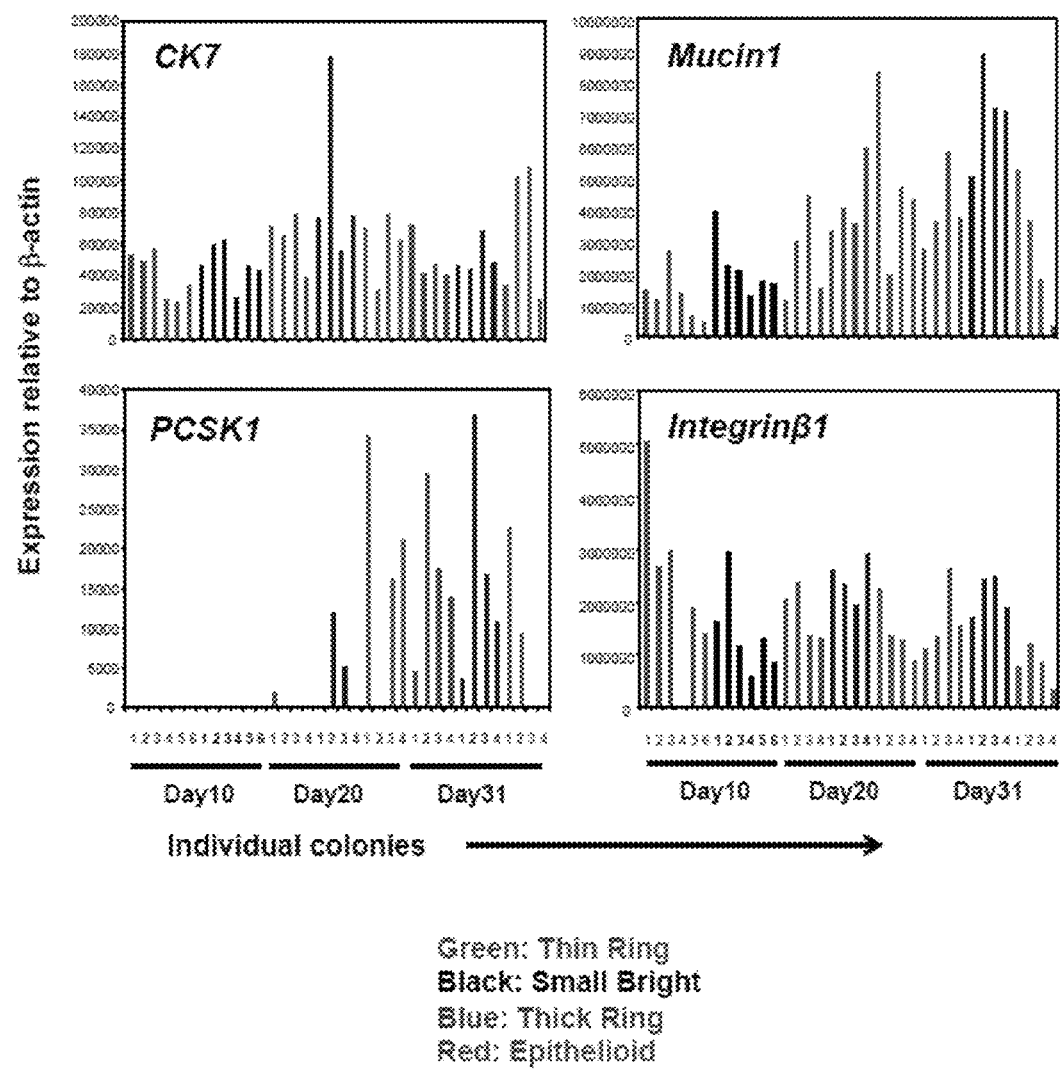
FIG. 16 shows the levels of prohormone convertase 1 (PCSK1) and Mucin 1 in individual murine colonies increased over time in culture. Representative genes in microfluidic RT-PCR analysis shown in FIG. 15 were reanalyzed as relative expression compared to the internal control β-actin.

With the exception of PCSK1, it was found that the overall gene expression profile did not differ dramatically among colonies collected on different days. PCSK1 is a prohormone convertase expressed in mature endocrine cells at day 31 but not at day 10, indicating a gradual maturation of the colonies over time. Analysis of gene expression relative to beta-actin further confirmed the increase of PCSK1 overtime (FIG. 16). Consistent with the idea that colony-initiating cells originate from the ductal compartment (FIGS. 9 and 13), all of the resulting colonies expressed high levels of ductal markers (CK7, mucin1, beta 1 integrin, CAII, CD133, and Sox9), suggesting that the ductal progenitors preferentially differentiate into ductal-like cells in the colony assay. In contrast, acinar and endocrine genes were expressed at lower levels, indicating they are minor components of individual colonies.

Next, the 36 colonies were analyzed to determine how many expressed both endocrine and acinar genes. Of these colonies, only six were identified that did not express endocrine markers and four were identified that failed to express acinar genes (FIG. 16B). This demonstrates that the majority (26/36; 72%) of the colony-forming progenitor cells are multipotent for duct, endocrine and acinar cell lineages.

There are five known endocrine lineages: alpha, beta, delta, PP and epsilon cells, which express glucagon, insulin, somatostatin, pancreatic polypeptide and ghrelin, respectively. To ascertain whether an individual colony-forming progenitor cell gives rise to all five endocrine cell types, the colonies, which originated from a single progenitor, were analyzed for the expression of all five endocrine hormone genes. None of the analyzed colonies expressed somatostatin. Only one out of 36 (3%) colonies simultaneously expressed insulin, glucagon, and PPY, and seven (19%) colonies expressed both insulin and glucagon (FIG. 16C), suggesting that colony-initiating progenitors with the potential to develop into multiple endocrine lineages are rare.

The prevalence of individual colonies expressing each of the five endocrine genes was then quantified. Colonies expressing insulin (insulin 1 or insulin 2) were the most prevalent (25/36; 69%), followed by colonies expressing glucagon (12/36; 33%), PPY (4/36; 11%), and ghrelin (3/36; 8%) (FIG. 16D). These results suggest that individual ductal progenitors are more likely to differentiate into colonies containing beta-like cells than into colonies containing cells of other endocrine cell types.

Transmission electron microscopy of Ring and Epithelioid colonies demonstrated that cells with microvilli and tight junctions—hallmarks of ductal cells—were prominent (FIG. 17A). These fine structures were located on the apical surface facing the lumen, but not on the basal membranes that come in contact with Matrigel, demonstrating that the cells display duct-like polarity. In addition, cells with microvilli contain zymogen-like secretory granules (FIG. 18), which suggests the cells may exist in a state of transition between ductal and acinar cells.

Figure 17:
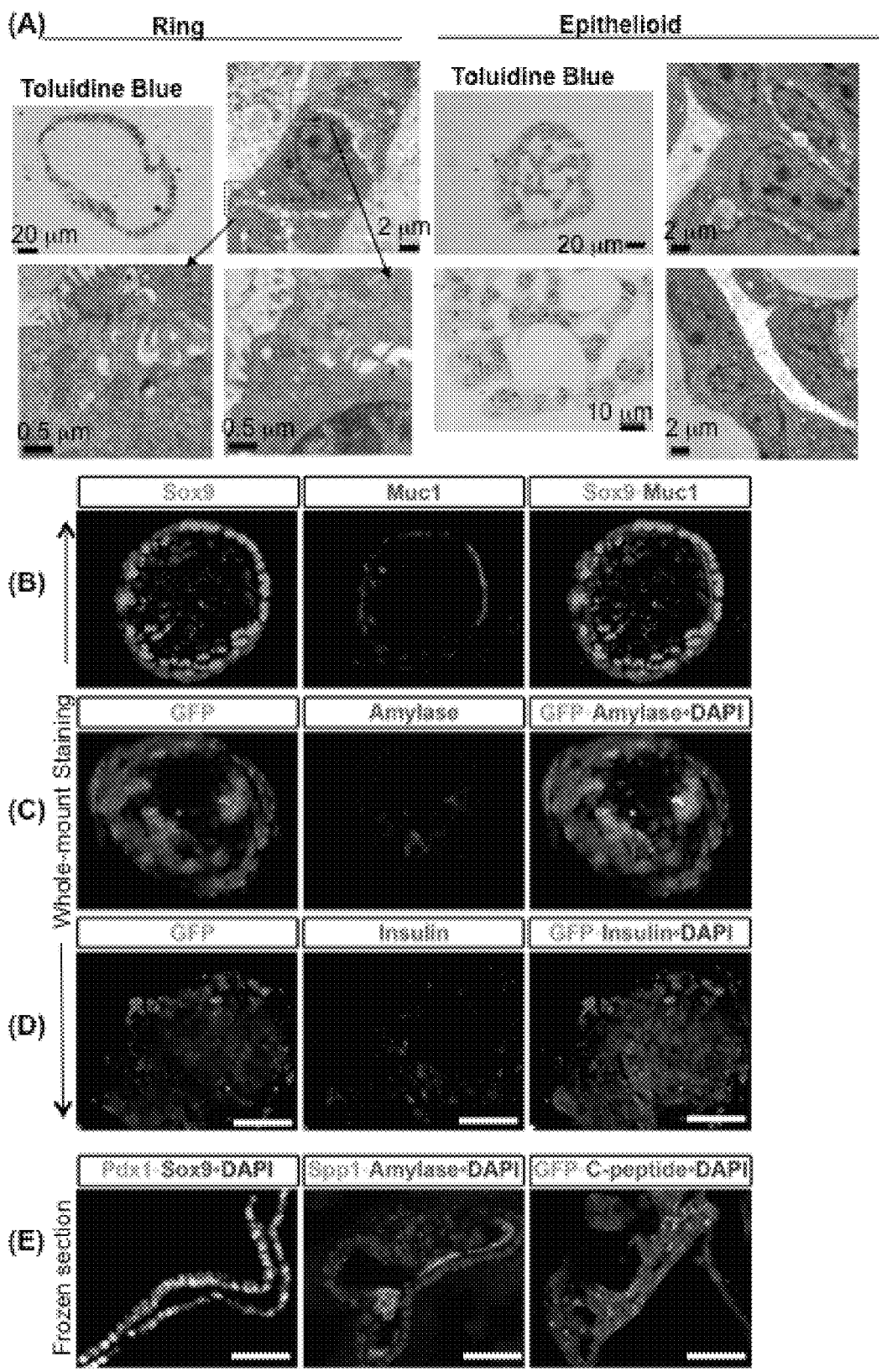
FIG. 17 shows electron microscopy and immunostaining analyses of individual murine colonies. (A) Transmission electron microscopy analysis of representative individual Ring or Epithelioid colonies derived from CD133+ cells. Toluidine blue was used to counter-stain the sectioned colonies. (B-E) Immunostaining of individual whole mounted (B-D) or frozen sections (E) of colonies derived from Sox9-EGFP$^+$ cells. Data represent three experiments with similar ultra-structures and staining.
Figure 18:
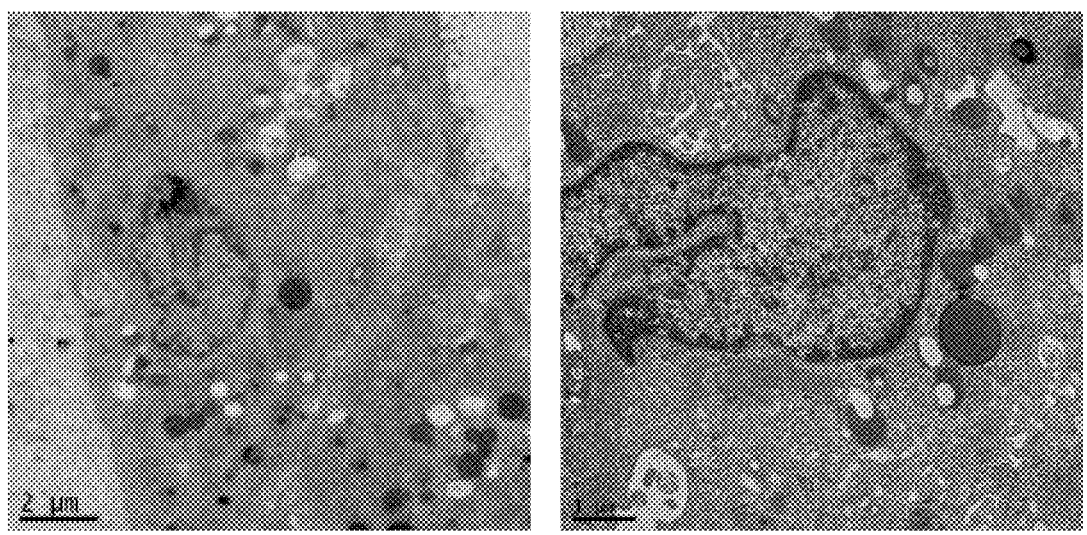
FIG. 18 shows an transmission electron microscopy analysis showing granules formed in the cytoplasm of cells from a murine Ring colony (left) and an Epithelioid colony (right). Data are representative from 3 experiments showing similar results.

Immunofluorescent staining of individual handpicked colonies in whole-mount or frozen sections confirmed the expression of the ductal markers mucin 1 or Spp1 (osteopontin), respectively (FIG. 17). These proteins localized to the luminal cell membrane in the Ring colonies, which provides further evidence that these ductal-like cells properly establish cell polarity in the colonies. Only a small subset of cells (which either clustered together or existed as single cells) expressed amylase (FIGS. 17C and 17E) or insulin/C-peptide (FIGS. 17D and 17E), suggesting that endocrine or acinar lineage commitment is a minor event. Alternatively, this minimal differentiation of endocrine and acinar lineages may reflect a sub-optimal culture condition for these lineages.

Taken together, the results of the colony assay demonstrate that 1) individual Ring and Epithelioid colonies are predominantly composed of ductal-like cells, and 2) the majority of single ductal progenitors are capable of multi-lineage differentiation to duct, acinar and endocrine cells.

Self-Renewal of Murine Ductal Progenitor Cells In Vitro.

Figure 19:
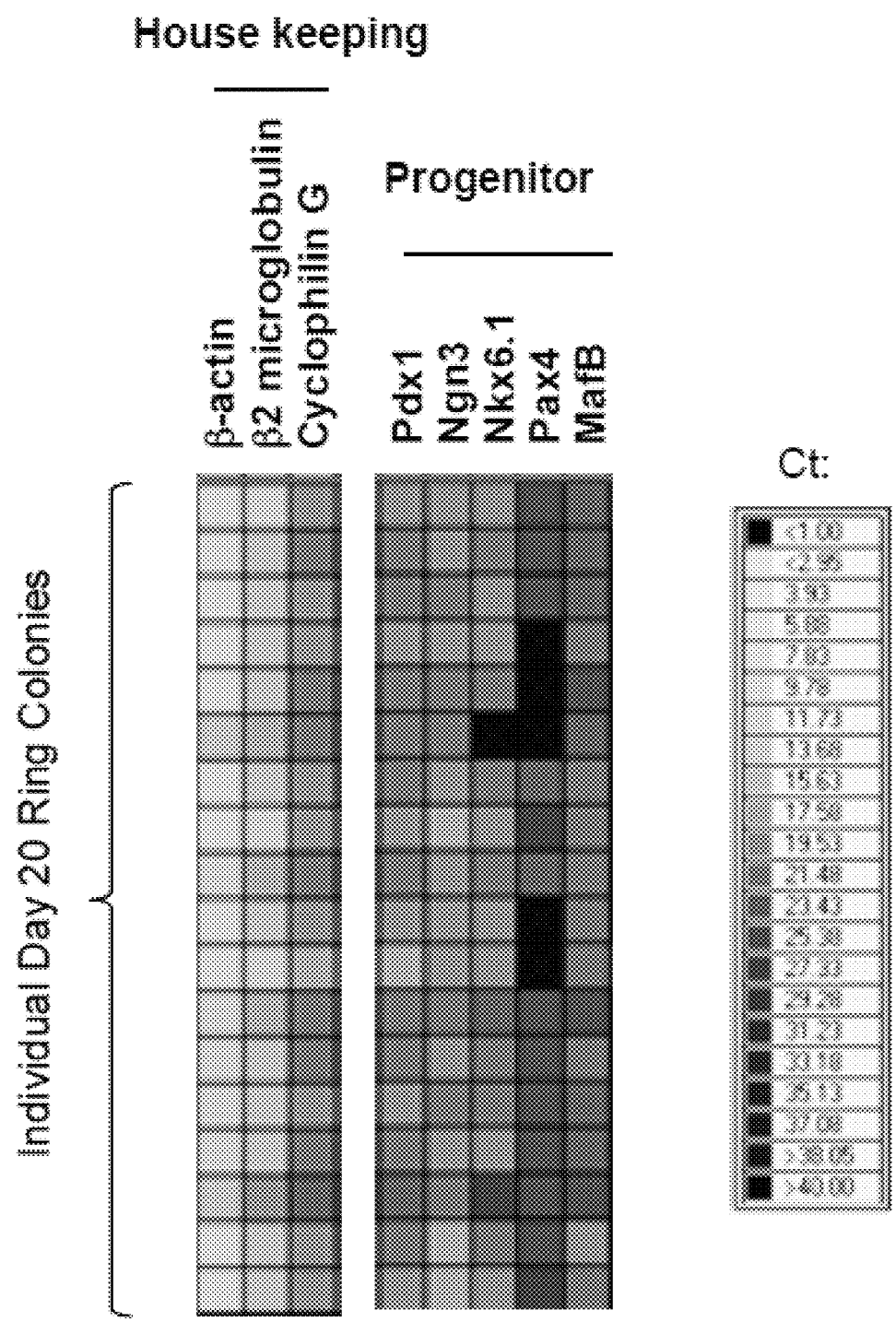
FIG. 19 illustrates the expression of murine pancreatic progenitor cell transcription factors in individual colonies. Adult murine pancreatic CD133$^+$ cells were sorted, cultured for 20 days to form colonies and individually handpicked for microfluidic RT-PCR analysis using designated TaqMan probes. Data represent the Ct value (expressed as a designated color) of each gene analyzed. Progenitor cell markers examined were Pdx1, Ngn3, Nkx6.1, Pax4 and MafB.

It was noted that individual colonies expressed the pancreatic progenitor cell markers Pdx1 (FIG. 19), Ngn3, Sox9, CD133, c-Met, ALDH1, DCAMKL1, and DCAMKL2 (FIG. 16A). Expression of the Pdx1 protein was further confirmed by immunostaining (FIG. 17E). These results suggest that the original colony-initiating progenitors self-renew during culture (Sharma et al. 1999). To examine this possibility, individually handpicked primary colonies were dissociated into single cells and were replated into secondary cultures. Many (8 out of 10 colonies examined; 80%) colony-forming progenitor cells were capable of self-renewal during the primary culture (Table 3). However, the ability of primary progenitors to self-renew varied, as evidenced by a wide range in the number of newly derived cells that can then go on to form secondary colonies (Table 3). This finding suggests that colony-forming cells are heterogeneous in their potential to self-renew.

TABLE 3

Secondary colony-forming ability from individual primary colonies.

| 1° Colony | No. of 2° Colonies | 1° Colony | No. of 2° Colonies |
|---|---|---|---|
| Ring 1 | 73 | Epithelioid 6 | 13 |
| Ring 2 | 3 | Epithelioid 7 | 12 |
| Ring 3 | 12 | Epithelioid 8 | 13 |
| Ring 4 | 0 | Epithelioid 9 | 5 |
| Ring 5 | 0 | Epithelioid 10 | 60 |
| Average ± SD | 18 ± 31 | | 21 ± 22 |

CD133+ cells were sorted from pancreas of 4-month-old mice and cultured at 2,500 cells per well for a total of 20 days. Colonies were individually handpicked, dissociated and plated into secondary culture. The number of colonies was scored after 20 days in secondary culture.

Figure 20:
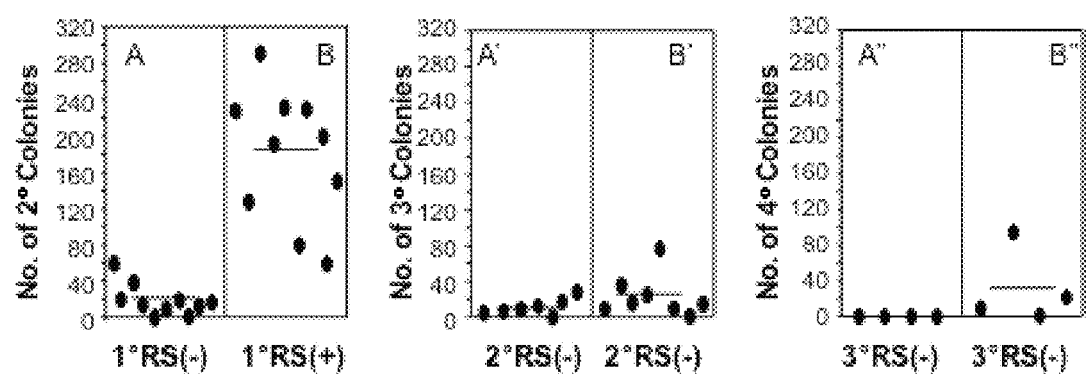
FIG. 20 is a series of scatter plots illustrating that self-renewal of colony-forming progenitor cells is enhanced by exogenous R-Spondin 1. Murine CD133$^+$ cells were plated into primary culture, in the absence (−) or presence (+) of 750 ng/mL R-Spondin 1 (RS). On day 20, individual colonies (n=10) from primary cultures were handpicked, dissociated into a single-cell suspension, and plated into secondary culture in the absence of RS. The number of secondary colonies was scored on day 20 post-culture (left panel). Clonal colonies were serially replated (e.g. B to B' to B") to obtain the number of tertiary (middle panel) and quaternary (right panel) colonies. Bar represents average number of colonies. Data represent two experiments with similar trends.

Wnt signaling has been shown to increase the self-renewal capacity of various adult stem cells. Thus, the effects of exogenous recombinant R-Spondin 1, a Wnt agonist, on the self-renewal capacity of individual colony-forming progenitors were tested. Addition of R-Spondin 1 during primary culture enhanced by nearly ten times the average number (~180) of secondary colonies arising from dissociated individual primary colonies compared to controls grown in the absence of R-Spondin 1 (~20) (FIG. 20; left panel). The exposure of primary colonies to R-Spondin1 was sufficient to sustain subsequent colony formation in serially re-plated clonal cells even in the absence of R-Spondin 1 (FIG. 20; middle and right panels). Together, these results demonstrate that the self-renewal capacity of individual adult ductal progenitor cells is enhanced by exogenous R-Spondin 1.

Partial Duct Ligation Alters the Prevalence of Murine Pancreatic Ductal progenitor cells.

Figure 21:
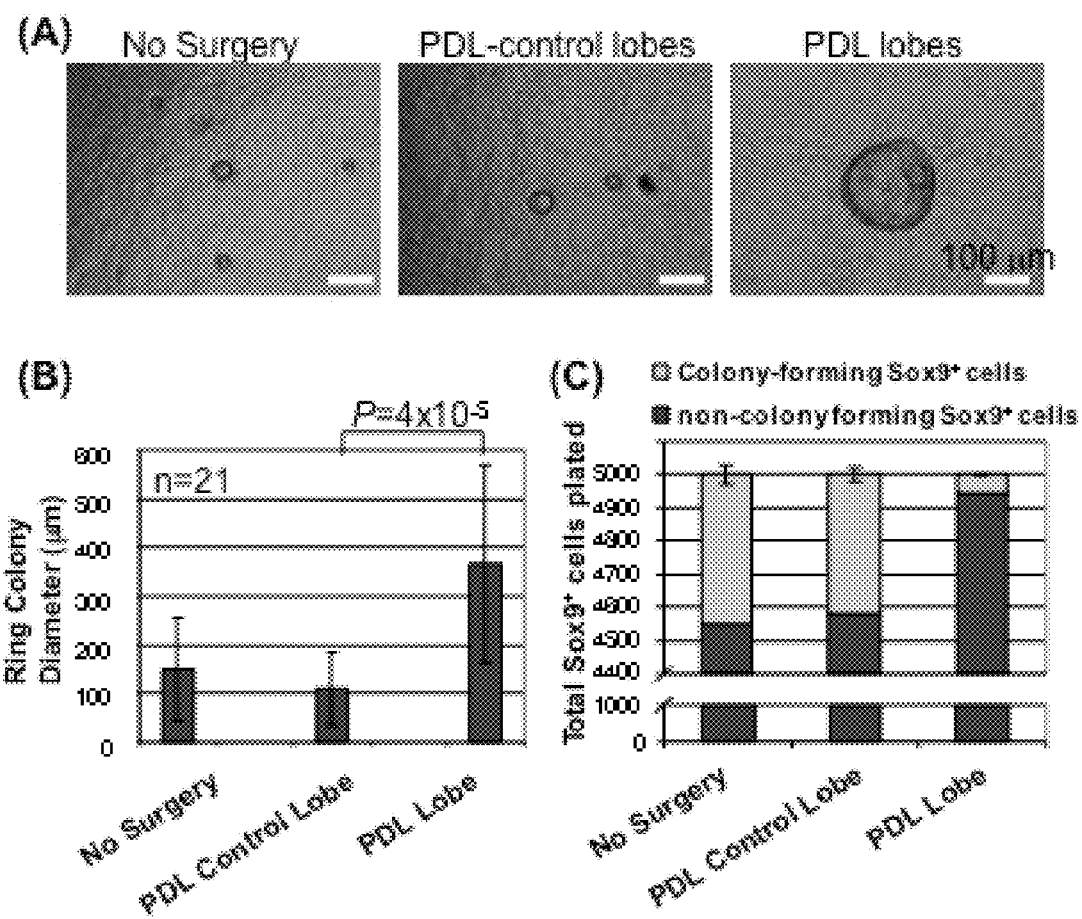
FIG. 21 shows the effects of in vivo partial duct ligation on colony formation in vitro. (A) Photomicrographs of 10-day-old colonies from Sox9-EGFP$^+$ cells from age-matched unmanipulated murine pancreas, PDL control lobes, or PDL-treated tail lobes (8 days post ligation). (B) The diameters of Ring colonies were measured and analyzed by t-test. N=21. (C) Comparison of the number of colony-forming versus non-colony-forming cells among 5,000 Sox9-EGFP$^+$ cells plated. N=4. Data represent two experiments with similar trends.
Figure 22:
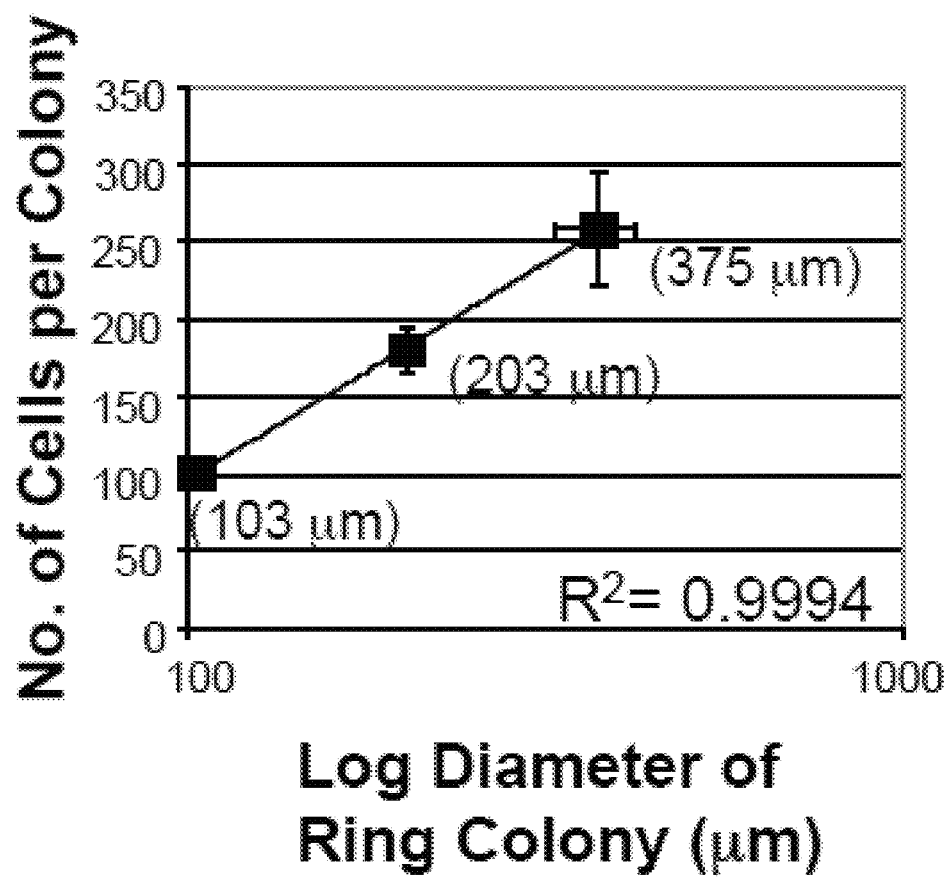
FIG. 22 shows a correlation of the diameters of the murine Ring colonies versus the number of cells per colony. Colonies (20-day-old derived from CD133$^+$ cells) were measured for their diameters before dissociated into single cell suspension and counted for total cell number. Each data point represented mean and standard deviation of diameter (α-axis) or cell number (y-axis) of 4 individual colonies of similar sizes. High correlation (R2=0.9994) was observed between these two parameters.

Partial Duct Ligation (PDL) Induces Pancreatitis and Damages Ductal and acinar cells (Pinho et al. 2011). Studies were conducted to determine whether the function of ductal stem and progenitor cells is affected by PDL. Sox9-EGFP+ and Sox9-EGFP− cells were sorted and plated for colony assay. Sox9-EGFP− cells did not give rise to colonies. The Ring colonies that developed from Sox9-EGFP+ cells from PDL-treated mice were significantly larger than those from untreated mice (FIGS. 21A and 21B). Because the diameter of a Ring colony is correlated with the number of cells in that colony (FIG. 22), these results suggest that PDL induces individual Sox9+ colony-forming progenitors to proliferate more rapidly than those from untreated mice. In addition, it was observed that the ratio of non-colony-forming to colony-forming ductal cells increased nine-fold eight days after partial duct ligation in vivo (FIG. 21C), suggesting that one consequence of PDL is the generation of committed ductal cells (which cannot form colonies) from activated progenitors. Together, these results suggest that PDL activates ductal progenitors to repair damaged ducts.

Human Adult Pancreatic CD133+ Cells are Enriched for Colony-Forming Progenitors.

Figure 23:
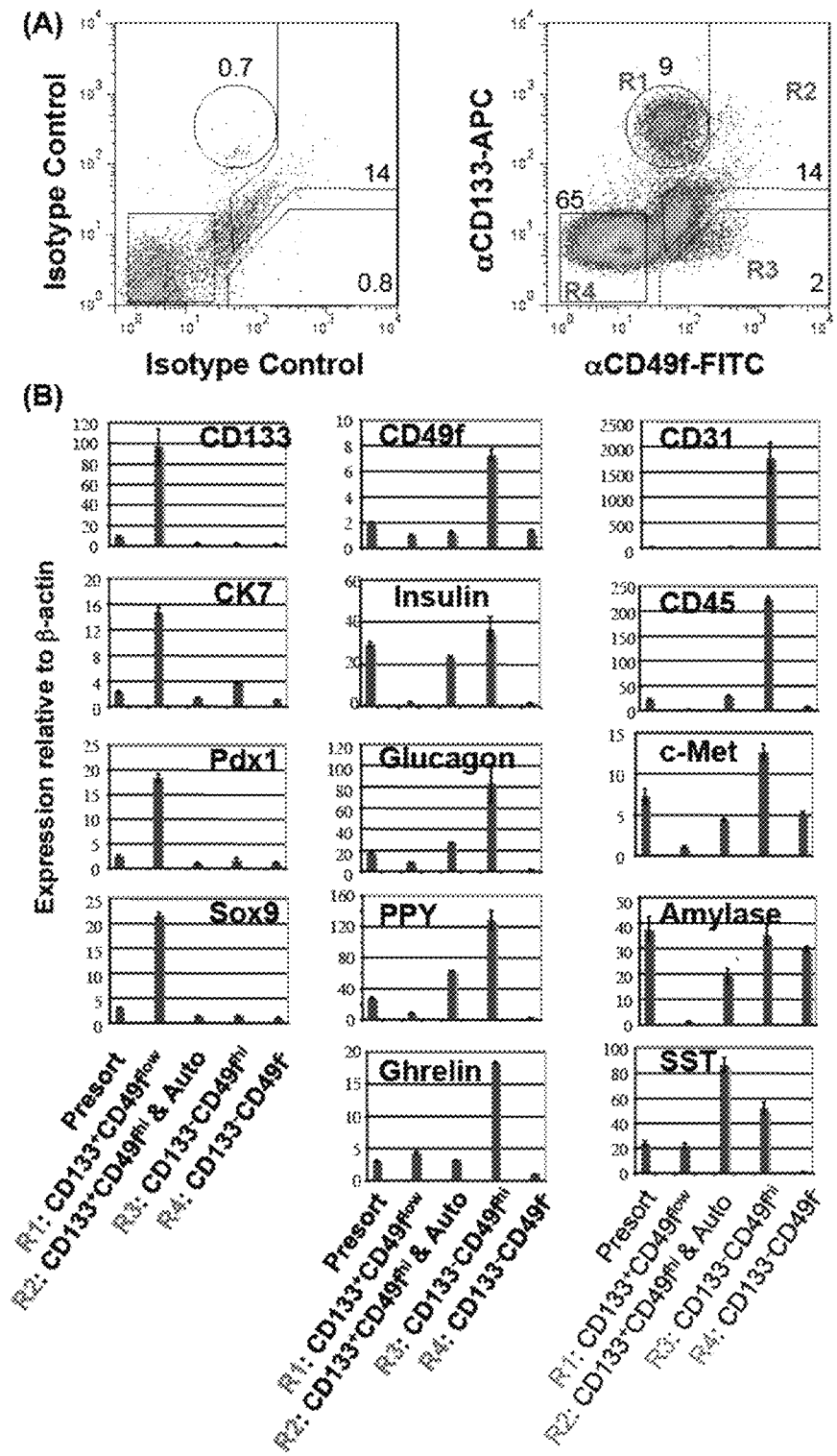
FIG. 23 shows characterization of freshly sorted human adult pancreatic CD133$^+$CD49f$^{low}$ cells. (A) Anti-CD133 and CD49f antibodies stained a discrete population of cells from human adult pancreatic cells. (B) Gene expression analysis by quantitative RT-PCR of designated sorted subpopulations. Sort windows (R1 to R4) were indicated as in (A). (C) Adult human CD133$^+$CD49f$^{low}$ cells (second lane) expressed higher levels of ductal (CK7, Sox9, CAII, HNF1b, HNF6) and pancreatic progenitor (Pdx1, Nkx6.1, and Ngn3) markers.
Figure 23:
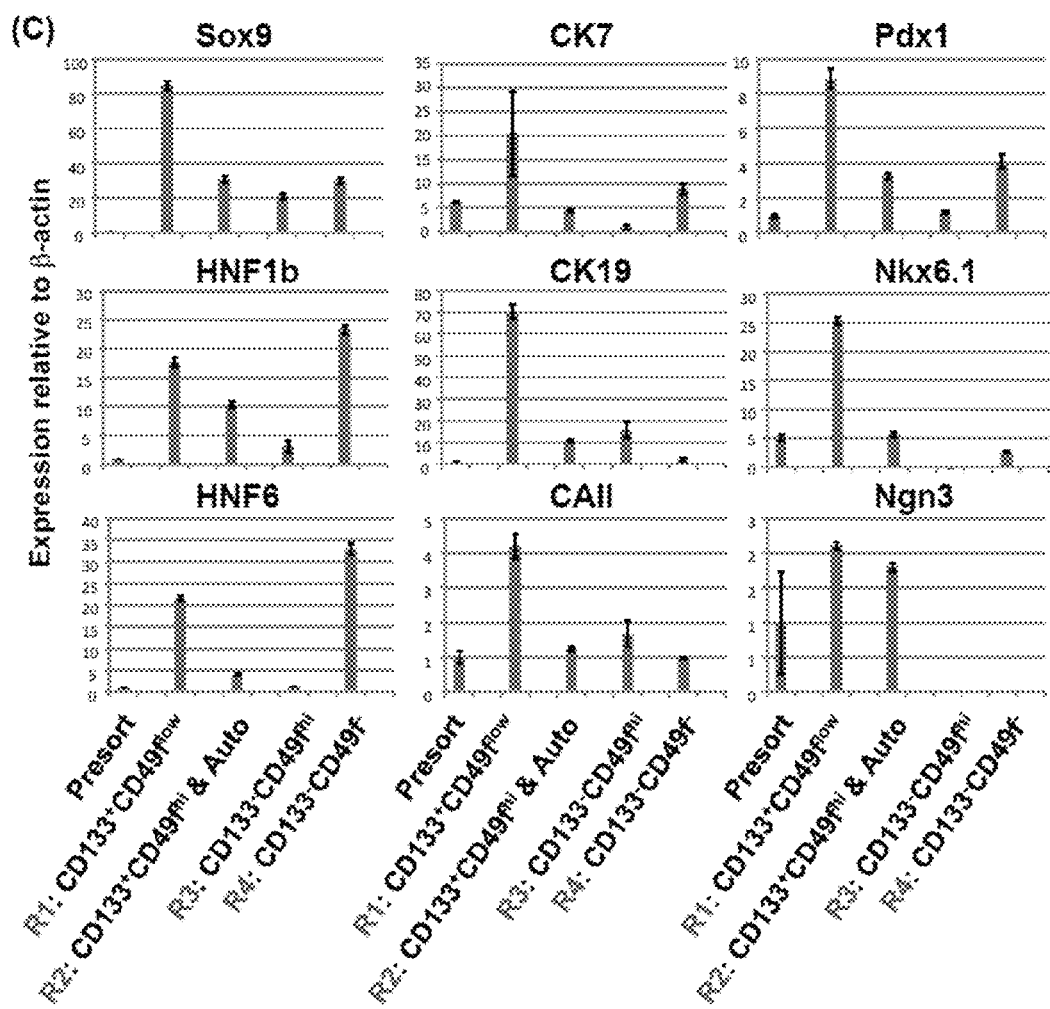

To test whether single human ductal cells are able to form colonies in vitro, cadaveric pancreas was partially digested, the islets were removed, and the remaining duct-containing clusters were further dissociated into a single-cell suspension. This suspension was then stained with antibodies against CD133 and CD49f, which is expressed at low levels in human fetal pancreatic endocrine progenitor cells (Sugiyama et al. 2007). All of the pancreatic CD133+ cells, which comprised 3.4±1.1% (2.3-5.0%) of the total population from multiple human donors, were CD49f$^{low}$ (FIG. 23A). Quantitative RT-PCR analysis of freshly sorted cells revealed that these CD133+CD49f$^{low}$ cells consistently expressed high levels of CD133, Sox9, and CK7, but not of other markers such as insulin, glucagon, PPY, somatostatin, ghrelin, amylase, CD31 and CD45 (FIG. 23B). This gene expression pattern suggests that CD133+CD49f$^{low}$ cells are ductal cells from the adult human pancreas. Furthermore, expression of additional markers for ductal (CK19, CAII, HNF1b, HNF6) and progenitor (Pdx1, Nkx6.1, Ngn3) cells were also found to be enriched in the CD133+CD49f$^{low}$ cells (FIG. 23C). Finally, genome-wide gene expression analysis comparing CD133+CD49f$^{low}$ to pre-sorted cells confirmed the ductal identity of CD133+CD49f$^{low}$ cells; keratin and transporter proteins for bicarbonate and ions were among the most highly expressed genes (Table 4).

TABLE 4

Partial list of most highly expressed genes in human pancreatic CD133+CD49f$^{low}$ cells compared to presort cells.

| Gene Name | Description | Fold Enriched | NCBI ID No. |
|---|---|---|---|
| SLC4A4 | solute carrier family 4, sodium bicarbonate co transporter, member 4 | 25.6 | NM_003759 |
| ATP13A4 | Atlases type 13A4 | 25.2 | NM_032279 |
| WDR66 | WD repeat domain 66 | 24.1 | NM_144668 |

TABLE 4-continued

Partial list of most highly expressed genes in human pancreatic CD133$^+$CD49f$^{low}$ cells compared to presort cells.

| Gene Name | Description | Fold Enriched | NCBI ID No. |
| --- | --- | --- | --- |
| PCYT1B | phosphate cytidylyltransferase 1, choline, beta | 23.4 | NM_004845 |
| CALHM3 | Protein FAM26A | 22.9 | NM_001129742 |
| MATN2 | matrilin 2 | 22.2 | NM_030583 |
| SMOC1 | SPARC related modular calcium binding 1 | 22.1 | NM_001034852 |
| SLC28A3 | solute carrier family 28 (sodium-coupled nucleoside transporter), member 3 | 21.7 | NM_022127 |
| BARX2 | BarH-like homeobox 2 | 21.6 | NM_003658 |
| FGFR3 | fibroblast growth factor receptor 3 | 20.9 | NM_000142 |
| PDE3A | phosphodiesterase 3A, cGMP-inhibited | 20.1 | NM_000921 |
| ATP13A4 | ATPase type 13A4 | 20.1 | NM_032279 |
| AMBP | alpha-1-microglobulin/bikunin precursor | 19.4 | NM_001633 |
| SCN8A | sodium channel, voltage gated, type VIII, alpha | 19.3 | NM_014191 |
| KRT80 | keratin 80 | 19.2 | NM_182507 |
| NRAP | nebulin-related anchoring protein | 19.0 | NM_198060 |
| FGFR2 | fibroblast growth factor receptor 2 | 18.7 | NM_000141 |
| DZIP1L | DAZ interacting protein 1-like | 18.6 | NM_173543 |
| CFTR | cystic fibrosis transmembrane conductance regulator (ATP-binding cassette sub-family C, member 7) | 18.1 | NM_000492 |
| PNLDC1 | poly(A)-specific ribonuclease (PARN)-like domain containing 1 | 18.0 | NM_173516 |

Adult human pancreatic cells were dissociated into single suspension, stained with antibodies and sorted. Gene expression was compared between sorted CD133$^+$CD49f$^{low}$ cells and the presort cells. Data represent the mean from 4 independent sorts. All genes reach confidence limit >80%.

Figure 24:
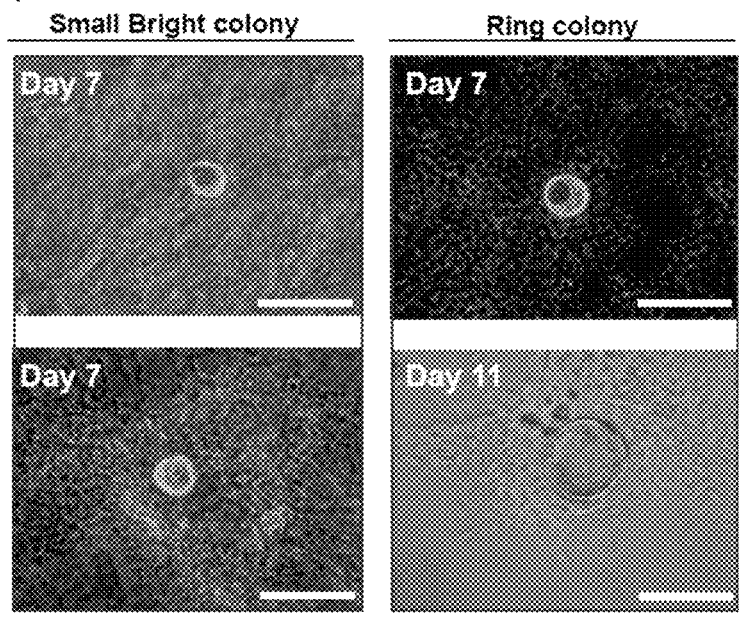
FIG. 24 shows characterization of colonies from human adult pancreas. (A) Photomicrographs of colonies derived from CD133$^+$CD49f$^{low}$ cells. Bars=100 μm. (B) Frequency of colony-forming progenitors is highest in human CD133$^+$CD49f$^{low}$ cells. Data represent mean and standard deviation of the number of day-12 colonies developed from 5,000 sorted cells (n=3). (C) Quantitative RT-PCR analysis of total colonies derived from CD133$^+$CD49f$^{low}$ cells 8 or 21 days post-plating. (D) Individual day-12 colonies were hand-picked and subjected to microfluidic RT-PCR analysis. Data represent the Ct value (expressed as a designated color) of each gene analyzed. Each bar represents a singe colony.
Figure 24:
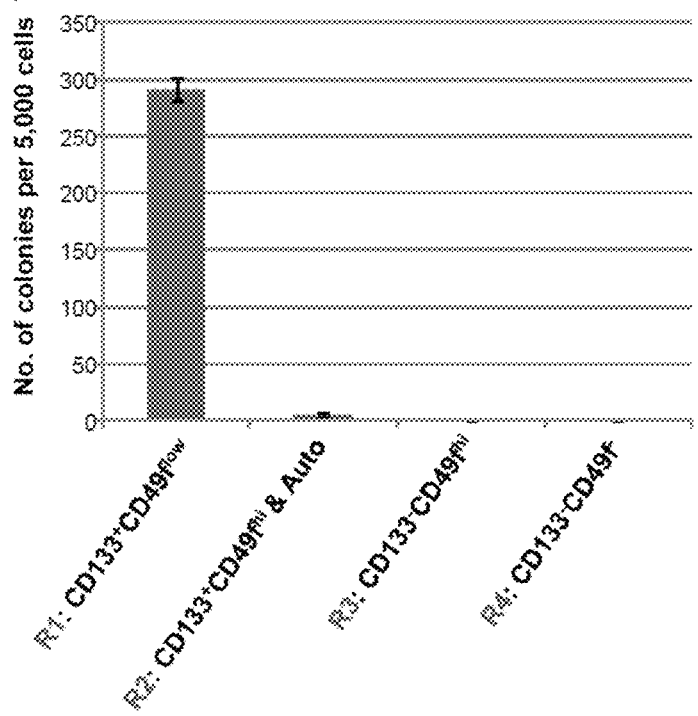
Figure 24:
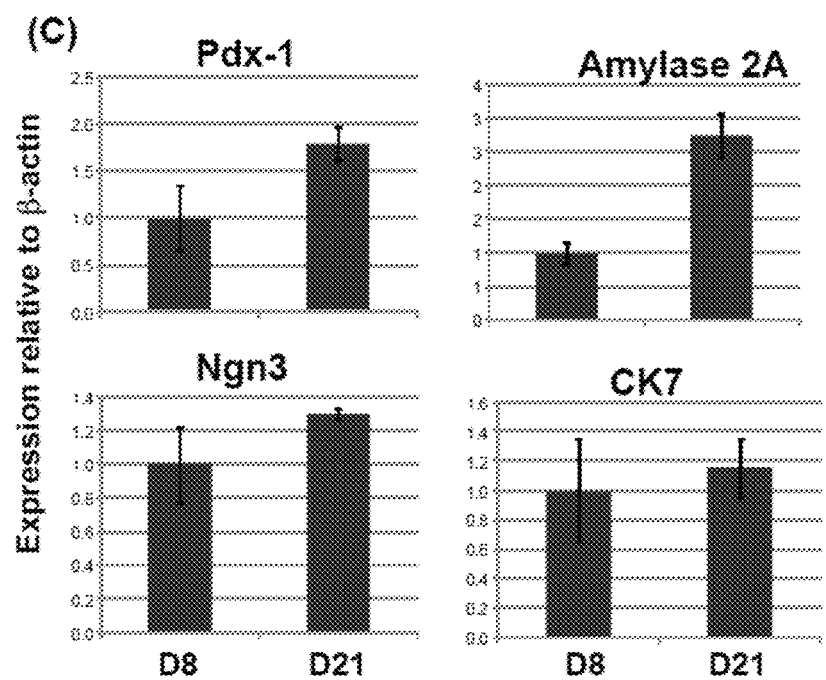
Figure 24:
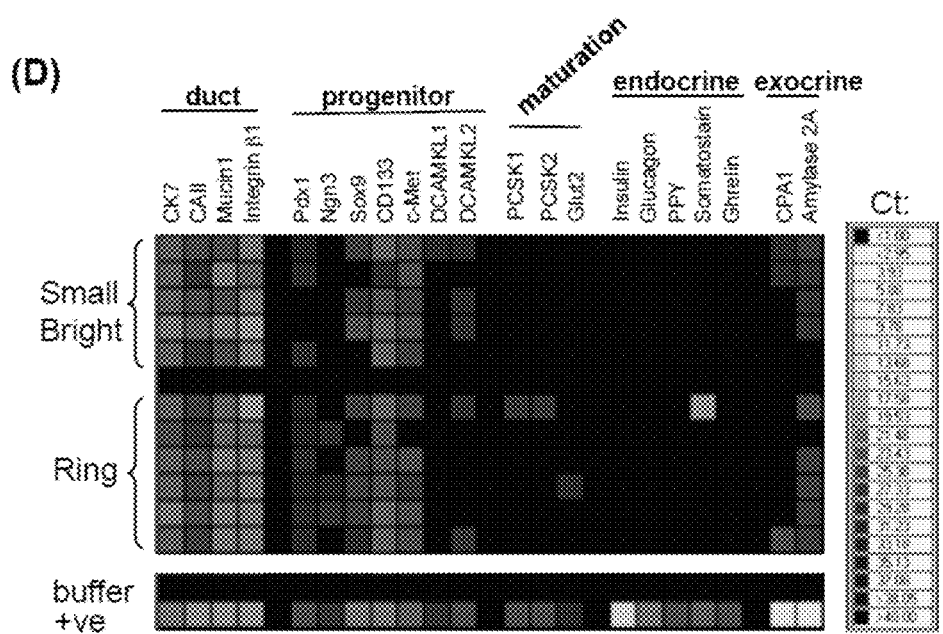

Next it was tested whether sorted CD133$^+$CD49f$^{low}$ cells from human pancreata are capable of forming colonies. CD133$^+$CD49f$^{low}$ cells consistently gave rise to the highest number of colonies in vitro (FIG. 24A). About 6.6% of CD133$^+$CD49f$^{low}$ cells formed colonies within 12 days of plating (FIG. 24B). However, in contrast to the results in mice, most (97%) of the human colonies remained as Small Bright colonies, even after long-term (>21 days) culture. Although an increase in Pdx-1 or amylase 2A expression was observed in the cultures on day 21 compared to day 8, the expression of endocrine genes was not detected (FIG. 24C). Microfluidic single-colony RT-PCR analyses revealed that, similar to mouse colonies, ductal cell markers were expressed at high levels in the human cells, while acinar markers were expressed at lower levels (FIG. 24D). These results suggest that the transition from Small Bright colonies to Ring colonies is blocked or slowed in human cells, which may be due to suboptimal storage or culture conditions for the human cadaveric ducts, variations in the developmental kinetics of human versus mouse cells, or the prevalence of fewer ductal cells with the potential to differentiate into endocrine cells.

Discussion

Figure 15:
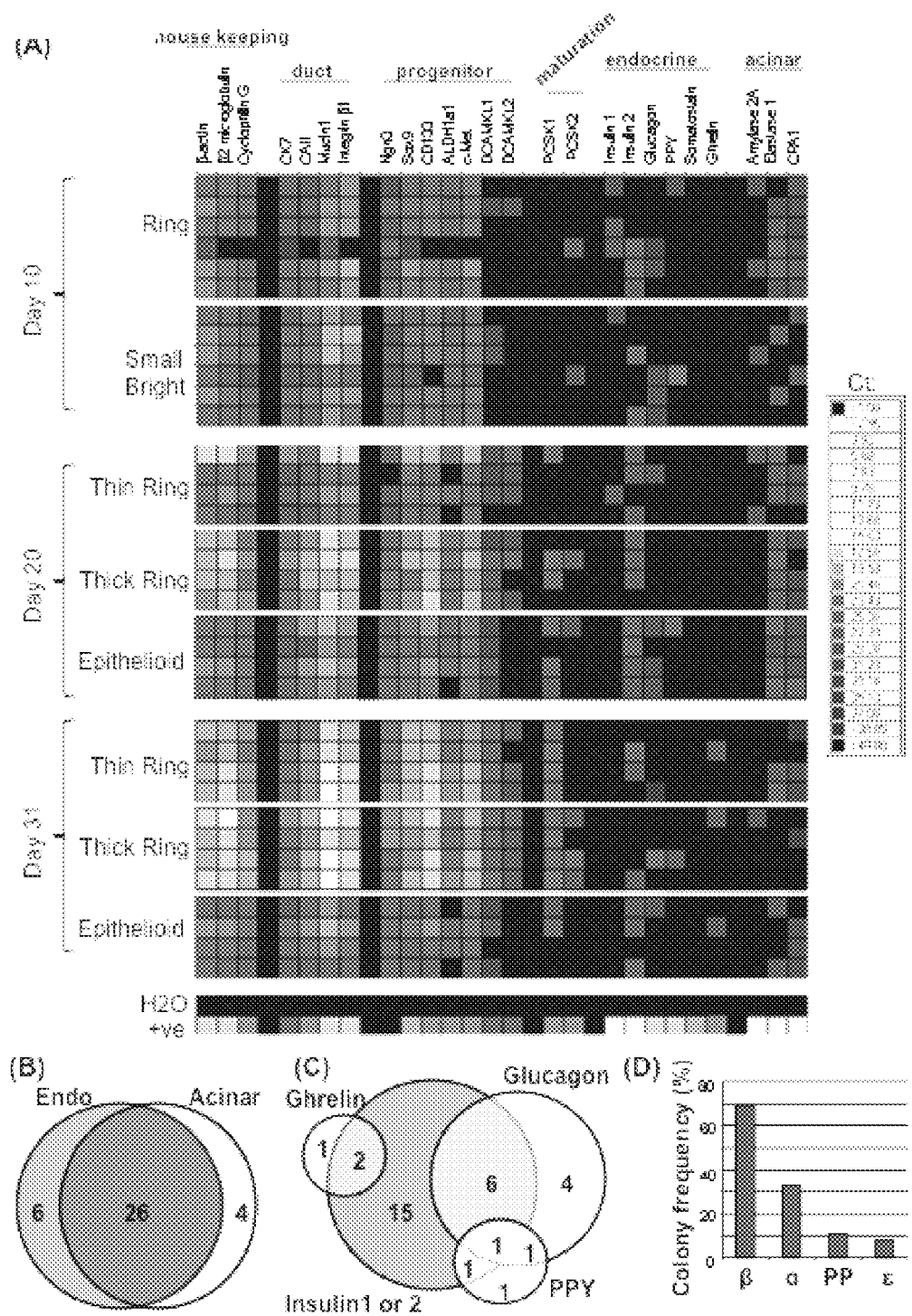
FIG. 15 shows characterization of individual colonies derived from murine adult pancreatic ductal progenitors as a function of the expression of various indicated markers. (A) Single colonies at designated time points were handpicked and subjected to microfluidic RT-PCR analysis using designated TaqMan gene probes. Data represent the Ct value (expressed as a designated color) of each gene analyzed. (B-C) Lineage composition analyses of the 36 colonies shown in (A). (B) If a colony is expressing any of the six or three gene probes for endocrine (endo) or acinar cells, respectively, its progenitor is considered to be positive for that lineage potential. (D) Analysis of the prevalence of colonies expressing endocrine genes. Data represent two experiments with similar trends.

The present study shows that single murine ductal cells self-renew (FIG. 20 and Table 3) and differentiate into multilineage cystic structures in vitro (FIGS. 15 and 17). Because self-renewal and differentiation are fundamental properties of stem cells, this study therefore shows that adult pancreatic ducts harbor stem and progenitor cells. Approximately 10% of the murine pancreas is composed of ducts (FIG. 9D), and about 17% of ductal cells can form colonies (FIG. 13F). Of these, around 70% are multipotent (FIG. 15B). Therefore, these newly identified ductal multipotent progenitor cells comprise about 1.19% of all adult murine pancreatic cells. In contrast, centroacinar (Rovira et al. 2010) and insulin$^+$ (Seaberg et al. 2004; Smukler et al. 2011) progenitor cells comprise approximately 0.3% and 0.004% of the total pancreatic cells, respectively.

It is generally believed that adult pancreatic ducts are composed of a homogenous population of mature cells. Under this premise, the in vitro differentiation of duct to endocrine cells has been interpreted as a "de-differentiation" event in which mature duct cells first become progenitors and then undergo a full or partial epithelial-mesenchymal transition to form endocrine cells (Li et al. 2010). However, the current study demonstrates that only a small proportion of ductal cells can form colonies—challenging the notion that ductal cells are homogeneous. The fact that the prevalence of colony-forming ductal cells is altered in response to injury (FIG. 21C) further indicates that these cells are heterogeneous. These results, coupled with the rapidity of colony formation in the 3-D assay, strongly suggest that pre-existing ductal progenitors simply differentiate when induced, and that the de-differentiation of mature ductal cells is unlikely.

While individual adult ductal stem cells preferentially and robustly differentiate into ductal-like cells in the 3-D colony assay, the differentiation of endocrine and acinar cells occurs infrequently within single colonies (FIGS. 15 and 17). This result is consistent with prior findings showing that CA19.9$^+$ human ductal cells have a limited, but positive, endocrine potential in vitro 8 and in vivo (Yatoh et al. 2007). This inefficiency may reflect sub-optimal culture conditions that interfere with the ability of ductal progenitors (particularly in human cells) to efficiently express the endocrine lineage, or an intrinsic property of steady-state adult ductal progenitors. Regardless, the results described herein suggest that adult ductal stem and progenitor cells may be a suitable starting material for the generation of beta-like cells in vitro for the treatment of T1D, an approach that has long been championed by others (Bonner-Weir et al. 2000; Gao et al. 2003; Hao et al. 2006).

PDL injury elicits ductal epithelium damage, acinar cell death and macrophage infiltration, and results in acute pancreatitis (Walker et al. 1992). It is therefore reasonable to assume that ductal cells will, in addition to acinar cells, be one of the major cell types needed for repair. Several studies have consistently demonstrated the extensive formation of Sox9-expressing ductal structures in vivo following PDL (Kopp et al. 2011a; Pinho et al. 2011; Walker et al. 1992). The increased proportion of non-colony-forming to colony-forming Sox9+ ductal cells in PDL-treated mice, as well as the increase in size of the colonies formed from these ductal progenitors (FIG. 21), also support this assumption.

In summary, this study shows that single murine adult ductal cells possess stem cell activity in vitro. They self-renew and differentiate, and build organoid, cystic multi-lineage colonies in the 3-D colony assay in the absence of niche cells. As described in Example 3 below, the 3-D pancreatic colony assay may be used to determine the capacity for self-renewal, proliferation and differentiation of single ductal stem cells to be altered by extrinsic, intrinsic or reprogramming signals that favor β-cell commitment.

Example 3: R-Spondin-1 Enhances Self-Renewal and Differentiation of Single Ductal Pancreatic Stem Cells from Adult Mice In Vitro As discussed in Example 2 above, adult murine pancreatic ducts harbor stem cells. To determine the factors which regulate the self-renewal and differentiation of these cells, the studies described below were conducted. The ability to generate or establish a population of adult pancreatic stem cells is of great interest because of their potential to generate unlimited numbers of insulin-secreting endocrine β-cells for cell-replacement therapy of diabetes. To further this aspiration, an in vitro assay was designed that allows single cells to be analyzed for their ability to both self-renew and differentiate—the defining properties of a stem cell (See Example 2). Using this assay, a fraction of CD133$^+$Sox9-EGFP$^+$ murine pancreatic ductal cells were found to both self-renew and give rise to multi lineage colonies comprising ductal, acinar and endocrine lineage cells. Because single cells were analyzed, these results demonstrated that ductal cells are heterogeneous and that only a small sub-population of ductal cells exhibits stem cell characteristics. The differentiation of these newly identified stem cells, however, was weighted toward the ductal lineage and their commitment to the endocrine and acinar lineages was minimal. In the study described below, it was determined that the differentiation of these stem cells can be modified by changing the microenvironment of the cells, such as by adding exogenous growth factors.

R-Spondin 1 has been shown to be a factor that regulates the function of adult stem cells in the small intestine (Kim et al. 2005; Zhao et al. 2007a; Sato et al. 2009; Ootani et al., 2009; de Lau et al. 2011), an organ that shares the same developmental origin as pancreas. Thus the effect of R-Spondin 1's influence on adult ductal pancreatic stem cells was investigated as described herein. R-Spondin 1 enhances, and Dkk1 inhibits, the self-renewal of ductal pancreatic stem cells in vitro. It was also found that R-Spondin 1 promotes the emergence of bi-potential progenitors from ductal stem cells. These committed progenitor cells can be subsequently matured in the absence of exogenous R-Spondin 1 into glucose responsive, insulin-secreting cells. Thus, adult pancreatic ductal stem cells may be a source of therapeutic β-cells for treatment of diabetes.

Additional Materials and Methods

Animals. Sox9-EGFP (Tg(Sox9-EGFP)209Gsat/Mmcd) mice (Gong et al. 2003) were obtained from the Mutant Mouse Regional Resource Centers (MMRRC) and maintained on a CD1 genetic background.

Cell culture and in vitro colony assay. Freshly sorted adult (2 to 4-month-old) ductal cells were cultured in methylcellulose-based colony culture medium that contained Matrigel as previously described (Winkler et al. 2011). A total of 2,500 freshly sorted CD133+Sox9-EGFP+cells were routinely plated per well in triplicate. For the Endo/Acinar colony assay described in FIG. 30, Matrigel was replaced with an artificial extracellular matrix protein containing the aECM that includes the laminin-IKVAV (SEQ ID NO:1) domain (FIG. 1) at 100 μg/ml as described in Example 1 above. Unless specified otherwise, recombinant murine R-Spondin 1 and Dkk1 (R&D) were used at 750 μg/ml or 200 ng/ml, respectively.

Results

Figure 25:
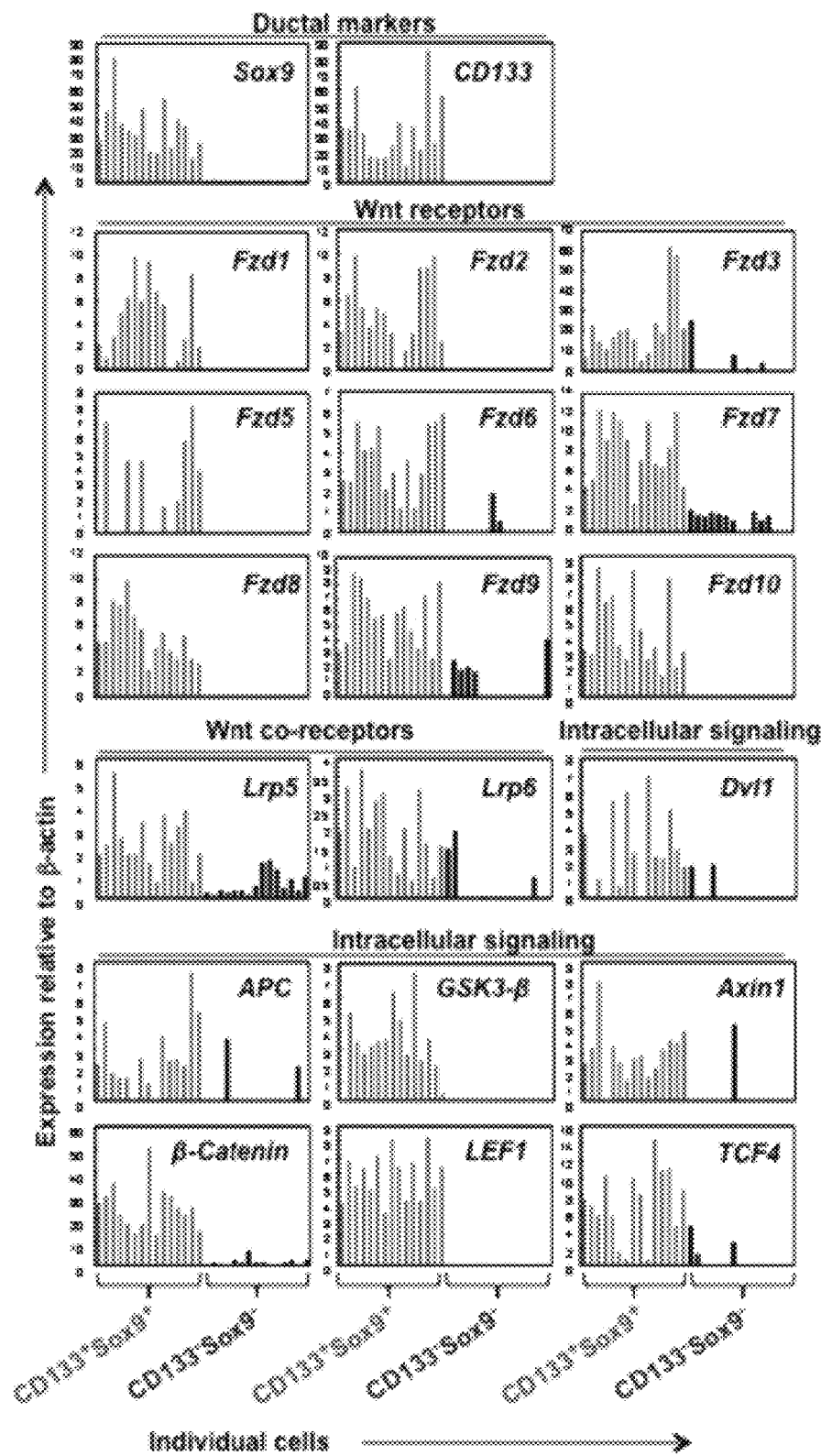
FIG. 25 is a series of analyses illustrating that single murine adult pancreatic ductal cells express Wnt receptors and intracellular signaling molecules as indicated. Adult pancreata from Sox9-EGFP transgenic mice were dissociated into single-cell suspension, stained with anti-CD133 antibody, and subjected to fluorescence activated cell sorting. Single CD133$^+$Sox9-EGFP$^+$ (duct) or CD133Sox9-EGFP— (non-duct) cells were handpicked (15 each) and subjected to single-cell microfluidic qRT-PCR analysis using the designated TaqMan gene probes. Data represent two experiments with similar trends.

Single adult pancreatic ductal cells express Wnt signaling components. Murine adult ductal cells express both CD133 and Sox9. To test whether canonical Wnt signaling components are expressed in ducts, a total of 15 sorted CD133$^+$Sox9-EGFP$^+$ cells were individually handpicked and subjected to microfluidic quantitative RT-PCR (qRT-PCR) analysis. Fifteen single CD133-Sox9-EGFP— (non-duct) cells were also analyzed as controls (FIG. 25). 100% of the single CD133$^+$Sox9-EGFP$^+$ cells expressed higher levels of CD133 and Sox9, compared to CD133$^-$Sox9-EGFP$^-$ cells (FIG. 25). Furthermore, 100% (15 out of 15) of CD133$^+$Sox9-EGFP$^+$ cells expressed Frizzled 3, 6, 7, 8, 9, and 10, as well as Lrp 5, Lrp 6, beta-catenin, LEF1, and Tcf4; 93% expressed Frizzled 1 and 2, GSK3-beta, and Axin1; 87% expressed APC; and 53% expressed Frizzled 5. In sharp contrast, CD133—Sox9-EGFP— cells expressed few or none of these Wnt family genes. In addition, immunohistochemical staining of adult pancreas revealed that the expression of the LrpS/6 protein overlaps with that of CD133 and EGFP (Sox9) in the ducts. Together, these results demonstrate that adult ductal cells express Wnt receptors and signaling components.

Figure 26:
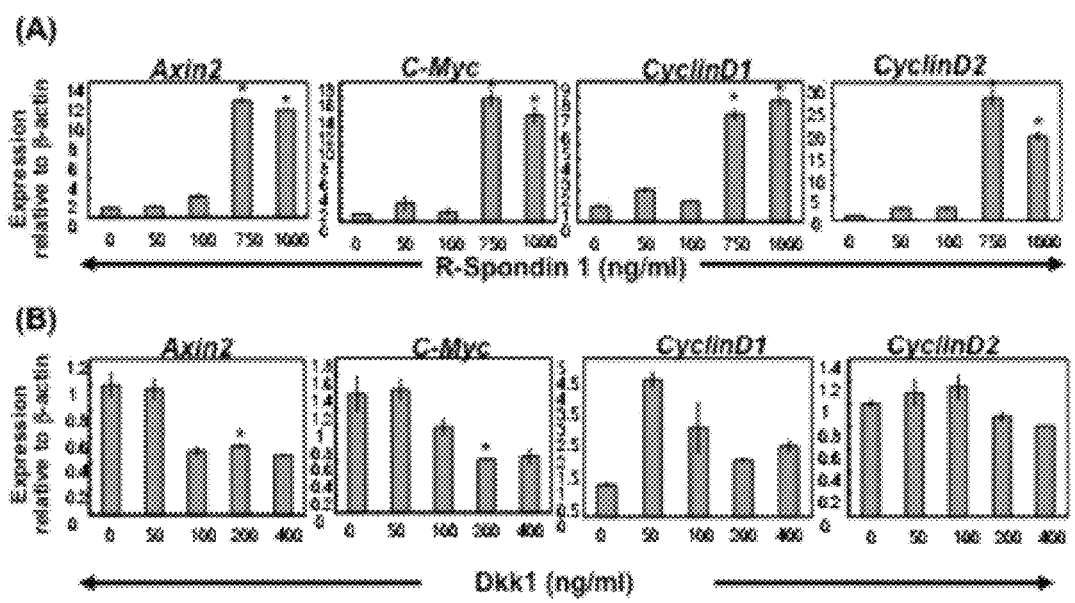
FIG. 26 is a series of analyses illustrating dose-response effects of R-Spondin 1 or Dkk1 on Wnt target genes in cells derived from ductal progenitors. CD133$^+$Sox9-EGFP$^+$ cells were plated in the presence of the designated amounts of recombinant R-Spondin 1 (A) or Dkk1 (B). Three weeks later, total cells were procured and analyzed by qRT-PCR analysis with the designated TaqMan probes. Data represent two experiments with similar trends. This number is different compared to no-addition control at P<0.05.

Dose-dependent effects of R-Spondin 1 or Dkk1 on ductal progenitor cells. In the in vitro clonogenic assay discussed above in Example 2, single ductal cells give rise to distinctive cell clusters in the absence of exogenous Wnt signals. Here, it was tested whether Wnt signaling affects the formation of these clusters, which based on their morphology have been termed Ring or Epithelioid colonies. CD133$^+$Sox9-EGFP$^+$ ductal cells were sorted and plated in the presence of varying amounts of exogenous recombinant R-Spondin 1 (a Wnt agonist) or Dkk1 (a Wnt antagonist). Three weeks after plating, the cells were recovered and examined for the expression of Wnt downstream targets. A dose-dependent increase (in the presence of R-Spondin 1) or decrease (in the presence of Dkk1) in the expression of Ainx2, c-Myc, CyclinD1 or CyclinD2 was observed (FIG. 26). Plateau doses for R-Spondin 1 and Dkk1 (750 and 200 ng/mL, respectively) were used in subsequent studies.

Figure 27:
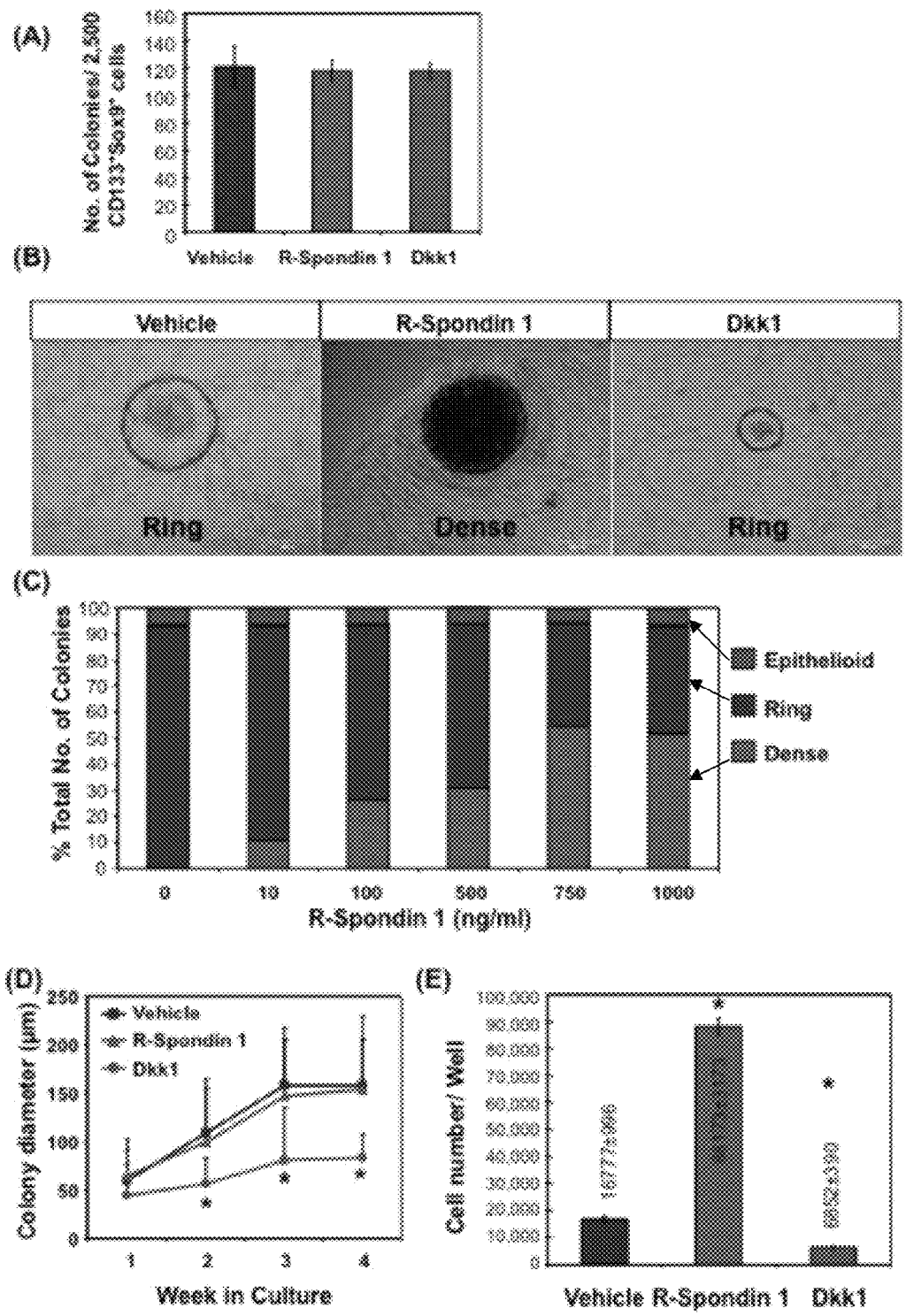
FIG. 27 illustrates that exogenous R-Spondin 1 induces Dense colony formation from ductal progenitors. CD133$^+$Sox9-EGFP$^+$ cells were plated and the resulting colonies were analyzed three weeks later. (A) Colony-forming frequency did not differ in cultures exposed to R-Spondin 1, Dkk1 or vehicle. (B) Representative photomicrographs of designated colonies. (C) The proportion of Dense colonies correlates with R-Spondin 1 dose. (D) Dkk1 inhibits colony size. The diameters of 20 colonies from each group were measured and analyzed at the designated time points. (E) Dense colonies comprise more total cells than other types of colonies. Total cells were recovered, dissociated into single cell suspension, and the number of cells was determined by trypan blue exclusion. Data represent three experiments with similar trends. This number is different compared to vehicle control at P<0.05.

R-Spondin 1 induces "Dense" colony formation from ductal progenitors. Addition of exogenous R-Spondin 1 or Dkk1 to the CD133$^+$Sox9-EGFP$^+$ cells did not change the frequency of colony formation (FIG. 27A), suggesting that the survival of ductal progenitor cells was not affected by the treatment. Consistent with the studies described above and in the absence of Wnt modulators, a fraction of sorted CD133$^+$Sox9-EGFP$^+$ cells gave rise to Ring colonies (FIG. 27B; left panel) after three weeks of culture. (About 90% of total colonies formed from CD133$^+$Sox9-EGFP$^+$ cells in the absence of R-Spondin 1 were Rings, while the rest were Epithelioids). In the presence of R-Spondin 1, however, a new type of colony with a dense core of cells ("Dense") was observed (FIG. 27B; middle panel). The proportion of Dense colonies in the culture exposed to R-Spondin 1 varied in a dose-dependent manner (FIG. 27C). In contrast, cultures treated with Dkk1 formed no Dense colonies and those Ring colonies that did form were smaller than those formed by untreated cells (FIGS. 27B (right panel) and 27D).

The total number of cells recovered also varied between culture conditions. Cultures exposed to R-Spondin 1 had 5-fold more cells after three weeks than did untreated cultures. Conversely, cultures treated with Dkk1 had total cell numbers that were 2-fold lower than untreated cultures (FIG. 27E). Together, these results demonstrate that R-Spondin 1 induces the formation of Dense colonies with higher cellularity, whereas Dkk1 reduces the size of Ring colonies in culture. Epithelioid colonies did not appear to be affected by exogenous R-Spondin 1 or Dkk1.

Figure 28:
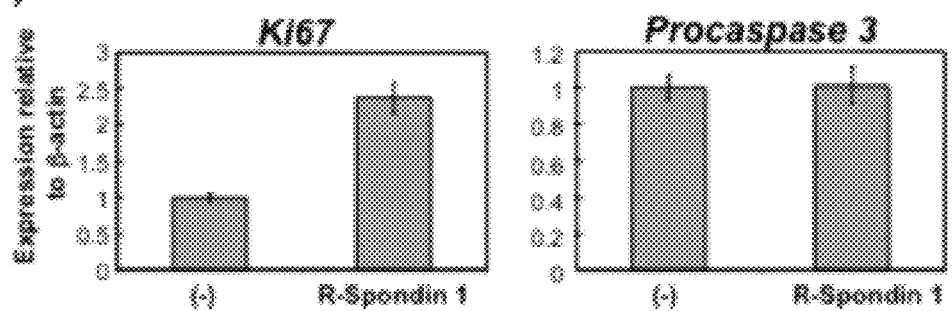
FIG. 28 illustrates that dense colonies exhibit enhanced proliferation. (A) CD133$^+$Sox9-EGFP$^+$ cells were plated in the presence or absence of recombinant R-Spondin 1. Three weeks later, total cells were procured and analyzed by qRT-PCR analysis using the designated TaqMan probes. (B) Immunostaining of individual whole mounted Dense colonies. Data represent two experiments with similar trends.
Figure 28:
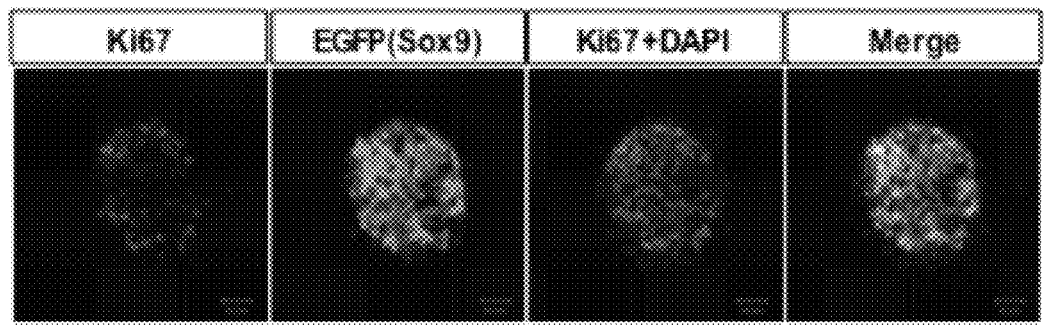

Enhanced proliferation in R-Spondin 1-stimulated Dense colonies. To determine whether the higher cellularity of Dense colonies is due to increased proliferation, the relative expression levels of Ki67 were analyzed in each culture. Expression of Ki67, but not of the apoptosis marker pro-caspase 3, was increased in the presence of R-Spondin 1 (FIG. 28A). Whole-mount immunostaining of individual handpicked Dense colonies with an anti-Ki67 antibody confirmed the presence of actively proliferating cells throughout the Dense colonies (FIG. 28B). Together with the dose-dependent increases observed in the expression of other proliferation markers cMyc, CyclinD1 and CyclinD2 (FIG. 26A) in response to R-Spondin 1, these results demonstrate that R-Spondin 1 enhances the proliferation of cells derived from ductal progenitors.

Figure 29:
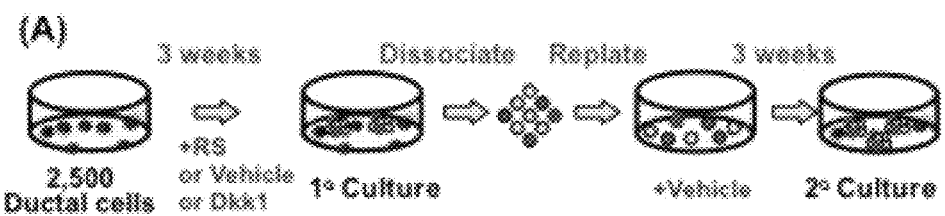
FIG. 29 illustrates that R-Spondin 1 enhances the self-renewal of ductal progenitors. (A) CD133$^+$Sox9-EGFP$^+$ cells were plated in the presence of designated factors. Three weeks later, total cells were procured, dissociated into single-cell suspension and replated into secondary culture in the absence of exogenous factors. The number of secondary colonies was ascertained three weeks after replating. (B) As illustrated in the upper panel, CD133$^+$Sox9-EGFP$^+$ cells were plated in the presence of R-Spondin 1. Three weeks later, total colonies from each well (n=4 for each group) were procured, dissociated and replated in the presence of designated factors. After two weeks, the colonies were counted and all cells were procured, dissociated, counted, and replated. Counting, procurement, dissociation and replating procedure was repeated a total of four times. The number of total resulting colonies was analyzed (lower panel). Data represent two experiments with similar trends. This number is different compared to vehicle control at $P<0.05$.
Figure 29:
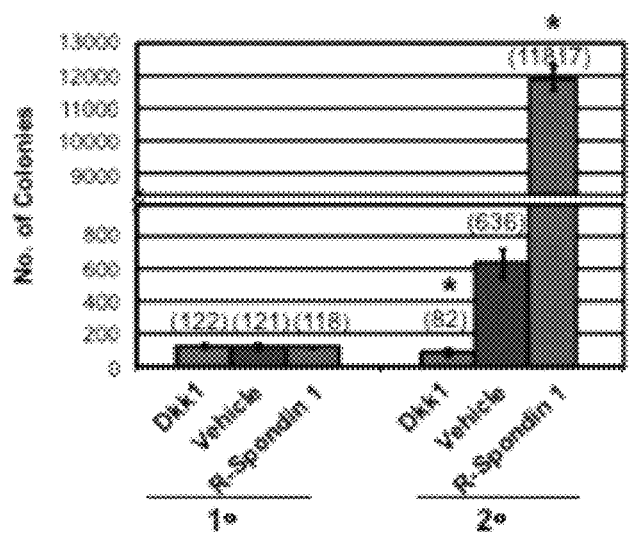
Figure 29:
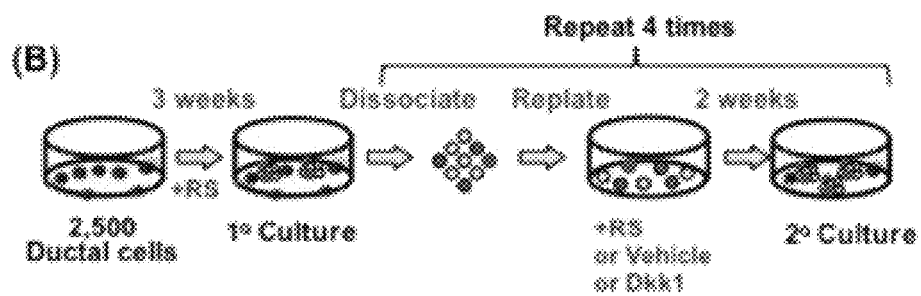
Figure 29:
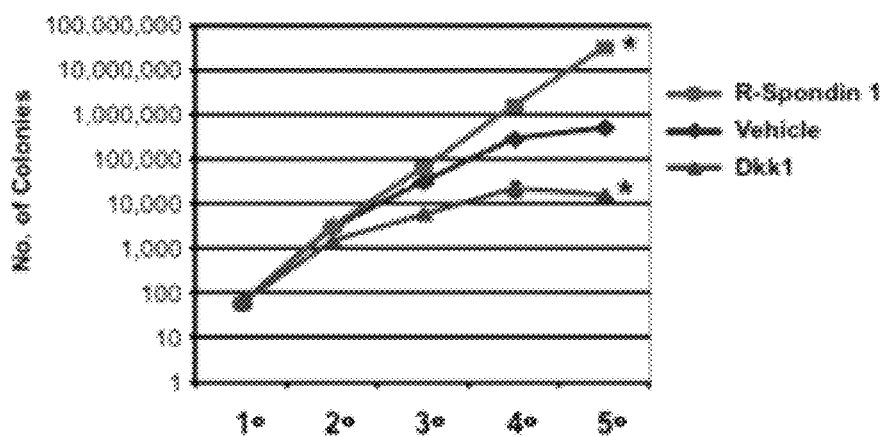

R-Spondin 1 enhances, while Dkk1 reduces, the self-renewal of ductal progenitors. To test whether R-Spondin 1 also regulates self-renewal, serial replating experiments were performed (FIG. 29). Freshly sorted $CD133^+Sox9-EGFP^+$ ductal cells were plated in the presence of either exogenous R-Spondin 1, vehicle, or Dkk1 and cultured for three weeks. The resulting colonies were dissociated into a single-cell suspensions and replated into an untreated colony cultures to again assess their colony-forming ability. As observed in FIG. 27A, the frequency of colony formation in primary cultures by freshly sorted $CD133^+Sox9-EGFP^+$ cells was not affected by the various treatments (FIG. 29A). However, compared to vehicle-treated controls, cells from primary cultures treated with R-Spondin 1 formed 18-fold more colonies in untreated secondary cultures. In contrast, Dkk1 treatment of the primary culture caused a 8-fold reduction of colony-forming progenitors (FIG. 29A). Replating of individually handpicked primary Dense colonies demonstrated that all of these colonies initiated secondary colonies. Together, these results demonstrate that R-Spondin 1 enhances, and Dkk1 inhibits, the self-renewal of ductal stem cells during primary culture. Finally, a 5-fold increase in the number of untreated colony-forming cells was observed in secondary compared to primary culture (FIG. 29A; middle bars, vehicle). This indicates that ductal progenitors replicate even in the absence of exogenous R-Spondin 1 and suggests that there are endogenous signals for self-renewal in the basal culture media.

To test whether ductal stem cells can sustain long-term self-renewal, colonies obtained from primary cultures treated with exogenous R-Spondin 1 were dissociated and serially replated over an additional four generations in the presence of either R-Spondin 1, vehicle, or Dkk1. Continuous exposure of colonies to exogenous R-Spondin 1 over 5 generations induced exponential growth of Dense colony-forming progenitor cells (FIG. 29B), and led to an $5\times10^5$-fold net expansion of colony-forming cells over 11 weeks. Interestingly, Dkk1 did not immediately inhibit self-renewal of R-Spondin 1-stimulated primary colonies, but did so gradually over a series of passages (FIG. 29B). These results demonstrate that R-Spondin 1 stimulated primary colonies contain long-term culture initiating stem cells.

R-Spondin 1 enhances the formation of differentiation-competent committed progenitor cells. To determine whether R-Spondin 1 affects differentiation, cells from primary cultures with or without R-Spondin 1 were analyzed by qRT-PCR for the expression of progenitor cell markers. R-Spondin 1 treatment enhanced the expression of markers for early (Pdx1, Nkx6.1), endocrine (Ngn3, neuroD1, Pax4), and acinar progenitors (Ptf1a). These results suggest that R-Spondin 1 not only stimulates the self-renewal of ductal stem cells but also supports their differentiation into early pancreatic endocrine and acinar progenitor cells.

In order to quantitate the number of endocrine and acinar progenitors arising from R-Spondin 1 treatment, another clonogenic assay that utilizes an artificial extracellular matrix protein to replace Matrigel and supports the differentiation of endocrine progenitors was used, as described above in Example 2. This assay relies on a bacterially produced artificial extracellular matrix containing the laminin-IKVAV sequence (SEQ ID NO:1) (also designated laminin hydrogel), which supports the robust development of endocrine cells, rather than on Matrigel, which preferentially induces the differentiation of ductal cells.

A total of 10 Dense colonies were handpicked, pooled, dissociated into a single cell suspension and plated into a laminin hydrogel colony assay in the absence of exogenous R-Spondin 1. A new type of colony emerged after 2 weeks of culture. These colonies were small (~30-40 um in diameter), and were not light-reflective or cystic (FIG. 30A; photomicrograph). This type of colony was named "Endo/Acinar" to indicate its lineage composition (see next section). Among total dissociated cells from R-Spondin 1 treated primary colonies, 3.17±0.01% formed Endo/Acinar colonies in secondary cultures, compared to 0.60±0.01% of cells from untreated colonies, demonstrating that R-Spondin 1 enhances the generation of Endo/Acinar colony forming progenitors during the primary culture.

Figure 30:
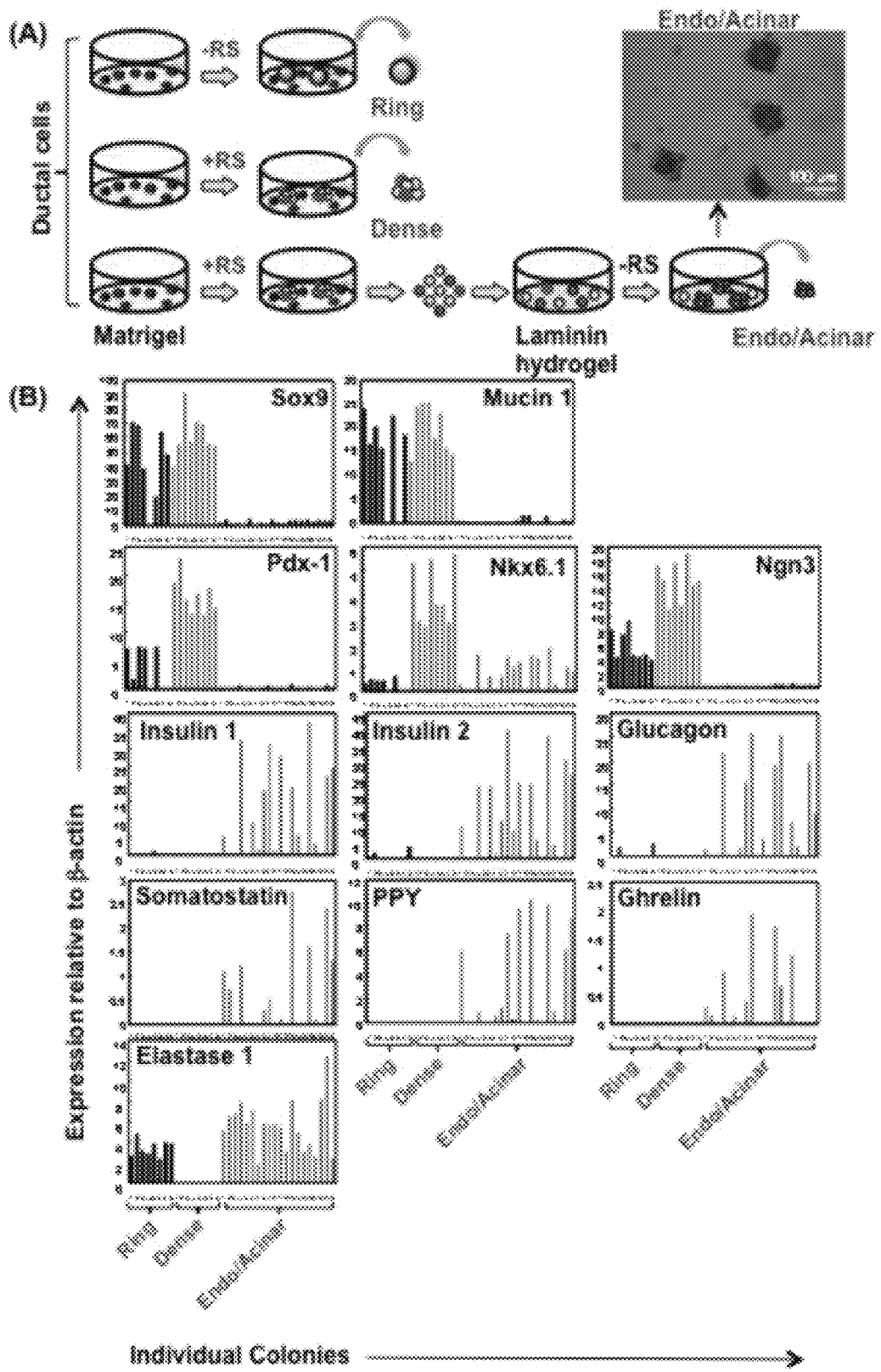
FIG. 30 is a comparison between the expression of various pancreatic markers in single Dense, Endo/Acinar or Ring colonies, as indicated. Dense colonies have enhanced expression of committed pancreatic progenitor cell markers, whereas Endo/Acinar colonies express higher levels of terminally differentiated lineage markers for endocrine and acinar cells. A single Ring (n=8), Dense (n=8), or Endo/Acinar (n=21) colony, generated as illustrated in (A), was handpicked and subjected to microfluidic qRT-PCR analysis using the designated TaqMan probes (B). A representative photomicrograph in (A) shows the morphology of Endo/Acinar colonies under a light microscope two weeks after plating dissociated Dense colonies. Abbreviations: in the presence of exogenous R-Spondin 1 (+RS); in the absence of exogenous R-Spondin 1 (−RS). (C&D) Immunostaining of individual whole-mounted Dense or Endo/Acinar colonies. Bars=50 µm. Data represent two experiments with similar trends.
Figure 30:
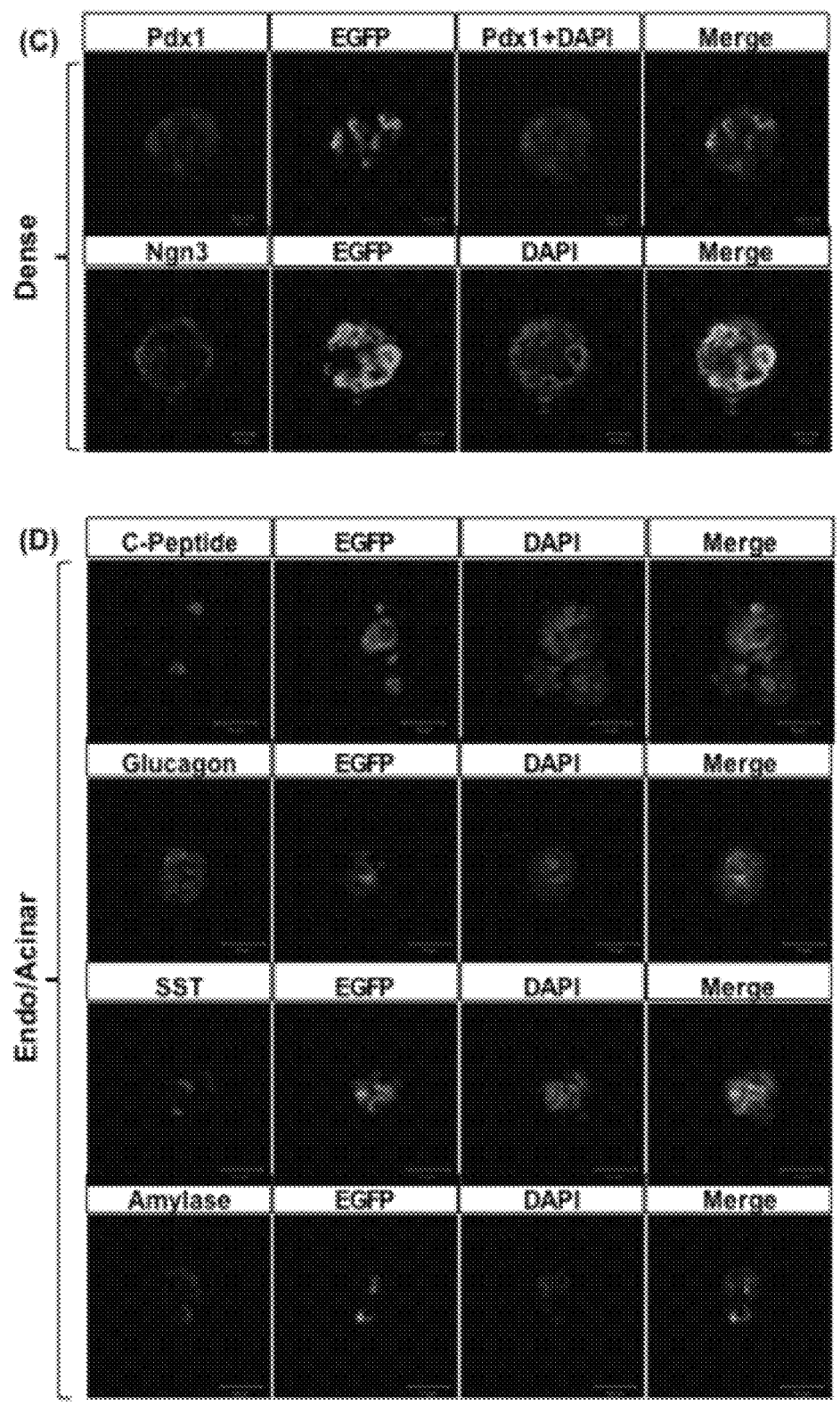

Characterization of single Dense or Endo/Acinar colonies. To determine the lineage composition of individual Dense or Endo/Acinar colony, single colonies were handpicked and subjected to microfluidic qRT-PCR analysis (FIG. 30). Individual Ring colonies that had never been exposed to exogenous R-Spondin 1 were used as controls. The levels of expression of ductal cell markers (Sox9 and mucin 1) were similar between Ring and Dense colonies, suggesting that both types of colonies contain ductal cells. Electron-microscopy analysis also confirmed the presence of ductal-like cells with multinucleated nuclei and microvilli in three-week-old Dense or Ring colonies. The levels of expression of multipotent (Pdx-1 and Nkx6.1) and endocrine progenitor (Ngn3) cell markers were higher in Dense colonies than in Ring colonies (FIG. 30B), suggesting that R-Spondin 1 enhances the generation of committed progenitor cells.

In contrast to Ring and Dense colonies, Endo/Acinar colonies expressed minimal levels of ductal and progenitor cell markers, but higher levels of terminally differentiated endocrine (insulin 1, insulin 2, glucagon, somatostatin, PPY and ghrelin) or acinar (elastase 1) lineage markers, demonstrating that the single progenitor cells that give rise to Endo/Acinar colonies are bi-potent for endocrine and acinar lineages.

Figure 31:
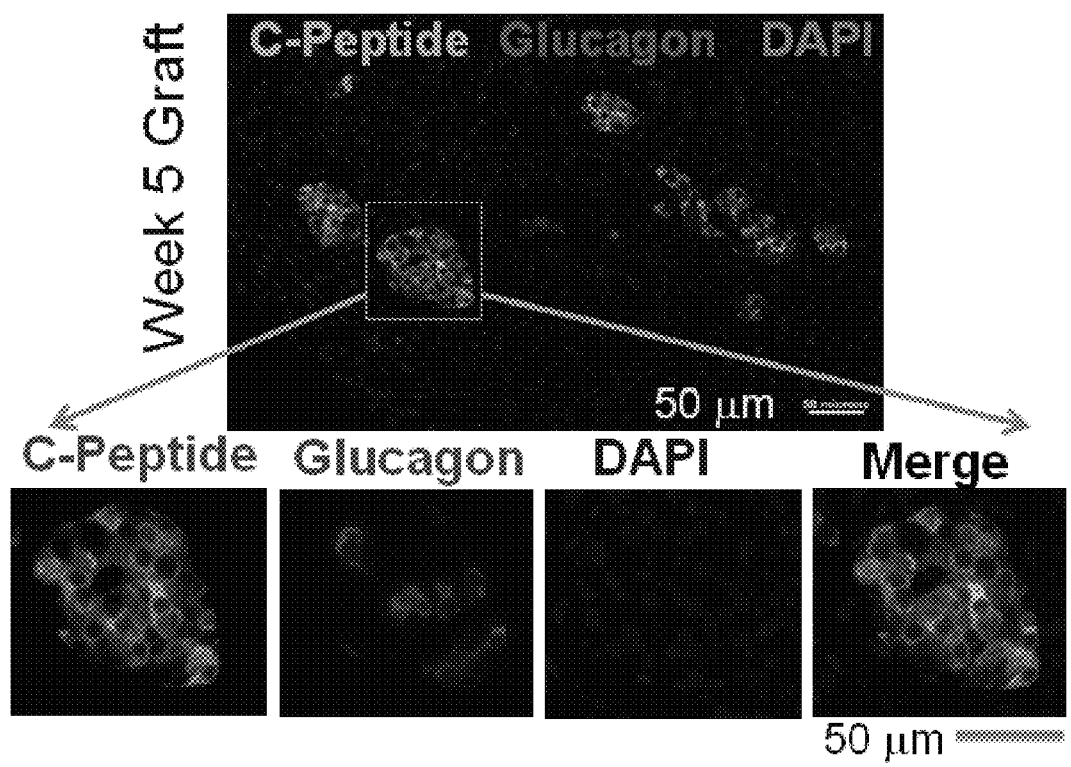
FIG. 31 shows that Dense colonies implanted in streptozotocin-treated diabetic NODSCID mice gave rise to C-peptide⁺glucagon⁻ cells at five weeks post transplantation. Staining with control antibodies was negative (not shown). Bar=50 µm

Whole-mount immunostaining of individual handpicked colonies confirmed the presence of Pdx-1 and Ngn3 in Dense colonies (FIG. 30C), and C-peptide, glucagon, somatostatin and amylase in Endo/Acinar colonies (FIG. 30D). Also, Dense colonies implanted in streptozotocin-treated diabetic NODSCID mice gave rise to C-peptide$^+$glucagon$^-$ cells at five weeks post transplantation (FIG. 31). C-peptide is a surrogate marker for de novo synthesized insulin. These results clearly demonstrate that R-Spondin 1 supports the formation of endocrine and acinar progenitors from ductal stem cells, and that the endocrine and acinar progenitors can subsequently differentiate into endocrine and acinar cells in the absence of exogenous R-Spondin 1.

Figure 32:
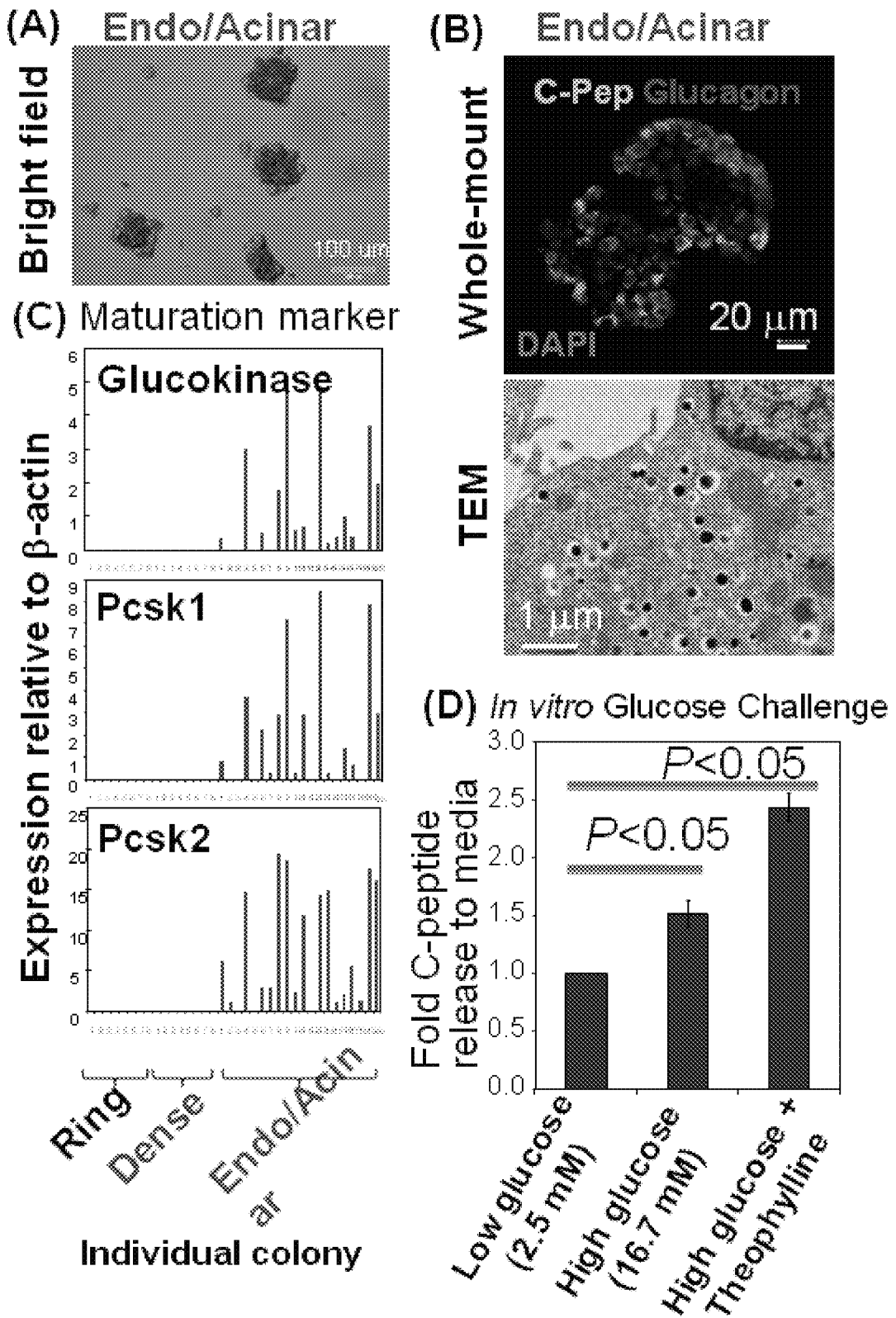
FIG. 32 shows that Endo/Acinar colonies contain C-Peptide+glucagon− cells, express beta-cell maturation markers, and are glucose responsive in C-peptide secretion in vitro. (A) Photomicrograph of Endo/Acinar colonies. CD133+Sox9/EGFP+ cells were plated in Matrigel colony assay for 3 wks. The resulting colonies collected, dissociated, and replated into laminin colony assay for 2 wks, which resulted in Endo/Acinar colony formation. (B) Whole-mount immunostaining (upper) and transmission electron microscopy study (lower) of a 2-wk-old colony. (C) Microfluidic qRT-PCR analysis of single colonies. (D) C-peptide release to media over a 2 h sequential incubation of designated conditions. Secretion in low concentrations of glucose is set to 1.
Figure 33:
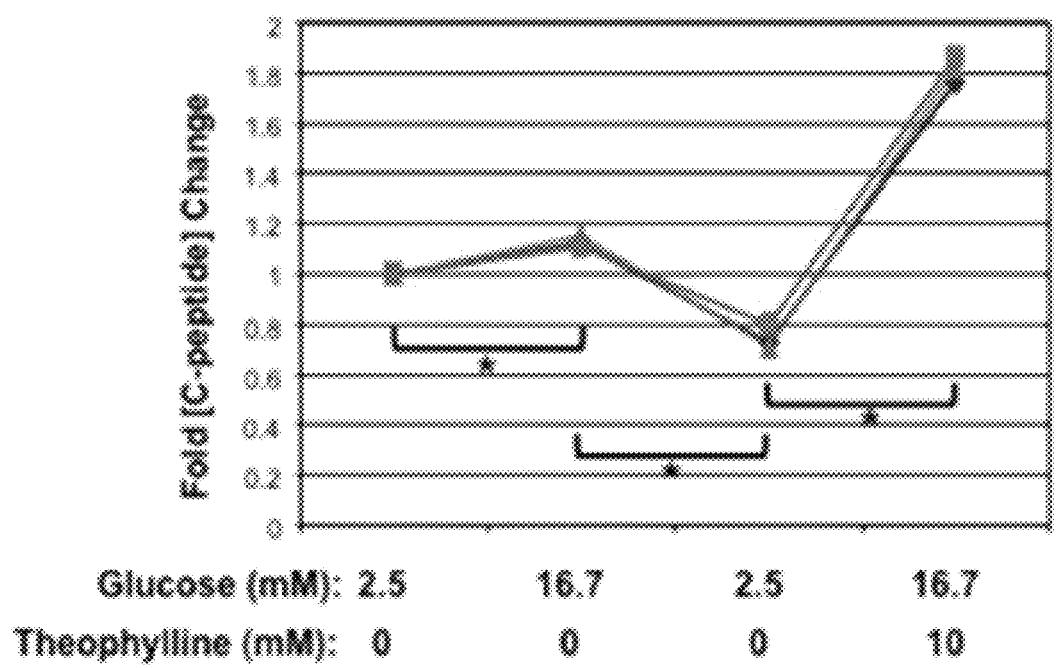
FIG. 33 illustrates that β-cells in Endo/Acinar colonies secrete insulin in response to glucose. Pooled Endo/Acinar colonies were subjected to an in vitro glucose challenge assay. Each line represents a well with a pool of 100 colonies. Wells were analyzed in triplicate. Data represent two experiments with similar trends. *These numbers are different at $P<0.05$ by paired Student's t test.

Differentiated β-cells respond to glucose and secrete insulin in vitro. Two week old Endo/Acinar colonies gave rise to C-peptide+glucagon– cells (FIG. 32A, B). Microfluidic qRT-PCR analysis revealed that 70% (14/20) of the individual Endo/Acinar colonies expressed glucokinase and 85% (17/20) expressed pro-hormone converts (Pcsk1 or 2) (FIG. 32C). As glucokinase and Packs are β-cell maturation markers, this finding suggests that these in vitro differentiated insulin$^+$ cells might be capable of secreting insulin in response to D-glucose (glucose). To test this, Endo/Acinar colonies were handpicked, pooled and incubated overnight with low concentrations (2.5 mM) of glucose. The next day, colonies were washed and subjected to sequential low (2.5 mM), high (16.7 mM), low and, finally, high concentrations of glucose plus theophylline, a camp potentiator that maximizes insulin release. The amount of C-peptide in the media was determined by ELISA. Endo/Acinar colonies responded dynamically to glucose stimulation by secreting C-peptide into the media (FIG. 33). Additionally, similar results were shown with Endo/Acinar colonies that were subjected to 2 hour sequential incubations of designated glucose and theophylline conditions (FIG. 32D). These results demonstrate that clonal adult ductal stem cells can differentiate and mature into functional β-cells in vitro.

Discussion

In this study, it was demonstrated that R-Spondin 1 supports not only the self-renewal of clonal ductal stem cells, but also their differentiation into endocrine or acinar progenitors. Importantly, the endocrine progenitors could terminally differentiate in the absence of exogenous R-Spondin 1 into functionally mature β-cells. These results clearly show that a factor such as R-Spondin 1 can regulate the properties of adult ductal pancreatic stem cells in vitro.

The visceral fat surrounding the pancreas likely expresses high levels of R-Spondin 1, thus it is possible that there is crosstalk between the fat tissue and pancreatic progenitor cells during regeneration.

As described in Example 2 above, Ring and Epithelioid colonies were derived from single adult ductal cells. In this Example, two additional colony types were observed: Dense (FIG. 27B) and Endo/Acinar (FIG. 30A). The Dense colonies appear only after R-Spondin 1 stimulation. They can repeatedly initiate secondary colonies (for at least five generations) and they express higher levels of Ki67, Pdx-1, Ngn3, and Ptf1a than do Ring colonies that have not been exposed to R-Spondin 1. Dense colonies also contain ductal cells, as shown by their multi-lobed nuclei, microvilli and high levels of expression of mucin 1. Together, these results demonstrate that a single Dense-colony forming unit (CFU-Dense)—that is, the progenitor cell that gives rise to a Dense colony—can undergo self-renewal, proliferation and multi-lineage commitment to ductal, endocrine and acinar progenitor cells. Thus, Dense-colony-forming units possess stem cell characteristics.

When compared to Ring- and Epithelioid-colony-forming units described above in Example 2, Dense-colony-forming units observed in this Example likely represent an overlapping population in the pancreatic ducts for at least the following reasons: (i) R-Spondin 1 treatment did not alter the prevalence of total colony forming progenitors in a primary culture of freshly sorted CD133$^+$Sox9-EGFP$^+$ ductal cells (FIG. 27A); (ii) only Ring and Epithelioid colonies formed in the absence of R-Spondin 1 (See Example 2); and (iii) in the presence of R-Spondin 1, 55% of colonies were Dense and the rest were either Ring or Epithelioid (FIG. 27E). Therefore, at least some Dense colonies arise from either Ring or Epithelioid colony-forming units. The inverse should also be true: at least some Ring or Epithelioid colonies must come from Dense colony-forming units.

In contrast to the Dense colonies, Endo/Acinar colonies did not require exogenous R-Spondin 1 for their formation. While Dense colony-forming units are multipotent, those that form Endo/Acinar colonies appear to be bipotent for endocrine and acinar lineages. These lineage-restricted Endo/Acinar-colony-forming units were more prevalent in dissociated Dense colonies than in Ring colonies. In contrast, freshly sorted ductal cells did not form Endo/Acinar colonies (from as many as 100,000 CD133$^+$Sox9-EGFP$^+$ cells examined). These results suggest that Endo/Acinar-colony forming units are generated only when R-Spondin 1 activates ductal stem cells; they cannot immediately arise from the steady state ductal progenitor cells. Importantly, it was found that, in the absence of R-Spondin 1, Endo/Acinar-colony-forming units may be further matured into glucose-responsive, insulin-secreting cells in vitro. This result indicates that ductal stem cells are capable of differentiating into functional β-cells in vitro.

In summary, using single-cell analyses, clearly demonstrates that adult pancreatic ducts harbor stem cells, and that these ductal stem cells are regulated by Wnt signaling in vitro. Prior to these studies, the ongoing debate as to whether these cells exist was fueled by in vivo genetic-lineage tracing studies that show pre-existing β-cells can give rise to new β-cells (Dor et al. 2004), suggesting stem cells are not required by the adult pancreas (Dor et al. 2004). Other investigators have come to a similar conclusion using techniques such as DNA dye labeling of proliferating β-cells (Teta et al. 2007) and the genetic labeling of ductal cells that express Sox9 (Kopp et al 2011a; Furuyama et al. 2011) or HNF1b (Solar et al. 2009). However, there are several limitations and inconsistencies between the studies described herein and these aforementioned in vivo studies. For example, genetic labeling marks and traces a population, rather than single cells. The underlying assumption in this type of experiment is that those genetically labeled cells are homogeneous, but in fact they are not. Stem cells are a minor population in many adult organs, and the activities of those rare cells can be easily masked by cells that are more prevalent.

This is evidenced by the Examples described above, wherein Dense-colony-forming units are a minor population in the pancreas. They comprise 55% of total ductal colony-forming progenitors (FIG. 27C), which themselves comprise only 5% of CD133$^+$Sox9-EGFP$^+$ ductal cells (FIG. 27A). Assuming ducts represent 10% of total pancreas mass, the Dense-colony-forming units represent only 0.3% of total pancreatic cells. Therefore, this population of rare stem cells may be enriched to conduct additional in vitro and in vivo studies. Enrichment may be accomplished by identifying a specific marker Further, the injury models that have been used—70% pancreatectomy (Dor et al. 2004), partial duct ligation (Kopp et al. 2011a; Furuyama et al. 2011; Xu et al. 2008), pregnancy (Teta et al. 2007), acinar cell ablation alone (Criscimanna et al. 2011) or 99% β-cell ablation (Thorel et al. 2010)—are likely not severe enough to activate the ductal stem cell compartment. Without proper in vivo activation, the activities of rare ductal stem cells cannot be easily observed. In fact, a recent study demonstrated that the in vivo depletion of both acinar and endocrine cells is necessary to promote ductal cell differentiation into acinar and endocrine lineages (Criscimanna et al. 2011). Furthermore, the activation of hematopoietic stem cells requires lethal irradiation, which depletes differentiated blood cells, to become activated (Metcalf 2007). An animal model that is used in an injury model should be capable of 1) robust injury of both acinar and endocrine cells, and 2) accepting donor cells isolated from murine or human ducts without immune rejection is vital in order to detect the activities of those rare ductal pancreatic stem cells in vivo.

Figure 34:
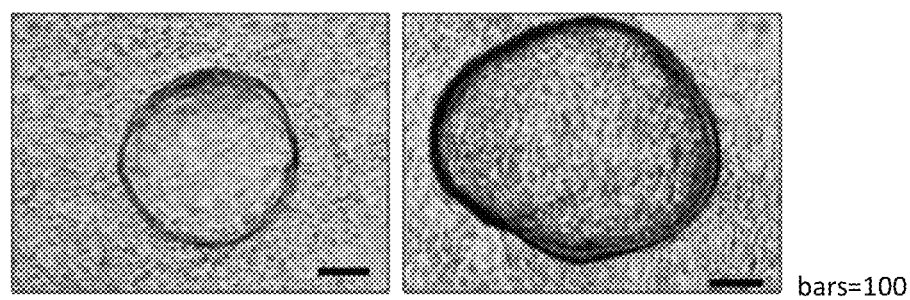
FIG. 34 shows phase-contrast photomicrographs taken from a light microscope of differentiated human pancreatic colonies developed 20 days post plating from dissociated pancreatic cells. (Bars 100 µm)
Figure 35:
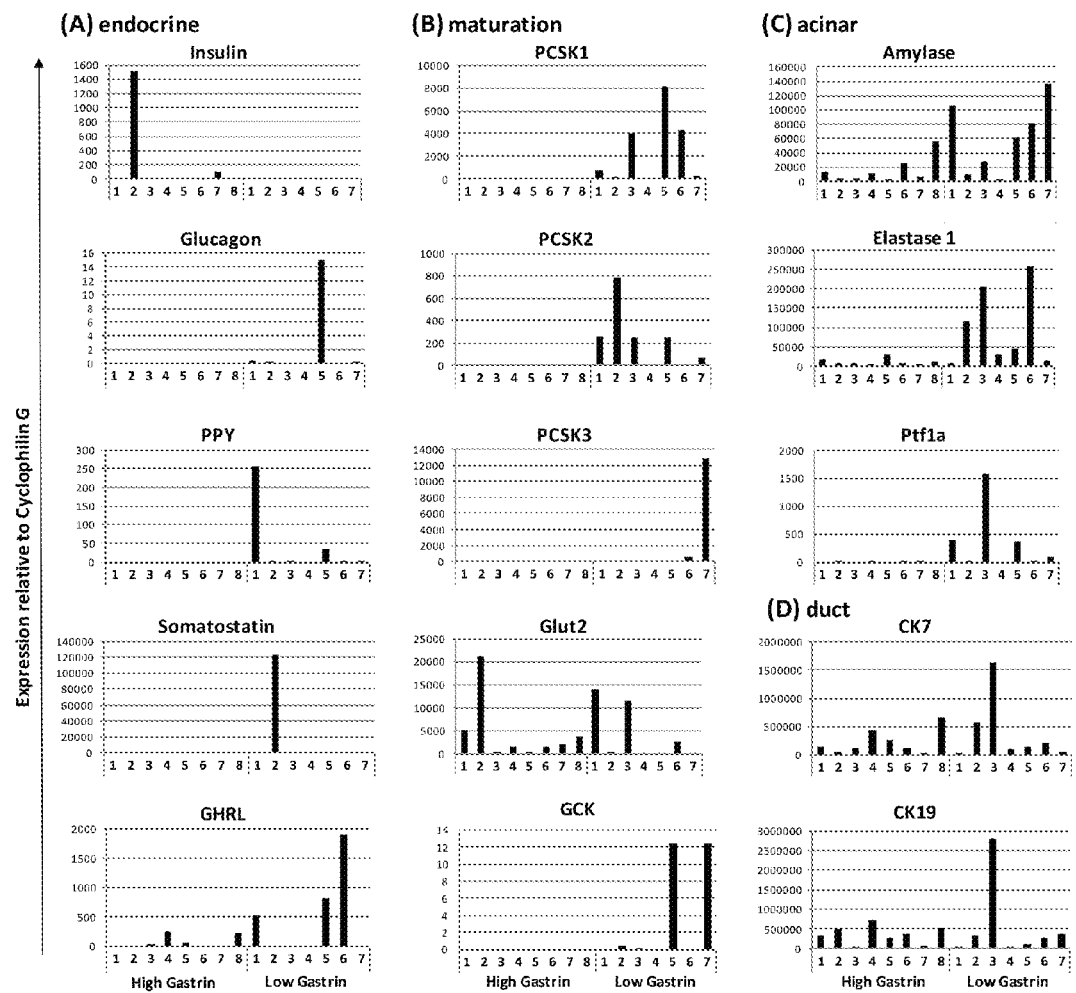
FIG. 35 is a series of microfluidic PCR analyses illustrating that human $CD133^+/CD49f^{low}$ cells express endocrine, acinar and ductal cell markers as indicated.

Example 4: Human Adult Pancreatic Progenitor Cells can be Grown in Semi-Solid Media Human "Ring" colonies are formed in a better-defined culture media. A recent breakthrough, described below, allows human adult progenitor cells to be grown in semi-solid media. These human pancreatic progenitor cells differentiate into "Ring" colonies (FIG. 34) that express endocrine (including insulin-expressing beta-like cells), acinar and ductal cell markers (FIG. 35).

Briefly, human $CD133^+/CD49f^{low}$ cells sorted from dissociated adult pancreatic cells were plated into a semisolid medium containing DMEM/F12 media, 1% (wt/vol) methylcellulose, 5% Matrigel (vol/vol), 10% (vol/vol) Serum Replacement (Invitrogen), 10 mM nicotinamide, 0.1 nM exendin4, 10 ng/ml activin betaB, 10 ng/ml VEGF, 50 ng/ml EGF, 750 ng/ml R-Spondin-1, 100 ng/ml noggin, 500 nM A 83-01, 10 μM SB202190, with designated high concentrations (100 nM) or low concentrations (10 nM) of gastrin. Individual colonies were handpicked and analyzed by microfluidic RT-PCR analysis (Fluidigm) 26 days after plating (FIG. 35). Each bar represents a colony.

These results suggest that the cocktail of growth factors included in the media are effective in driving adult pancreatic progenitor cell differentiation in culture.

REFERENCES

The references, patents and published patent applications listed below, and all references cited in the specification above are hereby incorporated by reference in their entirety, as if fully set forth herein.

Alberti K, R. E. Davey, K. Onishi, S. George, K. Salchert, F. P. Seib, M. Bornhauser, T. Pompe, A. Nagy, C. Werner, P. W. Zandstra, Nat Methods 2008, 5, 645.

Bonner-Weir S, et al. (2004) The pancreatic ductal epithelium serves as a potential pool of progenitor cells. Pediatr Diabetes 5 Suppl 2:16-22.

Bonner-Weir S, Taneja M, Weir G C, Tatarkiewicz K, Song K H, Sharma A, O'Neil J J. In vitro cultivation of human islets from expanded ductal tissue. Proc Natl Acad Sci USA 2000; 97:7999-8004.

Bonner-Weir, Endocrinology 2000, 141, 1926.

Bouwens L. Cytokeratins and cell differentiation in the pancreas. J Pathol 1998; 184:234-9.

Chen C, Chai J, Singh L, Kuo C Y, Jin L, Feng T, Marzano S, Galeni S, Zhang N, Iacovino M, Qin L, Hara M, Stein R, Bromberg J S, Kyba M, Ku H T. Characterization of an in vitro differentiation assay for pancreatic-like cell development from murine embryonic stem cells: detailed gene expression analysis. Assay Drug Dev Technol 2011; 9:403-19.

Criscimanna A, et al. (2011) Duct cells contribute to regeneration of endocrine and acinar cells following pancreatic damage in adult mice. Gastroenterology 141(4):1451-1462, 1462 e1451-1456.

de Lau W, et al. (2011) Lgr5 homologues associate with Wnt receptors and mediate R-spondin signalling. Nature 476 (7360):293-297.

Dessimoz J, Bonnard C, Huelsken J, & Grapin-Botton A (2005) Pancreas-specific deletion of beta-catenin reveals Wnt-dependent and Wnt-independent functions during development. Curr Biol 15(18):1677-1683.

Dor Y, Brown J, Martinez O I, & Melton D A (2004) Adult pancreatic beta-cells are formed by self-duplication rather than stem-cell differentiation. Nature 429(6987):41-46.

Fanjul M, Gmyr V, Sengenes C, Ratovo G, Dufresne M, Lefebvre B, Kerr-Conte J, Hollande E. Evidence for epithelial-mesenchymal transition in adult human pancreatic exocrine cells. J Histochem Cytochem 2010; 58:807-23.

Furuta M, Yano H, Zhou A, Rouille Y, Hoist J J, Carroll R, Ravazzola M, Orci L, Furuta H, Steiner D F. Defective prohormone processing and altered pancreatic islet morphology in mice lacking active SPC2. Proc Natl Acad Sci USA 1997; 94:6646-51.

Furuyama K, Kawaguchi Y, Akiyama H, Horiguchi M, Kodama S, Kuhara T, Hosokawa S, Elbahrawy A, Soeda T, Koizumi M, Masui T, Kawaguchi M, Takaori K, Doi R, Nishi E, Kakinoki R, Deng J M, Behringer R R, Nakamura T, Uemoto S. Continuous cell supply from a Sox9-expressing progenitor zone in adult liver, exocrine pancreas and intestine. Nat Genet. 2011; 43:34-41.

Gao R, Ustinov J, Korsgren O, Otonkoski T. In vitro neogenesis of human islets reflects the plasticity of differentiated human pancreatic cells. Diabetologia 2005; 48:2296-2304.

Gao R, Ustinov J, Pulkkinen M A, Lundin K, Korsgren O, Otonkoski T. Characterization of endocrine progenitor cells and critical factors for their differentiation in human adult pancreatic cell culture. Diabetes 2003; 52:2007-2015.

Githens S. The pancreatic duct cell: proliferative capabilities, specific characteristics, metaplasia, isolation, and culture. J Pediatr Gastroenterol Nutr 1988; 7:486-506.

Gong S, Zheng C, Doughty M L, Losos K, Didkovsky N, Schambra U B, Nowak N J, Joyner A, Leblanc G, Hatten M E, Heintz N. A gene expression atlas of the central nervous system based on bacterial artificial chromosomes. Nature 2003; 425:917-25.

Gu G, Brown J R, Melton D A. Direct lineage tracing reveals the ontogeny of pancreatic cell fates during mouse embryogenesis. Mech Dev 2003; 120:35-43.

Gu G, Dubauskaite J, & Melton D A (2002) Direct evidence for the pancreatic lineage: NGN3+ cells are islet progenitors and are distinct from duct progenitors. Development 129(10):2447-2457.

Hao E, Tyrberg B, Itkin-Ansari P, Lakey J R, Geron I, Monosov E Z, Barcova M, Mercola M, Levine F. Beta-cell differentiation from nonendocrine epithelial cells of the adult human pancreas. Nature medicine 2006; 12:310-316.

Heilshorn, K. A. DiZio, E. R. Welsh, D. A. Tirrell, Biomaterials 2003, 24, 4245.

Heiser P W, Lau J, Taketo M M, Herrera P L, & Hebrok M (2006) Stabilization of beta-catenin impacts pancreas growth. Development 133(10):2023-2032.

Heller R S, et al. (2002) Expression patterns of Wnts, Frizzleds, sFRPs, and misexpression in transgenic mice suggesting a role for Wnts in pancreas and foregut pattern formation. Dev Dyn 225(3):260-270.

Herbach, M. Bergmayr, B. Goke, E. Wolf, R. Wanke, PLoS One 2011, 6, e22814.

Hori Y, Fukumoto M, Kuroda Y. Enrichment of putative pancreatic progenitor cells from mice by sorting for prominin1 (CD133) and platelet-derived growth factor receptor beta. Stem Cells 2008; 26:2912-20.

Immervoll H, Hoem D, Sakariassen P O, Steffensen O J, Molven A. Expression of the "stem cell marker" CD133 in pancreas and pancreatic ductal adenocarcinomas. BMC Cancer 2008; 8:48.

Inada A, Nienaber C, Katsuta H, Fujitani Y, Levine J, Morita R, Sharma A, Bonner-Weir S. Carbonic anhydrase II-positive pancreatic cells are progenitors for both endocrine and exocrine pancreas after birth. Proc Natl Acad Sci USA 2008; 105:19915-9.

Jonsson J, Carlsson L, Edlund T, & Edlund H (1994) Insulin-promoter-factor 1 is required for pancreas development in mice. Nature 371(6498):606-609.

Jorgensen M C, Ahnfelt-Ronne J, Hald J, Madsen O D, Serup P, Hecksher-Sorensen J. An illustrated review of early pancreas development in the mouse. Endocr Rev 2007; 28:685-705.

Khademhosseini A, R. Langer, J. Borenstein, J. P. Vacanti, Proc Natl Acad Sci USA 2006, 103, 2480.

Kilic G, Wang J, Sosa-Pineda B. Osteopontin is a novel marker of pancreatic ductal tissues and of undifferentiated pancreatic precursors in mice. Dev Dyn 2006; 235:1659-67.

Kim K A, et al. (2005) Mitogenic influence of human R-spondin1 on the intestinal epithelium. Science 309 (5738):1256-1259.

Kobayashi H, Spilde T L, Li Z, Marosky J K, Bhatia A M, Hembree M J, Prasadan K, Preuett B L, Gittes G K. Lectin as a marker for staining and purification of embryonic pancreatic epithelium. Biochem Biophys Res Commun 2002; 293:691-7.

Kopinke D, Murtaugh L C. Exocrine-to-endocrine differentiation is detectable only prior to birth in the uninjured mouse pancreas. BMC Dev Biol 2010; 10:38.

Kopp J L, Dubois C L, Schaffer A E, Hao E, Shih H P, Seymour P A, Ma J, Sander M. Sox9+ ductal cells are multipotent progenitors throughout development but do not produce new endocrine cells in the normal or injured adult pancreas. Development 2011a; 138:653-65.

Kopp J L, et al. Progenitor cell domains in the developing and adult pancreas. Cell Cycle 2011b; 10(12):1921-1927.

Kragl, E. Lammed, Adv Exp Med Biol 2010, 654, 217.

Ku H T, Chai J, Kim Y J, White P, Purohit-Ghelani S, Kaestner K H, Bromberg J S. Insulin-expressing colonies developed from murine embryonic stem cell-derived progenitors. Diabetes 2007; 56:921-929.

Ku H T. Minireview: pancreatic progenitor cells—recent studies. Endocrinology 2008; 149:4312-4316.

Lardon J, Corbeil D, Huttner W B, Ling Z, Bouwens L. Stem cell marker prominin-1/AC133 is expressed in duct cells of the adult human pancreas. Pancreas 2008; 36:e1-6.

Li W C, Rukstalis J M, Nishimura W, Tchipashvili V, Habener J F, Sharma A, Bonner-Weir S. Activation of pancreatic-duct-derived progenitor cells during pancreas regeneration in adult rats. J Cell Sci 2010; 123:2792-802.

Lu W, et al. (2008) R-spondin1 synergizes with Wnt3A in inducing osteoblast differentiation and osteoprotegerin expression. FEBS Lett 582(5):643-650.

Malide D, Seidah N G, Chretien M, Bendayan M. Electron microscopic immunocytochemical evidence for the involvement of the converts PC1 and PC2 in the processing of proinsulin in pancreatic beta-cells. J Histochem Cytochem 1995; 43:11-9.

May R, Sureban S M, Lightfoot S A, Hoskins A B, Brackett D J, Postier R G, Ramanujam R, Rao C V, Wyche J H, Anant S, Houchen C W. Identification of a novel putative pancreatic stem/progenitor cell marker DCAMKL-1 in normal mouse pancreas. Am J Physiol Gastrointest Liver Physiol 2010; 299:G303-10.

Metcalf D (2007) Concise review: hematopoietic stem cells and tissue stem cells: current concepts and unanswered questions. Stem Cells 25(10):2390-2395.

Nam J S, Turcotte T J, Smith P F, Choi S, & Yoon J K (2006) Mouse cristin/Rspondin family proteins are novel ligands for the Frizzled 8 and LRP6 receptors and activate beta-catenin-dependent gene expression. J Biol Chem 281(19): 13247-13257.

Nikolova, N. Jabs, I. Konstantinova, A. Domogatskaya, K. Tryggvason, L. Sorokin, R. Fassler, G. Gu, H. P. Gerber, N. Ferrara, D. A. Melton, E. Lammert, Dev Cell 2006, 10, 397.

Nowatzki, D. A. Tirrell, Biomaterials 2004, 25, 1261.

Ootani A, et al. (2009) Sustained in vitro intestinal epithelial culture within a Wnt-dependent stem cell niche. Nat Med 15(6):701-706.

Oshima Y, Suzuki A, Kawashimo K, Ishikawa M, Ohkohchi N, Taniguchi H. Isolation of mouse pancreatic ductal progenitor cells expressing CD133 and c-Met by flow cytometric cell sorting. Gastroenterology 2007; 132:720-32.

Parma P, et al. (2006) R-spondin1 is essential in sex determination, skin differentiation and malignancy. Nat Genet. 38(11):1304-1309.

Parnaud, E. Hammar, D. G. Rouiller, M. Armanet, P. A. Halban, D. Bosco, Diabetes 2006, 55, 1413.

Peifer M & Polakis P (2000) Wnt signaling in oncogenesis and embryogenesis—a look outside the nucleus. Science 287(5458):1606-1609.

Pinho A V, Rooman I, Reichert M, De Medts N, Bouwens L, Rustgi A K, Real FX. Adult pancreatic acinar cells dedifferentiate to an embryonic progenitor phenotype with concomitant activation of a senescence programme that is present in chronic pancreatitis. Gut 2011; 60:958-966.

Pinkse, W. P. Bouwman, R. Jiawan-Lalai, O. T. Terpstra, J. A. Bruijn, E. de Heer, Diabetes 2006, 55, 312.

Piper K, Ball S G, Keeling J W, Mansoor S, Wilson D I, Hanley N A. Novel SOX9 expression during human pancreas development correlates to abnormalities in Campomelic dysplasia. Mech Dev 2002; 116:223-6.

Piper K, Brickwood S, Turnpenny L W, Cameron I T, Ball S G, Wilson D I, Hanley N A. Beta cell differentiation during early human pancreas development. The Journal of endocrinology 2004; 181:11-23.

Rajagopal, W. J. Anderson, S. Kume, 0.1. Martinez, D. A. Melton, Science 2003, 299, 363.

Rovira M, Scott S G, Liss A S, Jensen J, Thayer S P, Leach S D. Isolation and characterization of centroacinar/terminal ductal progenitor cells in adult mouse pancreas. Proc Natl Acad Sci USA 2010; 107:75-80.

Rulifson I C, et al. (2007) Wnt signaling regulates pancreatic beta cell proliferation. Proc Natl Acad Sci USA 104(15): 6247-6252.

Sato T, et al. (2009) Single Lgr5 stem cells build crypt-villus structures in vitro without a mesenchymal niche. Nature 459(7244):262-265.

Schreiber F S, Deramaudt T B, Brunner T B, Boretti M I, Gooch K J, Stoffers D A, Bernhard E J, Rustgi A K. Successful growth and characterization of mouse pancreatic ductal cells: functional properties of the Ki-RAS (G12V) oncogene. Gastroenterology 2004; 127:250-60.

Seaberg R M, Smukler S R, Kieffer T J, Enikolopov G, Asghar Z, Wheeler M B, Korbutt G, van der Kooy D. Clonal identification of multipotent precursors from adult mouse pancreas that generate neural and pancreatic lineages. Nature biotechnology 2004; 22:1115-1124.

Seymour P A, Freude K K, Dubois C L, Shih H P, Patel N A, Sander M. A osagedependent requirement for Sox9 in pancreatic endocrine cell formation. Dev Biol 2008; 323: 19-30.

Seymour P A, Freude K K, Tran M N, Mayes E E, Jensen J, Kist R, Scherer G, Sander M. SOX9 is required for maintenance of the pancreatic progenitor cell pool. Proceedings of the National Academy of Sciences of the United States of America 2007; 104:1865-1870.

Sharma A, Zangen D H, Reitz P, Taneja M, Lissauer M E, Miller C P, Weir G C, Habener J F, Bonner-Weir S. The homeodomain protein IDX-1 increases after an early burst of proliferation during pancreatic regeneration. Diabetes 1999; 48:507-513.

Shin S, Walton G, Aoki R, Brondell K, Schug J, Fox A, Smirnova O, Dorrell C, Erker L, Chu A S, Wells R G, Grompe M, Greenbaum L E, Kaestner K H. FoxI1-Cre-marked adult hepatic progenitors have clonogenic and bilineage differentiation potential. Genes Dev 2011; 25:1185-92.

Smukler S R, Arntfield M E, Razavi R, Bikopoulos G, Karpowicz P, Seaberg R, Dai F, Lee S, Ahrens R, Fraser P E, Wheeler M B, van der Kooy D. The adult mouse and human pancreas contain rare multipotent stem cells that express insulin. Cell Stem Cell 2011; 8:281-93.

Solar M, Cardalda C, Houbracken I, Martin M, Maestro M A, De Medts N, Xu X, Grau V, Heimberg H, Bouwens L, Ferrer J. Pancreatic exocrine duct cells give rise to insulin-producing beta cells during embryogenesis but not after birth. Dev Cell 2009; 17:849-60.

Suarez-Pinzon W L, Lakey J R, Brand S J, Rabinovitch A. Combination therapy with epidermal growth factor and gastrin induces neogenesis of human islet {beta}-cells from pancreatic duct cells and an increase in functional {beta}-cell mass. J Clin Endocrinol Metab 2005; 90:3401-9.

Sugiyama T, Rodriguez R T, McLean G W, Kim S K. Conserved markers of fetal pancreatic epithelium permit prospective isolation of islet progenitor cells by FACS. Proceedings of the National Academy of Sciences of the United States of America 2007; 104:175-180.

Suzuki A, Nakauchi H, Taniguchi H. Prospective isolation of multipotent pancreatic progenitors using flow-cytometric cell sorting. Diabetes 2004; 53:2143-2152.

Teta M, Rankin M M, Long S Y, Stein G M, & Kushner J A (2007) Growth and regeneration of adult beta cells does not involve specialized progenitors. Developmental cell 12(5):817-826.

Thorel F, et al. (2010) Conversion of adult pancreatic alpha-cells to beta-cells after extreme beta-cell loss. Nature 464(7292):1149-1154.

Walker N I, Winterford C M, Kerr J F. Ultrastructure of the rat pancreas after experimental duct ligation. II. Duct and stromal cell proliferation, differentiation, and deletion. Pancreas 1992; 7:420-34.

Wang H, Brun T, Kataoka K, Sharma A J, Wollheim C B. MAFA controls genes implicated in insulin biosynthesis and secretion. Diabetologia 2007; 50:348-58.

Watanabe M, Muramatsu T, Shirane H, Ugai K. Discrete Distribution of binding sites for *Dolichos* biflorus agglutinin (DBA) and for peanut agglutinin (PNA) in mouse organ tissues. J Histochem Cytochem 1981; 29:779-80.

Weber, K. N. Hayda, K. Haskins, K. S. Anseth, Biomaterials 2007, 28, 3004.

Weber, K. S. Anseth, Matrix Biol 2008, 27, 667.

Wescott M P, Rovira M, Reichert M, von Burstin J, Means A, Leach S D, Rustgi A K. Pancreatic ductal morphogenesis and the Pdx1 homeodomain transcription factor. Mol Biol Cell 2009; 20:4838-44.

Wheeldon, A. Farhadi, A. G. Bick, E. Jabbari, A. Khademhosseini, Nanotechnology 2011, 22, 212001.

Winkler M, Trieu N, Feng T, Jin L, Walker S, Singh L, Ku H T. A quantitative assay for insulin-expressing colony-forming progenitors. J V is Exp 2011:e3148.

Wong V S, Yeung A, Schultz W, & Brubaker P L (2010) R-spondin-1 is a novel beta-cell growth factor and insulin secretagogue. J Biol Chem 285(28):2129221302.

Xu X, D'Hoker J, Stange G, Bonne S, De Leu N, Xiao X, Van de Casteele M, Mellitzer G, Ling Z, Pipeleers D, Bouwens L, Scharfmann R, Gradwohl G, Heimberg H. Beta cells can be generated from endogenous progenitors in injured adult mouse pancreas. Cell 2008; 132:197-207.

Yatoh S, Dodge R, Akashi T, Omer A, Sharma A, Weir G C, Bonner-Weir S. Differentiation of affinity-purified human pancreatic duct cells to beta-cells. Diabetes 2007; 56:1802-1809.

Zhao J, et al. (2007a) R-spondin1, a novel intestinotrophic mitogen, ameliorates experimental colitis in mice. Gastroenterology 132(4):1331-1343.

Zhou Q, et al. (2007b) A multipotent progenitor domain guides pancreatic organogenesis. Developmental cell 13(1):103-114.

What is claimed is:

1. A method of improving the survival of pancreatic β-cell progenitors in culture comprising:
   contacting a population of pancreatic progenitor cells with an artificial extracellular matrix (aECM) protein, the aECM protein comprising
   a) a first amino acid sequence comprising a functional portion of elastin comprising [(VPGIG)$_2$VPGKG(VPGIG)$_2$]$_4$ (SEQ ID NO: 3); and
   b) a second amino acid sequence comprising SEQ ID NO:2;
   wherein the aECM protein improves survival of the population of pancreatic β-cell progenitors, and
   wherein the population of pancreatic progenitor cells express one or more pancreatic progenitor cell markers selected from Pdx1, Ngn3, Nkx6.1, Pax4, MafB, c-Met, DCAMKL1, and DCAMKL2.

2. The method of claim 1, wherein the population of pancreatic progenitor cells is derived from a population of adult pancreatic ductal cells.

3. The method of claim 1, wherein the aECM protein further comprises a T7 tag.

4. A method of improving the survival of pancreatic β-cell progenitors in culture comprising:
   contacting a population of pancreatic progenitor cells with an artificial extracellular matrix (aECM) protein,
   wherein the aECM protein comprises MASMTG-GQQMG-HHHHHH-MKL{X-Y-VP}$_3$LE (SEQ ID NO:4),
   wherein X is substituted with a second amino acid sequence comprising a functional portion of the α-chain of laminin comprising IKVAV (SEQ ID NO: 1) and Y is substituted with a first amino acid sequence comprising a functional portion of elastin comprising [(VPGIG)$_2$VPGKG(VPGIG)$_2$]$_4$ (SEQ ID NO: 3),
   wherein the aECM protein improves survival of the population of pancreatic β-cell progenitors, and
   wherein the population of pancreatic progenitor cells express one or more pancreatic progenitor cell markers selected from Pdx1, Ngn3, Nkx6.1, Pax4, MafB, c-Met, DCAMKL1, and DCAMKL2.

5. The method of claim 4, wherein the second amino acid sequence is SEQ ID NO:2.

6. The method of claim 4, wherein the first amino acid sequence is SEQ ID NO:3 and the second amino acid sequence is SEQ ID NO:2.

7. A method of improving the survival of pancreatic β-cell progenitors in culture comprising:
   contacting a population of pancreatic progenitor cells with an artificial extracellular matrix (aECM) protein, the aECM protein comprising
   a) a first amino acid sequence comprising SEQ ID NO:3; and
   b) a second amino acid sequence comprising SEQ ID NO:2;
   wherein the aECM protein improves survival of the population of pancreatic β-cell progenitors.

8. The method of claim 7, wherein the aECM protein further comprises a T7 tag.

9. A method of improving the survival of pancreatic β-cell progenitors in culture comprising contacting a population of pancreatic progenitor cells with an artificial extracellular matrix (aECM) protein comprising MASMTGGQQMG-HHHHHH-MKL{X-Y-VP}$_3$LE (SEQ ID NO:4), wherein X is substituted with a second amino acid sequence comprising SEQ ID NO: 1 and Y is substituted with a first amino acid sequence comprising SEQ ID NO: 3, and wherein the aECM protein improves survival of the population of pancreatic β-cell progenitors.

10. A method of improving the survival of pancreatic β-cell progenitors in culture comprising:
   contacting a population of pancreatic progenitor cells with an artificial extracellular matrix (aECM) protein, the aECM protein comprising MASMTGGQQMG-HHH-HHH-MKL{X-Y-VP}$_3$LE (SEQ ID NO:4), wherein
   X is a laminin component comprising IKVAV (SEQ ID NO: 1) and Y is an elastin component comprising [(VPGIG)$_2$VPGKG(VPGIG)$_2$]$_4$ (SEQ ID NO: 3), or
   X is an elastin component comprising [(VPGIG)$_2$VPGKG(VPGIG)$_2$]$_4$ (SEQ ID NO: 3) and Y is a laminin component comprising IKVAV (SEQ ID NO: 1), and
   wherein the aECM protein improves survival of the population of pancreatic β-cell progenitors.

11. A method of improving the survival of pancreatic β-cell progenitors in culture comprising:
   contacting a population of pancreatic progenitor cells with an artificial extracellular matrix (aECM) protein, the aECM protein comprising MASMTGGQQMG-HHH-HHH-MKL{X-Y-VP}$_3$LE (SEQ ID NO:4), wherein:
   X comprises LDASMSVQAVDRSANKARIVS-KAASA (SEQ ID NO:6) or VPLDYAVTGRGDS-PASSKIPIA (SEQ ID NO:7); and
   Y is substituted with [(VPGIG)$_2$VPGKG(VPGIG)$_2$]$_4$ (SEQ ID NO: 3);
   wherein the aECM protein improves survival of the population of pancreatic β-cell progenitors.

* * * * *

UNITED STATES PATENT AND TRADEMARK OFFICE
CERTIFICATE OF CORRECTION

Page 1 of 1

PATENT NO. : 9,783,784 B2
APPLICATION NO. : 13/831382
DATED : October 10, 2017
INVENTOR(S) : Hsun Ku et al.

It is certified that error appears in the above-identified patent and that said Letters Patent is hereby corrected as shown below:

In the Specification

Statement of Government Interest section, Column 1, Lines 15-17, please delete:
"This invention was made with government support under RO1 DK081587 and U01 DK089533 each awarded by NIH. The Government has certain rights in the invention."

And insert:
--This invention was made with government support under U01 DK089533, and R01 DK081587 awarded by the National Institutes of Health. The government has certain rights in the invention.--

Signed and Sealed this
Fifteenth Day of July, 2025

Coke Morgan Stewart
*Acting Director of the United States Patent and Trademark Office*